US012746282B2

(12) United States Patent
Hausmann et al.

(10) Patent No.: US 12,746,282 B2
(45) Date of Patent: Sep. 29, 2026

(54) RECOMBINANT MODIFIED VACCINIA VIRUS (MVA) VACCINE AGAINST CORONAVIRUS DISEASE

(71) Applicant: Bavarian Nordic A/S, Hellerup (DK)

(72) Inventors: Jürgen Hausmann, Gundelfingen (DE); Robin Steigerwald, Munich (DE); Matthias Habjan, Puchheim (DE); José Medina Echeverz, Munich (DE); Stephan Rambichler, Munich (DE)

(73) Assignee: Bavarian Nordic A/S, Hellerup (DK)

( * ) Notice: Subject to any disclaimer, the term of this patent is extended or adjusted under 35 U.S.C. 154(b) by 791 days.

(21) Appl. No.: 18/008,937

(22) PCT Filed: Jun. 10, 2021

(86) PCT No.: PCT/EP2021/065726
§ 371 (c)(1),
(2) Date: Dec. 7, 2022

(87) PCT Pub. No.: WO2021/250219
PCT Pub. Date: Dec. 16, 2021

(65) Prior Publication Data

US 2023/0233670 A1 Jul. 27, 2023

(30) Foreign Application Priority Data

Jun. 10, 2020 (EP) .................................... 20179347

(51) Int. Cl.
*A61K 39/215* (2006.01)
*A61P 31/14* (2006.01)
(Continued)

(52) U.S. Cl.
CPC ............ *A61K 39/215* (2013.01); *A61P 31/14* (2018.01); *C12N 7/00* (2013.01);
(Continued)

(58) Field of Classification Search
None
See application file for complete search history.

(56) References Cited

U.S. PATENT DOCUMENTS

2016/0030551 A1* 2/2016 Cheminay ............... A61P 37/04 424/199.1
2021/0283244 A1 9/2021 Chen et al.
2022/0347289 A1 11/2022 Chen et al.

FOREIGN PATENT DOCUMENTS

CN 111088283 A 5/2020
CN 111218459 A 6/2020
(Continued)

OTHER PUBLICATIONS

Song, Fei; et al; "Middle East Respiratory Syndrome Coronavirus Spike Protein Delivered by Modified Vaccinia Virus Ankara Efficiently Induces Virus-Neutralizing Antibodies" Journal of Virology, 87, 11950-11954, 2013 (Year: 2013).*
(Continued)

*Primary Examiner* — David W Berke-Schlessel

(57) ABSTRACT

The invention relates to a recombinant Modified Vaccinia Virus Ankara (MVA) encoding a spike (S) protein or a part thereof, such as a receptor-binding domain (RBD), and additional antigenic sequences derived from other proteins of severe acute respiratory syndrome coronavirus-2 (SARS-CoV-2), the causative agent of coronavirus disease 19 (COVID-19).

16 Claims, 20 Drawing Sheets

Specification includes a Sequence Listing.

(51) Int. Cl.
*C12N 7/00* (2006.01)
*A61K 39/00* (2006.01)

(52) U.S. Cl.
CPC ................. *A61K 2039/5256* (2013.01); *A61K 2039/545* (2013.01); *A61K 2039/575* (2013.01); *C12N 2710/24121* (2013.01); *C12N 2770/20034* (2013.01)

(56) References Cited

FOREIGN PATENT DOCUMENTS

| | | | | | |
|---|---|---|---|---|---|
| WO | WO-2006079290 | A1 * | 8/2006 | ............. | A61P 31/14 |
| WO | WO 2010102822 | A1 | 9/2010 | | |
| WO | WO 2014024026 | A1 | 2/2014 | | |
| WO | 2016046357 | A1 | 3/2016 | | |
| WO | WO 2018176103 | A1 | 10/2018 | | |
| WO | 2021163622 | A1 | 8/2021 | | |

OTHER PUBLICATIONS

Bisht, Himani; et al; "Severe acute respiratory syndrome coronavirus spike protein expressed by attenuated vaccinia virus protectively immunizes mice" Proceedings of the National Academy of Sciences, 101, 6641-6646, 2004 (Year: 2004).*

Chen, Zhiwei; et al; "Recombinant Modified Vaccinia Virus Ankara Expressing the Spike Glycoprotein of Severe Acute Respiratory Syndrome Coronavirus Induces Protective Neutralizing Antibodies Primarily Targeting the Receptor Binding Region" Journal of Virology, 2678-2688, 2005 (Year: 2005).*

Anonymous, "Klinische Tests konnen im September beginnen," News Release May 18, 2020, retrieved from the internet on Oct. 28, 2020 from <https://www.uni-muenchen.de/forschung/news/2020/sutter_impstoff_marburg.html> (as cited in the International Search Report for parent PCT/EP2021/065726 dated Sep. 16, 2021).

Anonymous, "Draft landscape of COVID-19 candidate vaccines—Apr. 20, 2020," retrieved from the internet on Oct. 28, 2020 from <https://www.who.int/blueprint/priority-diseases/key-action/novel-coronavirus-landscape-ncov.pdf> (as cited in the International Search Report for parent PCT/EP2021/065726 dated Sep. 16, 2021).

Czub et al., "Evaluation of modified vaccinia virus Ankara based recombinant SARS vaccine in ferrets," Vaccine, 2005, pp. 2273-2279, vol. 23.

Enjuanes et al., "Novel human pathogenic coronavirus: SARS-CoV-2," dated Mar. 26, 2020, retrieved from the internet on Oct. 29, 2020 from <https://fems-microbiology.org/wp-content/uploads/2020/03/Enjuanes-Sola-Zuniga-2020.-Novel-Human-Pathogenic-Coronavirus-SARS-CoV-2.pdf> (as cited in the International Search Report for parent PCT/EP2021/065726 dated Sep. 16, 2021).

Ortiz-Prado et al., "Clinical, molecular, and epidemiological characterization of the SARS-CoV-2 virus and the Coronavirus Disease 2019 (COVID-19), a comprehensive literature review," Diagnostic Microbiology and Infectious Disease, 2020, p. 115094, vol. 98.

Penner, "Conserved high free energy sites in human coronavirus spike glycoprotein backbones," Journal of Computational Biology, 2020, pp. 1-9, vol. 27.

Tai et al., "Characterization of the receptor-binding domain (RBD) of 2019 novel coronavirus: implication for development of RBD protein as a viral attachment inhibitor and vaccine," Cellular & Molecular Immunology, 2020, pp. 613-620, vol. 17.

Wrapp et al., "Cryo-EM structure of the 2019-nCoV spike in the prefusion conformation," bioRxiv, dated Feb. 15, 2020, doi 10.1101/2020.02.11.944462 (cited in the International Search Report for parent PCT/EP2021/065726 dated Sep. 16, 2021).

* cited by examiner

Fig. 2

Full length protein 3a sequence: 275 amino acids

1 56
MDLFMRIFTIGTVTLKQGEIKDATPSDFVRATATIPIQASLPFGWLIVGVALLAVFQSASKIITLKKRWQLALSKGVHF
83
VCNLLLLFVTVYSHLLLVAAGLEAPFLYLYALVYFLQSINFVRIIMRLWLCWKCRSKNPLLYDANYFLCWHTNCYDYCI
178
PYNSVTSSIVITSGDGTTSPISEHDYQIGGYTEKWESGVKDCVVLHSYFTSDYYQLYSTQLSTDTGVEHVTFFIYNKIV
275
DEPEEHVQIHTIDGSSGVVNPVMEPIYDEPTTTTSVPL

Full length E sequence: 75 amino acids

1 38 73 75
MYSFVSEETGTLIVNSVLLFLAFVVFLLVTLAILTALRLCAYCCNIVNVSLVKPSFYVYSRVKNLNSSRVPDLLV

Full length M sequence: 222 amino acids

1 37 51
MADSNGTITVEELKKLLEQWNLVIGFLFLTWICLLQFAYANRNRFLYIIKLIFLWLLWPVTLACFVLAAVYRINWITGG
94
IAIAMACLVGLMWLSYFIASFRLFARTRSMWSFNPETNILLNVPLHGTILTRPLLESELVIGAVILRGHLRIAGHHLGR
212 222
CDIKDLPKEITVATSRTLSYYKLGASQRVAGDSGFAAYSRYRIGNYKLNTDHSSSSDNIALLVQ

Fig. 4 continued

G Y F K I Y S K H T P I N L V R D L P Q G F S A L E P L V D L P I

S1 domain

NTD

SARS-2 S-FS-1

G I N I T R F Q T L L A L H R S Y L T P G D S S S G W T A G A A A

S1 domain

NTD

SARS-2 S-FS-1

Y Y V G Y L Q P R T F L L K Y N E N G T I T D A V D C A L D P L S

S1 domain

NTD

SARS-2 S-FS-1

E T K C T L K S F T V E K G I Y Q T S N F R V Q P T E S I V R F P

S1 domain

NTD

SARS-2 S-FS-1

N I T N L C P F G E V F N A T R F A S V Y A W N R K R I S N C V A

S1 domain

RBD

SARS-2 S-FS-1

D Y S V L Y N S A S F S T F K C Y G V S P T K L N D L C F T N V Y

S1 domain

RBD

SARS-2 S-FS-1

Fig. 10
A
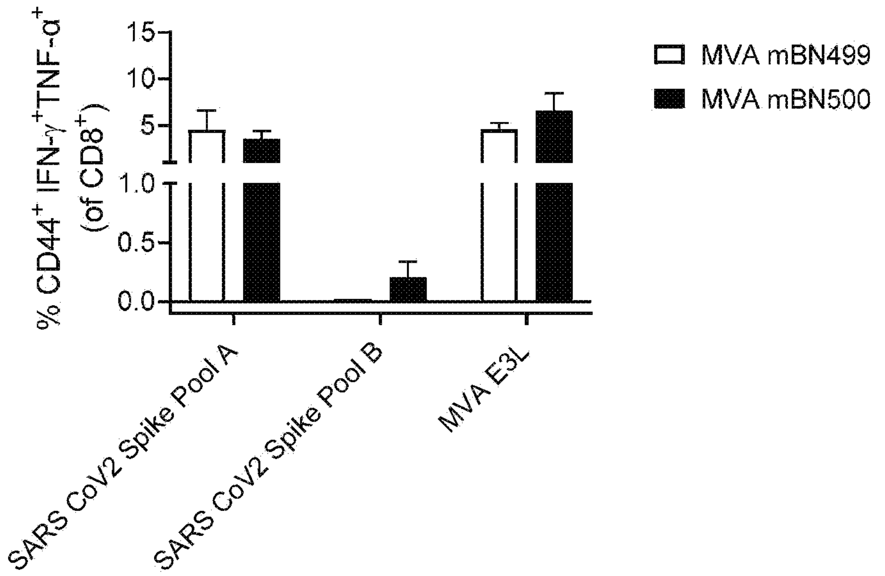
B
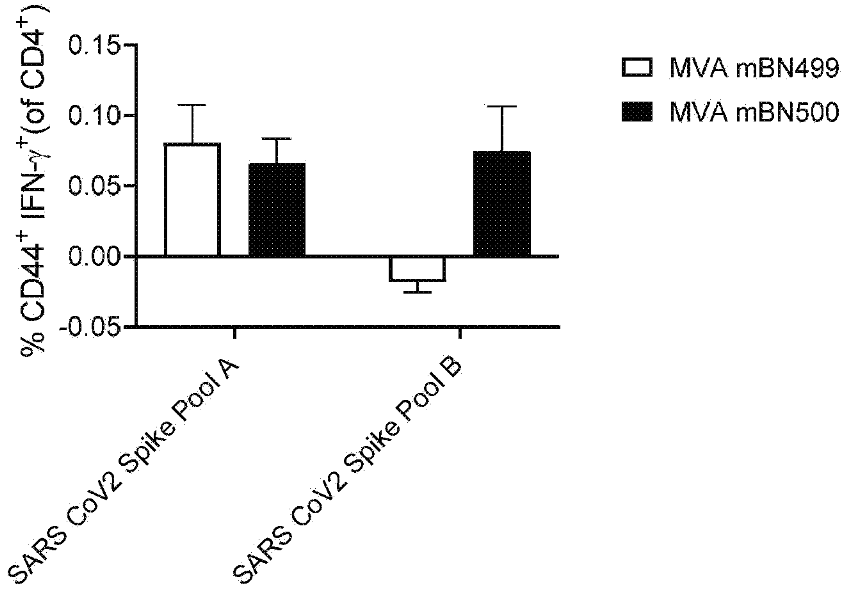

Fig. 11
A
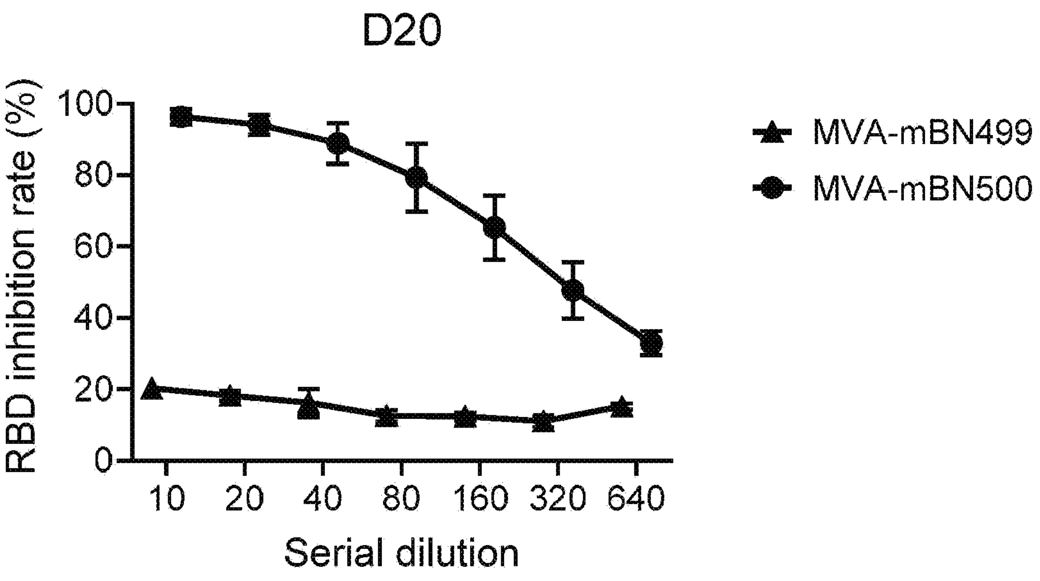
B
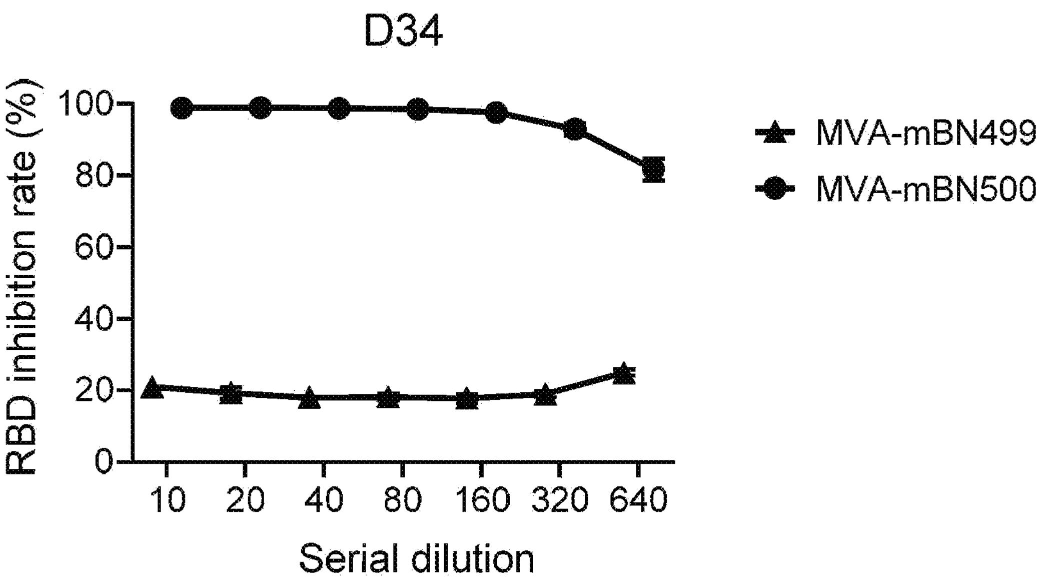

SEQUENCE LISTING

<160> NUMBER OF SEQ ID NOS: 27

<210> SEQ ID NO 1
<211> LENGTH: 1273
<212> TYPE: PRT
<213> ORGANISM: SARS coronavirus
<220> FEATURE:
<223> OTHER INFORMATION: SARS-CoV-2 S protein, full-length

<400> SEQUENCE: 1

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240
```

-continued

```
Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
```

```
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg Leu Gln Ser Leu Gln Thr Tyr Val
        995                 1000                1005

Thr Gln Gln Leu Ile Arg Ala Ala Glu Ile Arg Ala Ser Ala Asn Leu
    1010                1015                1020

Ala Ala Thr Lys Met Ser Glu Cys Val Leu Gly Gln Ser Lys Arg Val
1025                1030                1035                1040

Asp Phe Cys Gly Lys Gly Tyr His Leu Met Ser Phe Pro Gln Ser Ala
                1045                1050                1055

Pro His Gly Val Val Phe Leu His Val Thr Tyr Val Pro Ala Gln Glu
            1060                1065                1070

Lys Asn Phe Thr Thr Ala Pro Ala Ile Cys His Asp Gly Lys Ala His
        1075                1080                1085
```

```
Phe Pro Arg Glu Gly Val Phe Val Ser Asn Gly Thr His Trp Phe Val
    1090                1095                1100

Thr Gln Arg Asn Phe Tyr Glu Pro Gln Ile Ile Thr Thr Asp Asn Thr
1105                1110                1115                1120

Phe Val Ser Gly Asn Cys Asp Val Val Ile Gly Ile Val Asn Asn Thr
                1125                1130                1135

Val Tyr Asp Pro Leu Gln Pro Glu Leu Asp Ser Phe Lys Glu Glu Leu
            1140                1145                1150

Asp Lys Tyr Phe Lys Asn His Thr Ser Pro Asp Val Asp Leu Gly Asp
        1155                1160                1165

Ile Ser Gly Ile Asn Ala Ser Val Val Asn Ile Gln Lys Glu Ile Asp
    1170                1175                1180

Arg Leu Asn Glu Val Ala Lys Asn Leu Asn Glu Ser Leu Ile Asp Leu
1185                1190                1195                1200

Gln Glu Leu Gly Lys Tyr Glu Gln Tyr Ile Lys Trp Pro Trp Tyr Ile
                1205                1210                1215

Trp Leu Gly Phe Ile Ala Gly Leu Ile Ala Ile Val Met Val Thr Ile
            1220                1225                1230

Met Leu Cys Cys Met Thr Ser Cys Cys Ser Cys Leu Lys Gly Cys Cys
        1235                1240                1245

Ser Cys Gly Ser Cys Cys Lys Phe Asp Glu Asp Asp Ser Glu Pro Val
    1250                1255                1260

Leu Lys Gly Val Lys Leu His Tyr Thr
1265                1270


<210> SEQ ID NO 2
<211> LENGTH: 3822
<212> TYPE: DNA
<213> ORGANISM: SARS coronavirus
<220> FEATURE:
<223> OTHER INFORMATION: SARS-CoV-2 S protein, full-length

<400> SEQUENCE: 2

atgtttgttt ttcttgtttt attgccacta gtctctagtc agtgtgttaa tcttacaacc     60

agaactcaat tacccccctgc atacactaat tctttcacac gtggtgttta ttaccctgac    120

aaagttttca gatcctcagt tttacattca actcaggact tgttcttacc tttcttttcc    180

aatgttactt ggttccatgc tatacatgtc tctgggacca atggtactaa gaggtttgat    240

aaccctgtcc taccatttaa tgatggtgtt tattttgctt ccactgagaa gtctaacata    300

ataagaggct ggatttttgg tactacttta gattcgaaga cccagtccct acttattgtt    360

aataacgcta ctaatgttgt tattaaagtc tgtgaatttc aattttgtaa tgatccattt    420

ttgggtgttt attaccacaa aaacaacaaa agttggatgg aaagtgagtt cagagtttat    480

tctagtgcga ataattgcac ttttgaatat gtctctcagc cttttcttat ggaccttgaa    540

ggaaaacagg gtaatttcaa aaatcttagg gaatttgtgt ttaagaatat tgatggttat    600

tttaaaatat attctaagca cacgcctatt aatttagtgc gtgatctccc tcagggtttt    660

tcggctttag aaccattggt agatttgcca ataggtatta acatcactag gtttcaaact    720

ttacttgctt tacatagaag ttatttgact cctggtgatt cttcttcagg ttggacagct    780

ggtgctgcag cttattatgt gggttatctt caacctagga cttttctatt aaaatataat    840

gaaaatggaa ccattacaga tgctgtagac tgtgcacttg accctctctc agaaacaaag    900

tgtacgttga aatccttcac tgtagaaaaa ggaatctatc aaacttctaa ctttagagtc    960
```

-continued

```
caaccaacag aatctattgt tagatttcct aatattacaa acttgtgccc ttttggtgaa   1020
gtttttaacg ccaccagatt tgcatctgtt tatgcttgga acaggaagag aatcagcaac   1080
tgtgttgctg attattctgt cctatataat tccgcatcat tttccacttt taagtgttat   1140
ggagtgtctc ctactaaatt aaatgatctc tgctttacta atgtctatgc agattcattt   1200
gtaattagag gtgatgaagt cagacaaatc gctccagggc aaactggaaa gattgctgat   1260
tataattata aattaccaga tgattttaca ggctgcgtta tagcttggaa ttctaacaat   1320
cttgattcta aggttggtgg taattataat tacctgtata gattgtttag gaagtctaat   1380
ctcaaacctt ttgagagaga tatttcaact gaaatctatc aggccggtag cacaccttgt   1440
aatggtgttg aaggttttaa ttgttacttt cctttacaat catatggttt ccaacccact   1500
aatggtgttg gttaccaacc atacagagta gtagtacttt cttttgaact tctacatgca   1560
ccagcaactg tttgtggacc taaaaagtct actaatttgg ttaaaaacaa atgtgtcaat   1620
ttcaacttca atggtttaac aggcacaggt gttcttactg agtctaacaa aaagtttctg   1680
cctttccaac aatttggcag agacattgct gacactactg atgctgtccg tgatccacag   1740
acacttgaga ttcttgacat tacaccatgt tcttttggtg gtgtcagtgt tataacacca   1800
ggaacaaata cttctaacca ggttgctgtt ctttatcagg atgttaactg cacagaagtc   1860
cctgttgcta ttcatgcaga tcaacttact cctacttggc gtgtttattc tacaggttct   1920
aatgtttttc aaacacgtgc aggctgttta ataggggctg aacatgtcaa caactcatat   1980
gagtgtgaca tacccattgg tgcaggtata tgcgctagtt atcagactca gactaattct   2040
cctcggcggg cacgtagtgt agctagtcaa tccatcattg cctacactat gtcacttggt   2100
gcagaaaatt cagttgctta ctctaataac tctattgcca tacccacaaa ttttactatt   2160
agtgttacca cagaaattct accagtgtct atgaccaaga catcagtaga ttgtacaatg   2220
tacatttgtg gtgattcaac tgaatgcagc aatcttttgt tgcaatatgg cagtttttgt   2280
acacaattaa accgtgcttt aactggaata gctgttgaac aagacaaaaa cacccaagaa   2340
gtttttgcac aagtcaaaca aatttacaaa acaccaccaa ttaaagattt tggtggtttt   2400
aatttttcac aaatattacc agatccatca aaaccaagca agaggtcatt tattgaagat   2460
ctacttttca acaaagtgac acttgcagat gctggcttca tcaaacaata tggtgattgc   2520
cttggtgata ttgctgctag agacctcatt tgtgcacaaa agtttaacgg ccttactgtt   2580
ttgccacctt tgctcacaga tgaaatgatt gctcaataca cttctgcact gttagcgggt   2640
acaatcactt ctggttggac ctttggtgca ggtgctgcat tacaaatacc atttgctatg   2700
caaatggctt ataggtttaa tggtattgga gttacacaga atgttctcta tgagaaccaa   2760
aaattgattg ccaaccaatt taatagtgct attggcaaaa ttcaagactc actttcttcc   2820
acagcaagtg cacttggaaa acttcaagat gtggtcaacc aaaatgcaca agctttaaac   2880
acgcttgtta aacaacttag ctccaatttt ggtgcaattt caagtgtttt aaatgatatc   2940
ctttcacgtc ttgacaaagt tgaggctgaa gtgcaaattg ataggttgat cacaggcaga   3000
cttcaaagtt tgcagacata tgtgactcaa caattaatta gagctgcaga aatcagagct   3060
tctgctaatc ttgctgctac taaaatgtca gagtgtgtac ttggacaatc aaaaagagtt   3120
gatttttgtg gaaagggcta tcatcttatg tccttccctc agtcagcacc tcatggtgta   3180
gtcttcttgc atgtgactta tgtccctgca caagaaaaga acttcacaac tgctcctgcc   3240
atttgtcatg atggaaaagc acactttcct cgtgaaggtg tctttgtttc aaatggcaca   3300
cactggtttg taacacaaag gaatttttat gaaccacaaa tcattactac agacaacaca   3360
```

tttgtgtctg gtaactgtga tgttgtaata ggaattgtca acaacacagt ttatgatcct 3420
ttgcaacctg aattagactc attcaaggag gagttagata aatattttaa gaatcataca 3480
tcaccagatg ttgatttagg tgacatctct ggcattaatg cttcagttgt aaacattcaa 3540
aaagaaattg accgcctcaa tgaggttgcc aagaatttaa atgaatctct catcgatctc 3600
caagaacttg gaaagtatga gcagtatata aaatggccat ggtacatttg gctaggtttt 3660
atagctggct tgattgccat agtaatggtg acaattatgc tttgctgtat gaccagttgc 3720
tgtagttgtc tcaagggctg ttgttcttgt ggatcctgct gcaaatttga tgaagacgac 3780
tctgagccag tgctcaaagg agtcaaatta cattacacat aa 3822

<210> SEQ ID NO 3
<211> LENGTH: 194
<212> TYPE: PRT
<213> ORGANISM: Artificial Sequence
<220> FEATURE:
<223> OTHER INFORMATION: SARS-CoV-2 S RBD, modified

<400> SEQUENCE: 3

Ala Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Cys Phe Thr Asn
    50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Leu Phe Arg Lys
        115                 120                 125

Ser Asn Leu Lys Pro Phe Glu Arg Asp Ile Ser Thr Glu Ile Tyr Gln
    130                 135                 140

Ala Gly Ser Thr Pro Cys Asn Gly Val Glu Gly Phe Asn Cys Tyr Phe
145                 150                 155                 160

Pro Leu Gln Ser Tyr Gly Phe Gln Pro Thr Asn Gly Val Gly Tyr Gln
                165                 170                 175

Pro Tyr Arg Val Val Val Leu Ser Phe Glu Leu Leu His Ala Pro Ala
            180                 185                 190

Thr Val

<210> SEQ ID NO 4
<211> LENGTH: 582
<212> TYPE: DNA
<213> ORGANISM: Artificial Sequence
<220> FEATURE:
<223> OTHER INFORMATION: SARS-CoV-2 S RBD, modified

<400> SEQUENCE: 4
gccatcacca atctgtgccc ttttggcgag gtgttcaacg ccaccagatt cgcctctgtg 60
tacgcctgga accggaagcg gatcagcaat tgcgttgccg actacagcgt gctgtacaac 120

```
tctgccagct tctccacctt caagtgctat ggcgtgtctc ctaccaagct gaacgacctg    180

tgcttcacca acgtgtacgc tgacagcttc gtgatcagag gcgacgaagt gagacagatt    240

gctcctggac agacaggcaa gattgccgat tacaactaca agctccctga cgacttcaca    300

ggctgtgtga ttgcctggaa cagcaacaac ctggacagca aagtcggagg taactacaac    360

tacctgtaca ggctgtttcg gaagtccaac ctgaagcctt tcgagagaga catcagcacc    420

gagatctatc aggcaggcag cacaccttgc aatggcgtgg aaggcttcaa ctgctacttc    480

ccactgcagt cctacggctt ccagcctaca aatggagtgg gctaccagcc ttacagagtg    540

gtggtgctga gcttcgagct gctgcatgct cctgccacag tg                       582


<210> SEQ ID NO 5
<211> LENGTH: 231
<212> TYPE: PRT
<213> ORGANISM: Artificial Sequence
<220> FEATURE:
<223> OTHER INFORMATION: SARS-CoV-2 S protein S1 domain, partial,
      modified

<400> SEQUENCE: 5

Arg Val Gln Pro Thr Glu Ser Ile Val Arg Phe Pro Ala Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe Asn
    210                 215                 220

Phe Asn Gly Leu Thr Gly Thr
225                 230


<210> SEQ ID NO 6
<211> LENGTH: 693
<212> TYPE: DNA
<213> ORGANISM: Artificial Sequence
<220> FEATURE:
<223> OTHER INFORMATION: SARS-CoV-2 S protein S1 domain, partial,
```

modified

<400> SEQUENCE: 6

```
agagtgcagc ccacagagtc tatcgtgcgg ttccctgcca tcaccaatct gtgccctttt      60

ggcgaggtgt tcaacgccac cagattcgcc tctgtgtacg cctggaaccg gaagcggatc     120

agcaattgcg ttgccgacta cagcgtgctg tacaactctg ccagcttctc caccttcaag     180

tgctatggcg tgtctcctac caagctgaac gacctgtgct tcaccaacgt gtacgctgac     240

agcttcgtga tcagaggcga cgaagtgaga cagattgctc ctggacagac aggcaagatt     300

gccgattaca actacaagct ccctgacgac ttcacaggct gtgtgattgc ctggaacagc     360

aacaacctgg acagcaaagt cggaggtaac tacaactacc tgtacaggct gtttcggaag     420

tccaacctga agcctttcga gagagacatc agcaccgaga tctatcaggc aggcagcaca     480

ccttgcaatg gcgtggaagg cttcaactgc tacttcccac tgcagtccta cggcttccag     540

cctacaaatg gagtgggcta ccagccttac agagtggtgg tgctgagctt cgagctgctg     600

catgctcctg ccacagtgtg cggacctaag aaaagcacca acctggtgaa gaacaaatgc     660

gtgaacttca acttcaatgg cctgacaggc acc                                  693
```

<210> SEQ ID NO 7
<211> LENGTH: 19
<212> TYPE: PRT
<213> ORGANISM: Artificial Sequence
<220> FEATURE:
<223> OTHER INFORMATION: Human IgGH signal peptide

<400> SEQUENCE: 7

```
Met Glu Phe Gly Leu Ser Trp Val Phe Leu Val Ala Ile Leu Lys Gly
1               5                   10                  15

Val Gln Cys
```

<210> SEQ ID NO 8
<211> LENGTH: 57
<212> TYPE: DNA
<213> ORGANISM: Artificial Sequence
<220> FEATURE:
<223> OTHER INFORMATION: Human IgGH signal peptide

<400> SEQUENCE: 8

```
atggaattcg gactgagctg ggtgttcctg gtcgccattc tgaaaggcgt gcagtgc         57
```

<210> SEQ ID NO 9
<211> LENGTH: 250
<212> TYPE: PRT
<213> ORGANISM: Artificial Sequence
<220> FEATURE:
<223> OTHER INFORMATION: SARS-CoV-2 S protein S1 domain, partial, modified plus human IgGH signal peptide ("SARS-2 S-RBD-1")

<400> SEQUENCE: 9

```
Met Glu Phe Gly Leu Ser Trp Val Phe Leu Val Ala Ile Leu Lys Gly
1               5                   10                  15

Val Gln Cys Arg Val Gln Pro Thr Glu Ser Ile Val Arg Phe Pro Ala
            20                  25                  30

Ile Thr Asn Leu Cys Pro Phe Gly Glu Val Phe Asn Ala Thr Arg Phe
        35                  40                  45

Ala Ser Val Tyr Ala Trp Asn Arg Lys Arg Ile Ser Asn Cys Val Ala
    50                  55                  60

Asp Tyr Ser Val Leu Tyr Asn Ser Ala Ser Phe Ser Thr Phe Lys Cys
```

```
65                  70                  75                  80

Tyr Gly Val Ser Pro Thr Lys Leu Asn Asp Leu Cys Phe Thr Asn Val
                85                  90                  95

Tyr Ala Asp Ser Phe Val Ile Arg Gly Asp Glu Val Arg Gln Ile Ala
            100                 105                 110

Pro Gly Gln Thr Gly Lys Ile Ala Asp Tyr Asn Tyr Lys Leu Pro Asp
        115                 120                 125

Asp Phe Thr Gly Cys Val Ile Ala Trp Asn Ser Asn Asn Leu Asp Ser
    130                 135                 140

Lys Val Gly Gly Asn Tyr Asn Tyr Leu Tyr Arg Leu Phe Arg Lys Ser
145                 150                 155                 160

Asn Leu Lys Pro Phe Glu Arg Asp Ile Ser Thr Glu Ile Tyr Gln Ala
                165                 170                 175

Gly Ser Thr Pro Cys Asn Gly Val Glu Gly Phe Asn Cys Tyr Phe Pro
            180                 185                 190

Leu Gln Ser Tyr Gly Phe Gln Pro Thr Asn Gly Val Gly Tyr Gln Pro
        195                 200                 205

Tyr Arg Val Val Val Leu Ser Phe Glu Leu Leu His Ala Pro Ala Thr
    210                 215                 220

Val Cys Gly Pro Lys Lys Ser Thr Asn Leu Val Lys Asn Lys Cys Val
225                 230                 235                 240

Asn Phe Asn Phe Asn Gly Leu Thr Gly Thr
                245                 250


<210> SEQ ID NO 10
<211> LENGTH: 756
<212> TYPE: DNA
<213> ORGANISM: Artificial Sequence
<220> FEATURE:
<223> OTHER INFORMATION: SARS-CoV-2 S protein S1 domain, partial,
      modified plus human IgGH signal peptide ("SARS-2 S-RBD-1")

<400> SEQUENCE: 10

atggaattcg gactgagctg ggtgttcctg gtcgccattc tgaaaggcgt gcagtgcaga      60

gtgcagccca cagagtctat cgtgcggttc cctgccatca ccaatctgtg cccttttggc     120

gaggtgttca acgccaccag attcgcctct gtgtacgcct ggaaccggaa gcggatcagc     180

aattgcgttg ccgactacag cgtgctgtac aactctgcca gcttctccac cttcaagtgc     240

tatggcgtgt ctcctaccaa gctgaacgac ctgtgcttca ccaacgtgta cgctgacagc     300

ttcgtgatca gaggcgacga agtgagacag attgctcctg gacagacagg caagattgcc     360

gattacaact acaagctccc tgacgacttc acaggctgtg tgattgcctg gaacagcaac     420

aacctggaca gcaaagtcgg aggtaactac aactacctgt acaggctgtt tcggaagtcc     480

aacctgaagc ctttcgagag agacatcagc accgagatct atcaggcagg cagcacacct     540

tgcaatggcg tggaaggctt caactgctac ttcccactgc agtcctacgg cttccagcct     600

acaaatggag tgggctacca gccttacaga gtggtggtgc tgagcttcga gctgctgcat     660

gctcctgcca cagtgtgcgg acctaagaaa agcaccaacc tggtgaagaa caaatgcgtg     720

aacttcaact tcaatggcct gacaggcacc tgataa                               756


<210> SEQ ID NO 11
<211> LENGTH: 275
<212> TYPE: PRT
<213> ORGANISM: SARS coronavirus
<220> FEATURE:
<223> OTHER INFORMATION: SARS-CoV-2 protein 3a, full-length
```

```
<400> SEQUENCE: 11

Met Asp Leu Phe Met Arg Ile Phe Thr Ile Gly Thr Val Thr Leu Lys
1               5                   10                  15

Gln Gly Glu Ile Lys Asp Ala Thr Pro Ser Asp Phe Val Arg Ala Thr
            20                  25                  30

Ala Thr Ile Pro Ile Gln Ala Ser Leu Pro Phe Gly Trp Leu Ile Val
        35                  40                  45

Gly Val Ala Leu Leu Ala Val Phe Gln Ser Ala Ser Lys Ile Ile Thr
    50                  55                  60

Leu Lys Lys Arg Trp Gln Leu Ala Leu Ser Lys Gly Val His Phe Val
65                  70                  75                  80

Cys Asn Leu Leu Leu Leu Phe Val Thr Val Tyr Ser His Leu Leu Leu
                85                  90                  95

Val Ala Ala Gly Leu Glu Ala Pro Phe Leu Tyr Leu Tyr Ala Leu Val
            100                 105                 110

Tyr Phe Leu Gln Ser Ile Asn Phe Val Arg Ile Ile Met Arg Leu Trp
        115                 120                 125

Leu Cys Trp Lys Cys Arg Ser Lys Asn Pro Leu Leu Tyr Asp Ala Asn
    130                 135                 140

Tyr Phe Leu Cys Trp His Thr Asn Cys Tyr Asp Tyr Cys Ile Pro Tyr
145                 150                 155                 160

Asn Ser Val Thr Ser Ser Ile Val Ile Thr Ser Gly Asp Gly Thr Thr
                165                 170                 175

Ser Pro Ile Ser Glu His Asp Tyr Gln Ile Gly Gly Tyr Thr Glu Lys
            180                 185                 190

Trp Glu Ser Gly Val Lys Asp Cys Val Val Leu His Ser Tyr Phe Thr
        195                 200                 205

Ser Asp Tyr Tyr Gln Leu Tyr Ser Thr Gln Leu Ser Thr Asp Thr Gly
    210                 215                 220

Val Glu His Val Thr Phe Phe Ile Tyr Asn Lys Ile Val Asp Glu Pro
225                 230                 235                 240

Glu Glu His Val Gln Ile His Thr Ile Asp Gly Ser Ser Gly Val Val
                245                 250                 255

Asn Pro Val Met Glu Pro Ile Tyr Asp Glu Pro Thr Thr Thr Thr Ser
            260                 265                 270

Val Pro Leu
        275


<210> SEQ ID NO 12
<211> LENGTH: 75
<212> TYPE: PRT
<213> ORGANISM: SARS coronavirus
<220> FEATURE:
<223> OTHER INFORMATION: SARS-CoV-2 protein E, full-length

<400> SEQUENCE: 12

Met Tyr Ser Phe Val Ser Glu Glu Thr Gly Thr Leu Ile Val Asn Ser
1               5                   10                  15

Val Leu Leu Phe Leu Ala Phe Val Val Phe Leu Leu Val Thr Leu Ala
            20                  25                  30

Ile Leu Thr Ala Leu Arg Leu Cys Ala Tyr Cys Cys Asn Ile Val Asn
        35                  40                  45

Val Ser Leu Val Lys Pro Ser Phe Tyr Val Tyr Ser Arg Val Lys Asn
    50                  55                  60
```

```
Leu Asn Ser Ser Arg Val Pro Asp Leu Leu Val
65                  70                  75


<210> SEQ ID NO 13
<211> LENGTH: 222
<212> TYPE: PRT
<213> ORGANISM: SARS coronavirus
<220> FEATURE:
<223> OTHER INFORMATION: SARS-CoV-2 protein M, full-length

<400> SEQUENCE: 13

Met Ala Asp Ser Asn Gly Thr Ile Thr Val Glu Glu Leu Lys Lys Leu
1               5                   10                  15

Leu Glu Gln Trp Asn Leu Val Ile Gly Phe Leu Phe Leu Thr Trp Ile
            20                  25                  30

Cys Leu Leu Gln Phe Ala Tyr Ala Asn Arg Asn Arg Phe Leu Tyr Ile
        35                  40                  45

Ile Lys Leu Ile Phe Leu Trp Leu Leu Trp Pro Val Thr Leu Ala Cys
    50                  55                  60

Phe Val Leu Ala Ala Val Tyr Arg Ile Asn Trp Ile Thr Gly Gly Ile
65                  70                  75                  80

Ala Ile Ala Met Ala Cys Leu Val Gly Leu Met Trp Leu Ser Tyr Phe
                85                  90                  95

Ile Ala Ser Phe Arg Leu Phe Ala Arg Thr Arg Ser Met Trp Ser Phe
            100                 105                 110

Asn Pro Glu Thr Asn Ile Leu Leu Asn Val Pro Leu His Gly Thr Ile
        115                 120                 125

Leu Thr Arg Pro Leu Leu Glu Ser Glu Leu Val Ile Gly Ala Val Ile
    130                 135                 140

Leu Arg Gly His Leu Arg Ile Ala Gly His His Leu Gly Arg Cys Asp
145                 150                 155                 160

Ile Lys Asp Leu Pro Lys Glu Ile Thr Val Ala Thr Ser Arg Thr Leu
                165                 170                 175

Ser Tyr Tyr Lys Leu Gly Ala Ser Gln Arg Val Ala Gly Asp Ser Gly
            180                 185                 190

Phe Ala Ala Tyr Ser Arg Tyr Arg Ile Gly Asn Tyr Lys Leu Asn Thr
        195                 200                 205

Asp His Ser Ser Ser Ser Asp Asn Ile Ala Leu Leu Val Gln
    210                 215                 220


<210> SEQ ID NO 14
<211> LENGTH: 28
<212> TYPE: PRT
<213> ORGANISM: Artificial Sequence
<220> FEATURE:
<223> OTHER INFORMATION: SARS-CoV-2 protein 3a-1 fragment

<400> SEQUENCE: 14

Phe Gln Ser Ala Ser Lys Ile Ile Thr Leu Lys Lys Arg Trp Gln Leu
1               5                   10                  15

Ala Leu Ser Lys Gly Val His Phe Val Cys Asn Leu
            20                  25


<210> SEQ ID NO 15
<211> LENGTH: 98
<212> TYPE: PRT
<213> ORGANISM: Artificial Sequence
<220> FEATURE:
<223> OTHER INFORMATION: SARS CoV-2 protein 3a-2 fragment
```

<400> SEQUENCE: 15

```
Pro Ile Ser Glu His Asp Tyr Gln Ile Gly Gly Tyr Thr Glu Lys Trp
1               5                   10                  15

Glu Ser Gly Val Lys Asp Cys Val Val Leu His Ser Tyr Phe Thr Ser
            20                  25                  30

Asp Tyr Tyr Gln Leu Tyr Ser Thr Gln Leu Ser Thr Asp Thr Gly Val
        35                  40                  45

Glu His Val Thr Phe Phe Ile Tyr Asn Lys Ile Val Asp Glu Pro Glu
    50                  55                  60

Glu His Val Gln Ile His Thr Ile Asp Gly Ser Ser Gly Val Val Asn
65                  70                  75                  80

Pro Val Met Glu Pro Ile Tyr Asp Glu Pro Thr Thr Thr Thr Ser Val
                85                  90                  95

Pro Leu
```

<210> SEQ ID NO 16
<211> LENGTH: 36
<212> TYPE: PRT
<213> ORGANISM: Artificial Sequence
<220> FEATURE:
<223> OTHER INFORMATION: SARS-CoV-2 protein E fragment

<400> SEQUENCE: 16

```
Arg Leu Cys Ala Tyr Cys Cys Asn Ile Val Asn Val Ser Leu Val Lys
1               5                   10                  15

Pro Ser Phe Tyr Val Tyr Ser Arg Val Lys Asn Leu Asn Ser Ser Arg
            20                  25                  30

Val Pro Asp Leu
        35
```

<210> SEQ ID NO 17
<211> LENGTH: 15
<212> TYPE: PRT
<213> ORGANISM: Artificial Sequence
<220> FEATURE:
<223> OTHER INFORMATION: SARS-CoV-2 protein M-1 fragment

<400> SEQUENCE: 17

```
Phe Ala Tyr Ala Asn Arg Asn Arg Phe Leu Tyr Ile Ile Lys Leu
1               5                   10                  15
```

<210> SEQ ID NO 18
<211> LENGTH: 119
<212> TYPE: PRT
<213> ORGANISM: Artificial Sequence
<220> FEATURE:
<223> OTHER INFORMATION: SARS-CoV-2 protein M-2 fragment

<400> SEQUENCE: 18

```
Ser Tyr Phe Ile Ala Ser Phe Arg Leu Phe Ala Arg Thr Arg Ser Met
1               5                   10                  15

Trp Ser Phe Asn Pro Glu Thr Asn Ile Leu Leu Asn Val Pro Leu His
            20                  25                  30

Gly Thr Ile Leu Thr Arg Pro Leu Leu Glu Ser Glu Leu Val Ile Gly
        35                  40                  45

Ala Val Ile Leu Arg Gly His Leu Arg Ile Ala Gly His His Leu Gly
    50                  55                  60

Arg Cys Asp Ile Lys Asp Leu Pro Lys Glu Ile Thr Val Ala Thr Ser
65                  70                  75                  80
```

```
Arg Thr Leu Ser Tyr Tyr Lys Leu Gly Ala Ser Gln Arg Val Ala Gly
                85                  90                  95

Asp Ser Gly Phe Ala Ala Tyr Ser Arg Tyr Arg Ile Gly Asn Tyr Lys
            100                 105                 110

Leu Asn Thr Asp His Ser Ser
        115


<210> SEQ ID NO 19
<211> LENGTH: 297
<212> TYPE: PRT
<213> ORGANISM: Artificial Sequence
<220> FEATURE:
<223> OTHER INFORMATION: SARS-CoV-2 protein 3a-1, 3a-2, E, M-1, M-2
      fragments, fused

<400> SEQUENCE: 19

Met Phe Gln Ser Ala Ser Lys Ile Ile Thr Leu Lys Lys Arg Trp Gln
1               5                   10                  15

Leu Ala Leu Ser Lys Gly Val His Phe Val Cys Asn Leu Pro Ile Ser
            20                  25                  30

Glu His Asp Tyr Gln Ile Gly Gly Tyr Thr Glu Lys Trp Glu Ser Gly
        35                  40                  45

Val Lys Asp Cys Val Val Leu His Ser Tyr Phe Thr Ser Asp Tyr Tyr
    50                  55                  60

Gln Leu Tyr Ser Thr Gln Leu Ser Thr Asp Thr Gly Val Glu His Val
65                  70                  75                  80

Thr Phe Phe Ile Tyr Asn Lys Ile Val Asp Glu Pro Glu Glu His Val
                85                  90                  95

Gln Ile His Thr Ile Asp Gly Ser Ser Gly Val Val Asn Pro Val Met
            100                 105                 110

Glu Pro Ile Tyr Asp Glu Pro Thr Thr Thr Thr Ser Val Pro Leu Arg
        115                 120                 125

Leu Cys Ala Tyr Cys Cys Asn Ile Val Asn Val Ser Leu Val Lys Pro
    130                 135                 140

Ser Phe Tyr Val Tyr Ser Arg Val Lys Asn Leu Asn Ser Ser Arg Val
145                 150                 155                 160

Pro Asp Leu Phe Ala Tyr Ala Asn Arg Asn Arg Phe Leu Tyr Ile Ile
                165                 170                 175

Lys Leu Ser Tyr Phe Ile Ala Ser Phe Arg Leu Phe Ala Arg Thr Arg
            180                 185                 190

Ser Met Trp Ser Phe Asn Pro Glu Thr Asn Ile Leu Leu Asn Val Pro
        195                 200                 205

Leu His Gly Thr Ile Leu Thr Arg Pro Leu Leu Glu Ser Glu Leu Val
    210                 215                 220

Ile Gly Ala Val Ile Leu Arg Gly His Leu Arg Ile Ala Gly His His
225                 230                 235                 240

Leu Gly Arg Cys Asp Ile Lys Asp Leu Pro Lys Glu Ile Thr Val Ala
                245                 250                 255

Thr Ser Arg Thr Leu Ser Tyr Tyr Lys Leu Gly Ala Ser Gln Arg Val
            260                 265                 270

Ala Gly Asp Ser Gly Phe Ala Ala Tyr Ser Arg Tyr Arg Ile Gly Asn
        275                 280                 285

Tyr Lys Leu Asn Thr Asp His Ser Ser
    290                 295


<210> SEQ ID NO 20
```

```
<211> LENGTH: 297
<212> TYPE: PRT
<213> ORGANISM: Artificial Sequence
<220> FEATURE:
<223> OTHER INFORMATION: SARS-CoV-2 3aEM fusion protein, modified
      ("SARS-2 3aEM-1")

<400> SEQUENCE: 20

Met Phe Gln Ser Ala Ser Lys Ile Ile Thr Leu Lys Lys Arg Trp Gln
1               5                   10                  15

Leu Ala Leu Ser Lys Gly Val His Phe Val Cys Asn Leu Pro Ile Ser
            20                  25                  30

Glu His Asp Tyr Gln Ile Gly Gly Tyr Thr Glu Lys Trp Glu Ser Gly
        35                  40                  45

Val Lys Asp Cys Val Val Leu His Ser Tyr Phe Thr Ser Asp Tyr Tyr
    50                  55                  60

Gln Leu Tyr Ser Thr Gln Leu Ser Thr Asp Thr Gly Val Glu His Val
65                  70                  75                  80

Thr Phe Phe Ile Tyr Asn Lys Ile Val Asp Glu Pro Glu Glu His Val
                85                  90                  95

Gln Ile His Thr Ile Asp Gly Ser Ser Gly Val Val Asn Pro Val Met
            100                 105                 110

Glu Pro Ile Tyr Asp Glu Pro Thr Thr Thr Thr Ser Val Pro Leu Arg
        115                 120                 125

Leu Cys Trp Phe Cys Cys Asn Ile Val Asn Val Ser Leu Val Lys Pro
    130                 135                 140

Ser Phe Tyr Val Tyr Ser Arg Val Lys Asn Leu Asn Ser Ser Arg Val
145                 150                 155                 160

Pro Asp Leu Phe Ala Tyr Ala Asn Arg Asn Arg Phe Leu Tyr Ile Ile
                165                 170                 175

Lys Leu Asp Phe Phe Ile Ala Ser Phe Arg Leu Phe Ala Arg Thr Arg
            180                 185                 190

Ser Met Trp Ser Phe Asn Pro Glu Thr Asn Ile Leu Leu Asn Val Pro
        195                 200                 205

Leu His Gly Thr Ile Leu Thr Arg Pro Leu Leu Glu Ser Glu Leu Val
    210                 215                 220

Ile Gly Ala Val Ile Leu Arg Gly His Leu Arg Ile Ala Gly His His
225                 230                 235                 240

Leu Gly Arg Cys Asp Ile Lys Asp Leu Pro Lys Glu Ile Thr Val Ala
                245                 250                 255

Thr Ser Arg Thr Leu Ser Tyr Tyr Lys Leu Gly Ala Ser Gln Arg Val
            260                 265                 270

Ala Gly Asp Ser Gly Phe Ala Ala Tyr Ser Arg Tyr Arg Ile Gly Asn
        275                 280                 285

Tyr Lys Leu Asn Thr Asp His Ser Ser
    290                 295


<210> SEQ ID NO 21
<211> LENGTH: 897
<212> TYPE: DNA
<213> ORGANISM: Artificial Sequence
<220> FEATURE:
<223> OTHER INFORMATION: SARS-CoV-2 3aEM fusion protein, modified
      ("SARS-2 3aEM-1")

<400> SEQUENCE: 21

atgtttcagt ctgccagcaa gatcatcacc ctgaagaaga ggtggcagct ggctctgtct      60
```

```
aaaggtgtgc acttcgtgtg caacctgcct atcagcgagc acgactatca gatcggaggc    120

tacaccgaga agtgggagtc tggcgtgaag gactgtgtgg tgctgcacag ctacttcacc    180

agcgactact accagctgta ctctacccag ctgagcaccg acacaggcgt ggaacacgtg    240

accttcttca tctacaacaa gatcgtggac gaacccgaag aacacgtgca gatccacaca    300

atcgatggca gctctggcgt ggtcaaccca gtgatggaac ccatctacga cgagcctacc    360

accaccacaa gcgtgcctct gagactgtgc tggttctgct gcaacatcgt gaacgtgtcc    420

ctggtcaagc ccagcttcta cgtgtacagc agagtgaaga acctgaacag cagcagggtt    480

cccgacctgt tcgcctacgc caacagaaac agattcctgt acatcatcaa gctggatttc    540

ttcatcgcca gcttcagact gttcgcacgg accagatcca tgtggtcctt caatcccgag    600

acaaacatcc tgctgaatgt gcctctgcac ggcaccatcc tgacaagacc tctgctggaa    660

agcgagctgg ttatcggtgc cgtgatcctg agaggccacc tgagaattgc aggacaccac    720

ctgggcagat gcgacatcaa ggacctgcca aaagaaatca ccgtggccac cagcaggacc    780

ctgagctact acaagctggg agcctctcag agagtggctg gcgattctgg atttgcagcc    840

tacagcagat accggatcgg caactacaaa ctgaataccg accacagcag ctaatga      897
```

<210> SEQ ID NO 22
<211> LENGTH: 1261
<212> TYPE: PRT
<213> ORGANISM: Artificial Sequence
<220> FEATURE:
<223> OTHER INFORMATION: SARS-CoV-2 S protein, full-length, modified, minus signal peptide

<400> SEQUENCE: 22

```
Ser Gln Cys Val Asn Leu Thr Thr Arg Thr Gln Leu Pro Pro Ala Tyr
1               5                   10                  15

Thr Asn Ser Phe Thr Arg Gly Val Tyr Tyr Pro Asp Lys Val Phe Arg
            20                  25                  30

Ser Ser Val Leu His Ser Thr Gln Asp Leu Phe Leu Pro Phe Phe Ser
        35                  40                  45

Asn Val Thr Trp Phe His Ala Ile His Val Ser Gly Thr Asn Gly Thr
    50                  55                  60

Lys Arg Phe Asp Asn Pro Val Leu Pro Phe Asn Asp Gly Val Tyr Phe
65                  70                  75                  80

Ala Ser Thr Glu Lys Ser Asn Ile Ile Arg Gly Trp Ile Phe Gly Thr
                85                  90                  95

Thr Leu Asp Ser Lys Thr Gln Ser Leu Leu Ile Val Asn Asn Ala Thr
            100                 105                 110

Asn Val Val Ile Lys Val Cys Glu Phe Gln Phe Cys Asn Asp Pro Phe
        115                 120                 125

Leu Gly Val Tyr Tyr His Lys Asn Asn Lys Ser Trp Met Glu Ser Glu
    130                 135                 140

Phe Arg Val Tyr Ser Ser Ala Asn Asn Cys Thr Phe Glu Tyr Val Ser
145                 150                 155                 160

Gln Pro Phe Leu Met Asp Leu Glu Gly Lys Gln Gly Asn Phe Lys Asn
                165                 170                 175

Leu Arg Glu Phe Val Phe Lys Asn Ile Asp Gly Tyr Phe Lys Ile Tyr
            180                 185                 190

Ser Lys His Thr Pro Ile Asn Leu Val Arg Asp Leu Pro Gln Gly Phe
        195                 200                 205

Ser Ala Leu Glu Pro Leu Val Asp Leu Pro Ile Gly Ile Asn Ile Thr
```

-continued

```
    210                 215                 220

Arg Phe Gln Thr Leu Leu Ala Leu His Arg Ser Tyr Leu Thr Pro Gly
225                 230                 235                 240

Asp Ser Ser Ser Gly Trp Thr Ala Gly Ala Ala Ala Tyr Tyr Val Gly
                245                 250                 255

Tyr Leu Gln Pro Arg Thr Phe Leu Leu Lys Tyr Asn Glu Asn Gly Thr
            260                 265                 270

Ile Thr Asp Ala Val Asp Cys Ala Leu Asp Pro Leu Ser Glu Thr Lys
        275                 280                 285

Cys Thr Leu Lys Ser Phe Thr Val Glu Lys Gly Ile Tyr Gln Thr Ser
    290                 295                 300

Asn Phe Arg Val Gln Pro Thr Glu Ser Ile Val Arg Phe Pro Asn Ile
305                 310                 315                 320

Thr Asn Leu Cys Pro Phe Gly Glu Val Phe Asn Ala Thr Arg Phe Ala
                325                 330                 335

Ser Val Tyr Ala Trp Asn Arg Lys Arg Ile Ser Asn Cys Val Ala Asp
            340                 345                 350

Tyr Ser Val Leu Tyr Asn Ser Ala Ser Phe Ser Thr Phe Lys Cys Tyr
        355                 360                 365

Gly Val Ser Pro Thr Lys Leu Asn Asp Leu Cys Phe Thr Asn Val Tyr
    370                 375                 380

Ala Asp Ser Phe Val Ile Arg Gly Asp Glu Val Arg Gln Ile Ala Pro
385                 390                 395                 400

Gly Gln Thr Gly Lys Ile Ala Asp Tyr Asn Tyr Lys Leu Pro Asp Asp
                405                 410                 415

Phe Thr Gly Cys Val Ile Ala Trp Asn Ser Asn Asn Leu Asp Ser Lys
            420                 425                 430

Val Gly Gly Asn Tyr Asn Tyr Leu Tyr Arg Leu Phe Arg Lys Ser Asn
        435                 440                 445

Leu Lys Pro Phe Glu Arg Asp Ile Ser Thr Glu Ile Tyr Gln Ala Gly
    450                 455                 460

Ser Thr Pro Cys Asn Gly Val Glu Gly Phe Asn Cys Tyr Phe Pro Leu
465                 470                 475                 480

Gln Ser Tyr Gly Phe Gln Pro Thr Asn Gly Val Gly Tyr Gln Pro Tyr
                485                 490                 495

Arg Val Val Val Leu Ser Phe Glu Leu Leu His Ala Pro Ala Thr Val
            500                 505                 510

Cys Gly Pro Lys Lys Ser Thr Asn Leu Val Lys Asn Lys Cys Val Asn
        515                 520                 525

Phe Asn Phe Asn Gly Leu Thr Gly Thr Gly Val Leu Thr Glu Ser Asn
    530                 535                 540

Lys Lys Phe Leu Pro Phe Gln Gln Phe Gly Arg Asp Ile Ala Asp Thr
545                 550                 555                 560

Thr Asp Ala Val Arg Asp Pro Gln Thr Leu Glu Ile Leu Asp Ile Thr
                565                 570                 575

Pro Cys Ser Phe Gly Gly Val Ser Val Ile Thr Pro Gly Thr Asn Thr
            580                 585                 590

Ser Asn Gln Val Ala Val Leu Tyr Gln Asp Val Asn Cys Thr Glu Val
        595                 600                 605

Pro Val Ala Ile His Ala Asp Gln Leu Thr Pro Thr Trp Arg Val Tyr
    610                 615                 620

Ser Thr Gly Ser Asn Val Phe Gln Thr Arg Ala Gly Cys Leu Ile Gly
625                 630                 635                 640
```

-continued

```
Ala Glu His Val Asn Asn Ser Tyr Glu Cys Asp Ile Pro Ile Gly Ala
                645                 650                 655

Gly Ile Cys Ala Ser Tyr Gln Thr Gln Thr Asn Ser Pro Gly Ser Ala
            660                 665                 670

Ser Ser Val Ala Ser Gln Ser Ile Ile Ala Tyr Thr Met Ser Leu Gly
        675                 680                 685

Ala Glu Asn Ser Val Ala Tyr Ser Asn Asn Ser Ile Ala Ile Pro Thr
    690                 695                 700

Asn Phe Thr Ile Ser Val Thr Thr Glu Ile Leu Pro Val Ser Met Thr
705                 710                 715                 720

Lys Thr Ser Val Asp Cys Thr Met Tyr Ile Cys Gly Asp Ser Thr Glu
                725                 730                 735

Cys Ser Asn Leu Leu Leu Gln Tyr Gly Ser Phe Cys Thr Gln Leu Asn
            740                 745                 750

Arg Ala Leu Thr Gly Ile Ala Val Glu Gln Asp Lys Asn Thr Gln Glu
        755                 760                 765

Val Phe Ala Gln Val Lys Gln Ile Tyr Lys Thr Pro Pro Ile Lys Asp
    770                 775                 780

Phe Gly Gly Phe Asn Phe Ser Gln Ile Leu Pro Asp Pro Ser Lys Pro
785                 790                 795                 800

Ser Lys Arg Ser Phe Ile Glu Asp Leu Leu Phe Asn Lys Val Thr Leu
                805                 810                 815

Ala Asp Ala Gly Phe Ile Lys Gln Tyr Gly Asp Cys Leu Gly Asp Ile
            820                 825                 830

Ala Ala Arg Asp Leu Ile Cys Ala Gln Lys Phe Asn Gly Leu Thr Val
        835                 840                 845

Leu Pro Pro Leu Leu Thr Asp Glu Met Ile Ala Gln Tyr Thr Ser Ala
    850                 855                 860

Leu Leu Ala Gly Thr Ile Thr Ser Gly Trp Thr Phe Gly Ala Gly Ala
865                 870                 875                 880

Ala Leu Gln Ile Pro Phe Ala Met Gln Met Ala Tyr Arg Phe Asn Gly
                885                 890                 895

Ile Gly Val Thr Gln Asn Val Leu Tyr Glu Asn Gln Lys Leu Ile Ala
            900                 905                 910

Asn Gln Phe Asn Ser Ala Ile Gly Lys Ile Gln Asp Ser Leu Ser Ser
        915                 920                 925

Thr Ala Ser Ala Leu Gly Lys Leu Gln Asp Val Val Asn Gln Asn Ala
    930                 935                 940

Gln Ala Leu Asn Thr Leu Val Lys Gln Leu Ser Ser Asn Phe Gly Ala
945                 950                 955                 960

Ile Ser Ser Val Leu Asn Asp Ile Leu Ser Arg Leu Asp Pro Pro Glu
                965                 970                 975

Ala Glu Val Gln Ile Asp Arg Leu Ile Thr Gly Arg Leu Gln Ser Leu
            980                 985                 990

Gln Thr Tyr Val Thr Gln Gln Leu Ile Arg Ala Ala Glu Ile Arg Ala
        995                 1000                1005

Ser Ala Asn Leu Ala Ala Thr Lys Met Ser Glu Cys Val Leu Gly Gln
    1010                1015                1020

Ser Lys Arg Val Asp Phe Cys Gly Lys Gly Tyr His Leu Met Ser Phe
1025                1030                1035                1040

Pro Gln Ser Ala Pro His Gly Val Val Phe Leu His Val Thr Tyr Val
                1045                1050                1055
```

```
Pro Ala Gln Glu Lys Asn Phe Thr Thr Ala Pro Ala Ile Cys His Asp
            1060                1065                1070

Gly Lys Ala His Phe Pro Arg Glu Gly Val Phe Val Ser Asn Gly Thr
        1075                1080                1085

His Trp Phe Val Thr Gln Arg Asn Phe Tyr Glu Pro Gln Ile Ile Thr
    1090                1095                1100

Thr Asp Asn Thr Phe Val Ser Gly Asn Cys Asp Val Val Ile Gly Ile
1105                1110                1115                1120

Val Asn Asn Thr Val Tyr Asp Pro Leu Gln Pro Glu Leu Asp Ser Phe
                1125                1130                1135

Lys Glu Glu Leu Asp Lys Tyr Phe Lys Asn His Thr Ser Pro Asp Val
            1140                1145                1150

Asp Leu Gly Asp Ile Ser Gly Ile Asn Ala Ser Val Val Asn Ile Gln
        1155                1160                1165

Lys Glu Ile Asp Arg Leu Asn Glu Val Ala Lys Asn Leu Asn Glu Ser
    1170                1175                1180

Leu Ile Asp Leu Gln Glu Leu Gly Lys Tyr Glu Gln Tyr Ile Lys Trp
1185                1190                1195                1200

Pro Trp Tyr Ile Trp Leu Gly Phe Ile Ala Gly Leu Ile Ala Ile Val
                1205                1210                1215

Met Val Thr Ile Met Leu Cys Cys Met Thr Ser Cys Cys Ser Cys Leu
            1220                1225                1230

Lys Gly Cys Cys Ser Cys Gly Ser Cys Cys Lys Phe Asp Glu Asp Asp
        1235                1240                1245

Ser Glu Pro Val Leu Lys Gly Val Lys Leu His Tyr Thr
    1250                1255                1260
```

<210> SEQ ID NO 23
<211> LENGTH: 3789
<212> TYPE: DNA
<213> ORGANISM: Artificial Sequence
<220> FEATURE:
<223> OTHER INFORMATION: SARS-CoV-2 S protein, full-length, modified, minus signal peptide

<400> SEQUENCE: 23

```
agccagtgtg tgaacctgac caccagaaca cagctgcctc cagcctacac caacagcttt      60

accagaggcg tgtactatcc cgacaaggtg ttcagatcca gcgtgctgca ctctacccag     120

gacctgttcc tgcctttctt cagcaacgtg acctggttcc acgccatcca cgtgagcggt     180

accaatggca ccaagagatt cgacaatccc gtgctgccct tcaacgacgg agtgtacttt     240

gccagcaccg agaagtccaa catcatcaga ggctggatct tcggcaccac actggacagc     300

aagacccaga gcctgctgat cgtgaacaac gccaccaacg tggtcatcaa agtgtgcgag     360

ttccagttct gcaacgatcc cttcctggga gtctactacc acaagaacaa caagagctgg     420

atggaaagcg agttcagagt gtacagctct gccaacaact gcaccttcga gtacgtgtcc     480

cagcctttcc tgatggacct ggaaggcaag cagggcaatt tcaagaatct ccgagagttc     540

gtgttcaaga acatcgacgg ctacttcaag atctacagca agcacacacc tatcaacctc     600

gtgagggatc tgcctcaggg cttctctgct ctggaacctc tggtggatct gcccatcggc     660

atcaacatca ctcggtttca gacactgctg gcactgcaca gaagctacct gacacctggc     720

gatagcagca gcggatggac agctggtgct gcagcttact atgtgggcta cctgcagcct     780

agaaccttcc tgctgaagta caacgagaac ggcaccatca ccgatgccgt ggattgtgct     840

ctggatcctc tgagcgagac aaagtgcacc ctgaagtcct tcaccgtgga gaagggcatc     900
```

```
taccagacca gcaacttcag ggtgcagccc accgaatcca tcgtgcggtt ccctaacatc    960
accaatctgt gtccctttgg cgaggtgttc aatgccacca gattcgcctc tgtgtacgcc   1020
tggaaccgga agcggatcag caattgcgtt gccgactact ccgtgctgta caactcagcc   1080
agcttcagca ccttcaagtg ctacggagtg agccctacca agctgaacga cctgtgcttc   1140
acaaacgtgt atgctgacag cttcgtgatc agaggagatg aagtgaggca gattgctcct   1200
ggacagacag gcaagattgc agattacaac tacaagctgc ctgacgactt cacaggctgt   1260
gtgattgcct ggaacagcaa caacctggac tccaaagtcg gaggcaacta caactacctg   1320
tacagactgt tcaggaagtc caatctgaag cccttcgaac gggacatctc caccgagatc   1380
tatcaggctg gcagcacacc ttgtaatgga gtggaaggct tcaactgcta cttcccactg   1440
cagtcctacg gctttcagcc cacaaatggc gtgggctatc agccctacag agtggtggtg   1500
ctgagcttcg aactgctgca tgctcctgcc acagtgtgcg gacctaagaa atccaccaat   1560
ctcgtgaaga acaaatgcgt gaacttcaac ttcaacggtc tgaccggtac aggcgtgctg   1620
acagagagca acaagaagtt cctgccattc cagcagtttg gcagggatat cgcagatacc   1680
acagacgctg ttagagatcc acagacactg gaaatcctgg acatcacacc ttgcagcttc   1740
ggaggcgtgt ctgtgatcac acctggcacc aacaccagca atcaggtggc agttctgtac   1800
caggacgtga actgtaccga agttcccgtg gccattcatg ccgatcagct gacacctaca   1860
tggagggtgt actccaccgg aagcaatgtg tttcagacca gagctggctg tctgatcgga   1920
gccgagcacg tgaacaatag ctacgagtgc gacatcccta tcggagctgg catctgtgcc   1980
agctaccaga cacagacaaa cagccctggc tctgcctctt ccgtggccag ccagtccatc   2040
attgcctaca caatgtctct gggagccgag aacagcgtgg cctactccaa caactctatc   2100
gctatcccta ccaacttcac aatcagcgtg accacagaga tcctgcctgt gtccatgacc   2160
aagaccagcg tggactgcac catgtacatc tgtggcgatt ccaccgagtg ctccaacctg   2220
ctgctgcagt acggcagctt ctgcacccag ctgaatagag ccctgacagg gatcgctgtg   2280
gaacaggaca agaacaccca agaggtgttc gcacaagtga agcagatcta caagacacct   2340
cctatcaagg acttcggagg attcaacttt agccagattc tgcctgatcc tagcaagcca   2400
agcaagcgga gcttcatcga ggacctgctg ttcaacaaag tgacacttgc cgacgctggc   2460
ttcatcaagc agtatggcga ttgtctggga gacattgctg ccagggatct gatttgtgcc   2520
cagaagttca acggactgac agtgctgcct cctctgctga ccgatgagat gatcgctcag   2580
tacacatctg ccctgctggc tggcacaatc acaagtggct ggacatttgg agctggagct   2640
gctctgcaga ttccctttgc tatgcagatg gcctaccggt tcaacggcat cggagtgacc   2700
cagaatgtgc tgtacgagaa ccagaagctg atcgccaacc agttcaactc tgccatcggc   2760
aagatccagg acagcctgag cagcacagca agcgcactgg gaaagctgca ggacgtggtc   2820
aaccagaatg cccaggcact gaacaccctg gtcaagcagc tgtcctccaa cttcggagcc   2880
atcagctctg tgctgaacga tatcctgagc agactggacc ctcctgaagc cgaggtgcag   2940
atcgacaggc tgatcacagg cagactgcag agcctccaga catacgtgac ccagcagctg   3000
atcagagctg ccgagattag agcctctgcc aatctggcag ccaccaagat gtctgagtgt   3060
gtgctgggac agagcaagag agtggacttc tgtggcaagg gctaccacct gatgagcttc   3120
cctcagtctg cacctcatgg cgtggtgttt ctgcacgtga catatgtgcc agctcaagag   3180
aagaacttca ccaccgctcc agccatctgc cacgacggta aagcccactt tcctagagaa   3240
```

```
ggcgtgttcg tgtccaacgg cacccattgg ttcgtgacac agcggaactt ctacgagcct   3300

cagatcatca ccaccgacaa caccttcgtg tctggcaact gcgacgtcgt gatcggcatt   3360

gtcaacaata ccgtgtacga ccctctgcag ccagagctcg acagcttcaa agaggaactg   3420

gacaagtact tcaagaacca cacaagccct gacgtggacc tgggagatat cagcggaatc   3480

aatgccagcg tcgtgaacat ccagaaagag attgacagac tgaacgaggt ggccaagaat   3540

ctgaacgaga gcctgatcga cctgcaagaa cttgggaagt acgagcagta catcaagtgg   3600

ccttggtaca tctggctggg cttcatcgca ggactgattg ccatcgtgat ggtcacaatc   3660

atgctgtgtt gcatgaccag ctgctgtagc tgtctgaagg gctgttgtag ctgtggcagc   3720

tgctgcaagt tcgacgagga cgattctgag ccagtgctga aaggcgtgaa actgcactac   3780

acatagtaa                                                           3789
```

<210> SEQ ID NO 24
<211> LENGTH: 1273
<212> TYPE: PRT
<213> ORGANISM: Artificial Sequence
<220> FEATURE:
<223> OTHER INFORMATION: SARS-CoV-2 S protein, full-length, modified, plus signal peptide ("SARS-2 S-FS-1")

<400> SEQUENCE: 24

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255
```

-continued

```
Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Gly Ser Ala Ser Ser Val Ala
```

```
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Pro Pro Glu Ala Glu Val Gln
            980                 985                 990

Ile Asp Arg Leu Ile Thr Gly Arg Leu Gln Ser Leu Gln Thr Tyr Val
        995                 1000                1005

Thr Gln Gln Leu Ile Arg Ala Ala Glu Ile Arg Ala Ser Ala Asn Leu
    1010                1015                1020

Ala Ala Thr Lys Met Ser Glu Cys Val Leu Gly Gln Ser Lys Arg Val
1025                1030                1035                1040

Asp Phe Cys Gly Lys Gly Tyr His Leu Met Ser Phe Pro Gln Ser Ala
                1045                1050                1055

Pro His Gly Val Val Phe Leu His Val Thr Tyr Val Pro Ala Gln Glu
            1060                1065                1070

Lys Asn Phe Thr Thr Ala Pro Ala Ile Cys His Asp Gly Lys Ala His
        1075                1080                1085

Phe Pro Arg Glu Gly Val Phe Val Ser Asn Gly Thr His Trp Phe Val
    1090                1095                1100
```

```
Thr Gln Arg Asn Phe Tyr Glu Pro Gln Ile Ile Thr Thr Asp Asn Thr
1105                1110                1115                1120

Phe Val Ser Gly Asn Cys Asp Val Val Ile Gly Ile Val Asn Asn Thr
                1125                1130                1135

Val Tyr Asp Pro Leu Gln Pro Glu Leu Asp Ser Phe Lys Glu Glu Leu
            1140                1145                1150

Asp Lys Tyr Phe Lys Asn His Thr Ser Pro Asp Val Asp Leu Gly Asp
        1155                1160                1165

Ile Ser Gly Ile Asn Ala Ser Val Val Asn Ile Gln Lys Glu Ile Asp
    1170                1175                1180

Arg Leu Asn Glu Val Ala Lys Asn Leu Asn Glu Ser Leu Ile Asp Leu
1185                1190                1195                1200

Gln Glu Leu Gly Lys Tyr Glu Gln Tyr Ile Lys Trp Pro Trp Tyr Ile
                1205                1210                1215

Trp Leu Gly Phe Ile Ala Gly Leu Ile Ala Ile Val Met Val Thr Ile
            1220                1225                1230

Met Leu Cys Cys Met Thr Ser Cys Cys Ser Cys Leu Lys Gly Cys Cys
        1235                1240                1245

Ser Cys Gly Ser Cys Cys Lys Phe Asp Glu Asp Asp Ser Glu Pro Val
    1250                1255                1260

Leu Lys Gly Val Lys Leu His Tyr Thr
1265                1270
```

```
<210> SEQ ID NO 25
<211> LENGTH: 3825
<212> TYPE: DNA
<213> ORGANISM: Artificial Sequence
<220> FEATURE:
<223> OTHER INFORMATION: SARS-CoV-2 S protein, full-length, modified,
      plus signal peptide ("SARS-2 S-FS-1")

<400> SEQUENCE: 25

atgttcgtct tcctggtcct gctccctctg gtgtccagcc agtgtgtgaa cctgaccacc     60

agaacacagc tgcctccagc ctacaccaac agctttacca gaggcgtgta ctatcccgac    120

aaggtgttca gatccagcgt gctgcactct acccaggacc tgttcctgcc tttcttcagc    180

aacgtgacct ggttccacgc catccacgtg agcggtacca atggcaccaa gagattcgac    240

aatcccgtgc tgcccttcaa cgacggagtg tactttgcca gcaccgagaa gtccaacatc    300

atcagaggct ggatcttcgg caccacactg gacagcaaga cccagagcct gctgatcgtg    360

aacaacgcca ccaacgtggt catcaaagtg tgcgagttcc agttctgcaa cgatcccttc    420

ctgggagtct actaccacaa gaacaacaag agctggatgg aaagcgagtt cagagtgtac    480

agctctgcca acaactgcac cttcgagtac gtgtcccagc ctttcctgat ggacctggaa    540

ggcaagcagg gcaatttcaa gaatctccga gagttcgtgt tcaagaacat cgacggctac    600

ttcaagatct acagcaagca cacacctatc aacctcgtga gggatctgcc tcagggcttc    660

tctgctctgg aacctctggt ggatctgccc atcggcatca acatcactcg gtttcagaca    720

ctgctggcac tgcacagaag ctacctgaca cctggcgata gcagcagcgg atggacagct    780

ggtgctgcag cttactatgt gggctacctg cagcctagaa ccttcctgct gaagtacaac    840

gagaacggca ccatcaccga tgccgtggat tgtgctctgg atcctctgag cgagacaaag    900

tgcaccctga agtccttcac cgtggagaag ggcatctacc agaccagcaa cttcagggtg    960

cagcccaccg aatccatcgt gcggttccct aacatcacca atctgtgtcc ctttggcgag   1020
```

-continued gtgttcaatg ccaccagatt cgcctctgtg tacgcctgga accggaagcg gatcagcaat 1080
tgcgttgccg actactccgt gctgtacaac tcagccagct tcagcacctt caagtgctac 1140
ggagtgagcc ctaccaagct gaacgacctg tgcttcacaa acgtgtatgc tgacagcttc 1200
gtgatcagag gagatgaagt gaggcagatt gctcctggac agacaggcaa gattgcagat 1260
tacaactaca agctgcctga cgacttcaca ggctgtgtga ttgcctggaa cagcaacaac 1320
ctggactcca aagtcggagg caactacaac tacctgtaca gactgttcag gaagtccaat 1380
ctgaagccct tcgaacggga catctccacc gagatctatc aggctggcag cacaccttgt 1440
aatggagtgg aaggcttcaa ctgctacttc ccactgcagt cctacggctt tcagcccaca 1500
aatggcgtgg gctatcagcc ctacagagtg gtggtgctga gcttcgaact gctgcatgct 1560
cctgccacag tgtgcggacc taagaaatcc accaatctcg tgaagaacaa atgcgtgaac 1620
ttcaacttca acggtctgac cggtacaggc gtgctgacag agagcaacaa gaagttcctg 1680
ccattccagc agtttggcag ggatatcgca gataccacag acgctgttag agatccacag 1740
acactggaaa tcctggacat cacaccttgc agcttcggag gcgtgtctgt gatcacacct 1800
ggcaccaaca ccagcaatca ggtggcagtt ctgtaccagg acgtgaactg taccgaagtt 1860
cccgtggcca ttcatgccga tcagctgaca cctacatgga gggtgtactc caccggaagc 1920
aatgtgtttc agaccagagc tggctgtctg atcggagccg agcacgtgaa caatagctac 1980
gagtgcgaca tccctatcgg agctggcatc tgtgccagct accagacaca gacaaacagc 2040
cctggctctg cctcttccgt ggccagccag tccatcattg cctacacaat gtctctggga 2100
gccgagaaca gcgtggccta ctccaacaac tctatcgcta tccctaccaa cttcacaatc 2160
agcgtgacca cagagatcct gcctgtgtcc atgaccaaga ccagcgtgga ctgcaccatg 2220
tacatctgtg gcgattccac cgagtgctcc aacctgctgc tgcagtacgg cagcttctgc 2280
acccagctga atagagccct gacagggatc gctgtggaac aggacaagaa cacccaagag 2340
gtgttcgcac aagtgaagca gatctacaag acacctccta tcaaggactt cggaggattc 2400
aactttagcc agattctgcc tgatcctagc aagccaagca agcggagctt catcgaggac 2460
ctgctgttca acaaagtgac acttgccgac gctggcttca tcaagcagta tggcgattgt 2520
ctgggagaca ttgctgccag ggatctgatt tgtgcccaga agttcaacgg actgacagtg 2580
ctgcctcctc tgctgaccga tgagatgatc gctcagtaca catctgccct gctggctggc 2640
acaatcacaa gtggctggac atttggagct ggagctgctc tgcagattcc ctttgctatg 2700
cagatggcct accggttcaa cggcatcgga gtgacccaga atgtgctgta cgagaaccag 2760
aagctgatcg ccaaccagtt caactctgcc atcggcaaga tccaggacag cctgagcagc 2820
acagcaagcg cactgggaaa gctgcaggac gtggtcaacc agaatgccca ggcactgaac 2880
accctggtca agcagctgtc ctccaacttc ggagccatca gctctgtgct gaacgatatc 2940
ctgagcagac tggaccctcc tgaagccgag gtgcagatcg acaggctgat cacaggcaga 3000
ctgcagagcc tccagacata cgtgacccag cagctgatca gagctgccga gattagagcc 3060
tctgccaatc tggcagccac caagatgtct gagtgtgtgc tgggacagag caagagagtg 3120
gacttctgtg gcaagggcta ccacctgatg agcttccctc agtctgcacc tcatggcgtg 3180
gtgtttctgc acgtgacata tgtgccagct caagagaaga acttcaccac cgctccagcc 3240
atctgccacg acggtaaagc ccactttcct agagaaggcg tgttcgtgtc caacggcacc 3300
cattggttcg tgacacagcg gaacttctac gagcctcaga tcatcaccac cgacaacacc 3360
ttcgtgtctg gcaactgcga cgtcgtgatc ggcattgtca acaataccgt gtacgaccct 3420

-continued

```
ctgcagccag agctcgacag cttcaaagag gaactggaca agtacttcaa gaaccacaca   3480

agccctgacg tggacctggg agatatcagc ggaatcaatg ccagcgtcgt gaacatccag   3540

aaagagattg acagactgaa cgaggtggcc aagaatctga acgagagcct gatcgacctg   3600

caagaacttg ggaagtacga gcagtacatc aagtggcctt ggtacatctg gctgggcttc   3660

atcgcaggac tgattgccat cgtgatggtc acaatcatgc tgtgttgcat gaccagctgc   3720

tgtagctgtc tgaagggctg ttgtagctgt ggcagctgct gcaagttcga cgaggacgat   3780

tctgagccag tgctgaaagg cgtgaaactg cactacacat agtaa                   3825


<210> SEQ ID NO 26
<211> LENGTH: 124
<212> TYPE: DNA
<213> ORGANISM: Artificial Sequence
<220> FEATURE:
<223> OTHER INFORMATION: Pr13.5long promoter

<400> SEQUENCE: 26

taaaaataga aactataatc atataatagt gtaggttggt agtattgctc ttgtgactag     60

agactttagt taaggtactg taaaaataga aactataatc atataatagt gtaggttggt    120

agta                                                                  124


<210> SEQ ID NO 27
<211> LENGTH: 100
<212> TYPE: DNA
<213> ORGANISM: Artificial Sequence
<220> FEATURE:
<223> OTHER INFORMATION: Pr1328 promoter

<400> SEQUENCE: 27

tatattatta agtgtggtgt ttggtcgatg taaaattttt gtcgataaaa attaaaaaat     60

aacttaattt attattgatc tcgtgtgtac aaccgaaatc                          100
```

RECOMBINANT MODIFIED VACCINIA VIRUS (MVA) VACCINE AGAINST CORONAVIRUS DISEASE

TECHNICAL FIELD

The present invention relates to the field of vaccines. More specifically, the invention relates to vaccines based on a viral vector for the delivery of antigens targeting an infectious disease. Particularly, the invention relates to a recombinant Modified Vaccinia Virus Ankara (MVA) encoding a spike (S) protein of severe acute respiratory syndrome coronavirus 2 (SARS-CoV-2), the causative agent of coronavirus disease 19 (COVID-19). The invention also relates to a recombinant MVA encoding a part of a SARS-CoV-2 S protein, such as a receptor-binding domain (RBD), and antigenic sequences from other SARS-CoV-2 proteins. The invention further relates to medical uses of the recombinant MVA in the prevention of COVID-19.

BACKGROUND

In recent years, certain coronaviruses caused significant outbreaks of infectious diseases in humans: the severe acute respiratory syndrome coronavirus (SARS-CoV-1) in 2002/2003, the Middle East respiratory syndrome coronavirus (MERS-CoV) in 2012, and another severe acute respiratory syndrome coronavirus (SARS-CoV-2) in 2019/2020.

SARS-CoV-2 was described soon after a series of unidentified pneumonia diseases had occurred in Wuhan, China, at the end of 2019 (Zhou et al., 2020). Typical clinical symptoms were reported to be fever, dry cough, dyspnea, headache, and pneumonia, and the infection occasionally resulted in progressive respiratory failure due to alveolar damage and even death (Zhou et al., 2020). Moreover, olfactory and gustatory disorders are regarded as strong specific symptoms (Lechien et al., 2020). In March 2020, WHO characterized the disease—meanwhile referred to as coronavirus disease 2019 (COVID-19)—as a pandemic. SARS-CoV-2 showed efficient transmission in the human population with a reproductive index $R_0$ of more than 3 in the initial phase of the pandemic.

COVID-19, similar to the diseases caused by SARS-CoV-1 and MERS-CoV, is considered to have its origin in a zoonotic transfer of the causative virus from its natural reservoir host, most likely bats, to humans, possibly via an intermediate mammalian host. Due to the fact that COVID-19 appeared only recently, the knowledge and understanding of the disease and its causative virus, SARS-CoV-2, is limited.

SARS-CoV-2 belongs to the Coronaviridae family, a family of positive-sense, single-stranded RNA viruses. Like other coronaviruses, SARS-CoV-2 is characterized by a crown-like ("corona") appearance when viewed by electron microscopy which is produced by the spikes extruding from the virus surface. Such spike (S) proteins are essential for attachment and entry of the virus into host cells. The SARS-CoV-2 S protein is a large type I transmembrane protein composed of two subunits, S1 and S2. The S1 subunit contains a receptor-binding domain (RBD) that mediates virus attachment to the host cell receptor. The S2 subunit (ectodomain) mediates fusion between the viral and host cell membranes.

It is assumed that the S protein plays a key role in the induction of neutralizing antibodies, T cell responses and protective immunity. The entry of SARS-CoV-2 into host cells involves a series of conformational changes upon binding to the cellular receptor angiotensin-converting enzyme 2 (ACE), and eventually the S protein undergoes a substantial structural rearrangement from the prefusion to the postfusion conformation (Wrapp et al., 2020). To prevent entry of SARS-CoV-2 into host cells, antibodies against the prefusion form of S are considered to be much more effective than those against the postfusion form, which renders the prefusion form of SARS-CoV-2 S the preferred antigenic conformation of S for a vaccine.

However, despite global efforts and increasing knowledge about SARS-CoV-2, there are no pharmaceutical interventional measures available yet to prevent or treat COVID-19.

The most efficient and possibly the only way to limit and halt the COVID-19 pandemic is an effective prophylactic vaccine against SARS-CoV-2. However, evaluation of vaccine candidates against SARS-CoV-1 and MERS-CoV have revealed that vaccine-related immunopathological processes have to be taken into account when developing a vaccine against these coronaviruses.

At least two mechanisms have to be considered: First, an antibody-dependent enhancement (ADE) of the related SARS-CoV-1 infection has been described that can lead to acute lung injury (Liu et al., 2019). The antibodies are directed against the major surface protein of the virus, the S protein, and incomplete neutralization would enhance uptake of the virus into certain cells within the lung. The subsequent secretion of cytokines and chemokines could attract various types of immune cells that may play beneficial as well as detrimental roles and exacerbate the disease. Second, some types of SARS-CoV-1 and MERS-CoV antigens like the nucleocapsid protein N or whole inactivated virus seem to favor an immunopathological T cell response, and sometimes also an immune response skewed toward the so-called Th2 type that favors some effector functions of the immune system that are not protective against the virus and can exacerbate disease (Deming et al., 2006; Yasui et al., 2008; Agrawal et al., 2016).

Candidate vaccines against SARS-CoV-2 are being developed based on a large variety of platforms, among them nucleic acids (RNA- and DNA-based vaccines), protein, inactivated SARS-CoV-2 virus, live SARS-CoV-2 virus and various live viral vector vaccines (Le et al., 2020). The exact nature of the antigens used has not been disclosed yet for the vast majority of the vaccine candidates.

SUMMARY OF INVENTION

It is an object of the present invention to provide a vaccine against SARS-CoV-2 infection and related diseases. In particular, it is an object to provide such a vaccine which involves only low or no immunopathological disease-enhancing effects.

The object of the present invention is solved by the provision of a recombinant Modified Vaccinia Virus Ankara (MVA) encoding SARS-CoV-2 derived antigens. In particular, the invention is defined by the appended claims and by the following aspects and their embodiments.

In one aspect, the invention provides a recombinant MVA comprising:

a nucleic acid sequence encoding an amino acid sequence of a SARS-CoV-2 spike (S) protein or a part thereof, wherein (A) the amino acid sequence is an amino acid sequence of a SARS-CoV-2 S full-length protein;

(B) the part of the amino acid sequence is an amino acid sequence of a part of a SARS-CoV-2 S protein S1 domain, which part comprises or consists of a SARS-CoV-2 S receptor binding domain (RBD).

In another aspect, the invention provides a recombinant MVA comprising:

(a) a nucleic acid sequence encoding an amino acid sequence of a part of a SARS-CoV-2 S protein S1 domain, which part comprises or consists of a SARS-CoV-2 S RBD; and/or (b) a nucleic acid sequence encoding an amino acid sequence of a SARS-CoV-2 fusion protein comprising two or more antigenic parts from one or more SARS-CoV-2 proteins, which parts are not naturally exposed on the surface of SARS-CoV-2 or a virion derived therefrom.

In yet another aspect, the invention provides a recombinant MVA comprising a nucleic acid sequence encoding an amino acid sequence of a SARS-CoV-2 S full-length protein, preferably comprising two consecutive non-native proline residues, more preferably comprising two consecutive non-native proline residues and a further modification capable of preventing proteolytic cleavage of the full-length protein by furin-like proteases.

In a further aspect, the invention provides a DNA sequence, e.g. a plasmid, preferably for (or suitable for) the preparation of a recombinant virus, more preferably for (or suitable for) the preparation of a recombinant MVA as described herein, comprising:

(aa) a nucleic acid sequence encoding an amino acid sequence of a part of a SARS-CoV-2 S protein S1 domain, which part comprises or consists of a SARS-CoV-2 S RBD; and/or (bb) a nucleic acid sequence encoding an amino acid sequence of a SARS-CoV-2 fusion protein comprising two or more antigenic parts from one or more SARS-CoV-2 proteins, which parts are not naturally exposed on the surface of SARS-CoV-2 or a virion derived therefrom; or (cc) a nucleic acid sequence encoding an amino acid sequence of a SARS-CoV-2 S full-length protein, preferably comprising two consecutive non-native proline residues, more preferably comprising two consecutive non-native proline residues and a further modification capable of preventing proteolytic cleavage of the full-length protein by furin-like proteases.

In a further aspect, the invention provides a method for the preparation of a recombinant virus, preferably a recombinant MVA as described herein, comprising the steps of:

(1) providing a DNA sequence, e.g. a plasmid as described herein;

(2) contacting said DNA sequence with an MVA for homologous recombination; and (3) obtaining the recombinant virus, preferably the recombinant MVA.

In a further aspect, the invention provides a pharmaceutical composition, or a vaccine, comprising a recombinant MVA as described herein, further comprising a pharmaceutically acceptable carrier or excipient.

In a further aspect, the invention provides a use of a recombinant MVA as described herein for the preparation of a pharmaceutical composition, or a vaccine.

In a further aspect, the invention provides a recombinant MVA as described herein for use as a pharmaceutical, or a vaccine.

In a further aspect, the invention provides a recombinant MVA as described herein for use in the prevention or treatment of a viral infection, preferably a coronavirus infection, more preferably coronavirus disease 19 (COVID-19).

In a further aspect, the invention provides a use of a recombinant MVA as described herein for the preparation of a pharmaceutical, or a vaccine.

In a further aspect, the invention provides a use of a recombinant MVA as described herein for the preparation of a pharmaceutical, or a vaccine, for the prevention or treatment of a viral infection, preferably a coronavirus infection, more preferably coronavirus disease 19 (COVID-19).

In a further aspect, the invention provides a method of prevention or treatment of a viral infection, preferably a coronavirus infection, preferably coronavirus disease 19 (COVID-19), comprising the step of administering to a subject a recombinant MVA as described herein.

In a further aspect, the invention provides a method for inducing an immune response to a coronavirus, preferably SARS-CoV-2, in a subject, comprising the step of administering to a subject a recombinant MVA as described herein.

In a further aspect, the invention provides an amino acid sequence of a part of a SARS-CoV-2 S protein S1 domain, which part comprises or consists of a SARS-CoV-2 S RBD.

In a further aspect, the invention provides a nucleic acid encoding an amino acid sequence of a part of a SARS-CoV-2 S protein S1 domain, which part comprises or consists of a SARS-CoV-2 S RBD.

In a further aspect, the invention provides an amino acid sequence of a SARS-CoV-2 fusion protein comprising two or more antigenic parts from one or more SARS-CoV-2 proteins, which parts are not naturally exposed on the surface of SARS-CoV-2 or a virion derived therefrom.

In a further aspect, the invention provides a nucleic acid sequence encoding an amino acid sequence of a SARS-CoV-2 fusion protein comprising two or more antigenic parts from one or more SARS-CoV-2 proteins, which parts are not naturally exposed on the surface of SARS-CoV-2 or a virion derived therefrom.

In a further aspect, the invention provides an amino acid sequence of a SARS-CoV-2 S full-length protein comprising two consecutive non-native proline residues, preferably comprising two consecutive non-native proline residues and a further modification capable of preventing proteolytic cleavage of the full-length protein by furin-like proteases.

In a further aspect, the invention provides a nucleic acid encoding an amino acid sequence of a SARS-CoV-2 S full-length protein comprising two consecutive non-native proline residues, preferably comprising two consecutive non-native proline residues and a further modification capable of preventing proteolytic cleavage of the full-length protein by furin-like proteases.

In a further aspect, the invention provides a pharmaceutical composition, or a vaccine, comprising a protein or peptide, or a fusion protein, comprising an amino acid sequence as described herein, further comprising a pharmaceutically acceptable carrier or excipient.

In a further aspect, the invention provides a protein or peptide, or a fusion protein, comprising an amino acid sequence as described herein for use as a pharmaceutical, or a vaccine.

In a further aspect, the invention provides a protein or peptide, or a fusion protein, comprising an amino acid sequence as described herein for use in the prevention or treatment of a viral infection, preferably a coronavirus infection, more preferably coronavirus disease 19 (COVID-19).

In a further aspect, the invention provides a use of an amino acid sequence as described herein for the preparation of a DNA vaccine.

In a further aspect, the invention provides a use of an amino acid sequence as described herein for the preparation of a RNA, e.g. mRNA, vaccine.

In a further aspect, the invention provides a pharmaceutical composition, or a vaccine, comprising a DNA comprising a nucleotide sequence as described herein, further comprising a pharmaceutically acceptable carrier or excipient.

In a further aspect, the invention provides a DNA comprising a nucleotide sequence as described herein for use as a pharmaceutical, or a vaccine.

In a further aspect, the invention provides a DNA comprising a nucleotide sequence as described herein for use in the prevention or treatment of a viral infection, preferably a coronavirus infection, more preferably coronavirus disease 19 (COVID-19).

In a further aspect, the invention provides a pharmaceutical composition, or a vaccine, comprising a RNA, e.g. mRNA, encoding an amino acid sequence as described herein, further comprising a pharmaceutically acceptable carrier or excipient.

In a further aspect, the invention provides a RNA, e.g. mRNA, encoding an amino acid sequence as described herein for use as a pharmaceutical, or a vaccine.

In a further aspect, the invention provides a RNA, e.g. mRNA, encoding an amino acid sequence as described herein for use in the prevention or treatment of a viral infection, preferably a coronavirus infection, more preferably coronavirus disease 19 (COVID-19).

In a further aspect, the invention provides an antigenic fragment from a SARS-CoV-2 protein selected from the group consisting of a protein 3a, a protein E and a protein M.

These aspects and their embodiments will be described in further detail in connection with the description of invention.

BRIEF DESCRIPTION OF DRAWINGS

FIG. 2 shows the full-length amino acid sequences of SARS-CoV-2 protein 3a, protein M and protein E. The fragments used for construction of the SARS-CoV-2 fusion protein are underlined.

FIG. 10 shows the induction of antigen specific $CD8^+$ and $CD4^+$ T cells against SARS-CoV-2 encoded regions by MVA-mBN499 and MVA-mBN500. Balb/c mice (n=3/group) were vaccinated as described for FIG. 9 and sacrificed on day 34. Intracellular cytokine staining in which $4\times10^5$ splenocytes were incubated with SARS-CoV-2 derived peptide pools as indicated. MVA E3L dominant $CD8^+$ T cell epitope was used as positive control. Percentage of $CD8^+$ $CD44^+$ IFN-$\gamma^+$ TNF$\alpha^+$ (A) and $CD4^+$ $CD44^+$ IFN-$\gamma^+$ (B) after 6-hour incubation is shown. Background control is subtracted. Data are expressed as Mean±SEM.

FIG. 11 shows that MVA mBN500, but not MVA mBN499, induces antibodies that bind to the SARS-CoV-2 RBD domain. On days 0 and 21, Balb/c mice (n=3/group) were vaccinated as described for FIG. 9. Mice were bled at days 20 and 34 after prime immunization, respectively. Sera from days 20 (A) and 34 (final day) (B) were serially diluted and assayed using the surrogate virus neutralization test.

Figure 13:
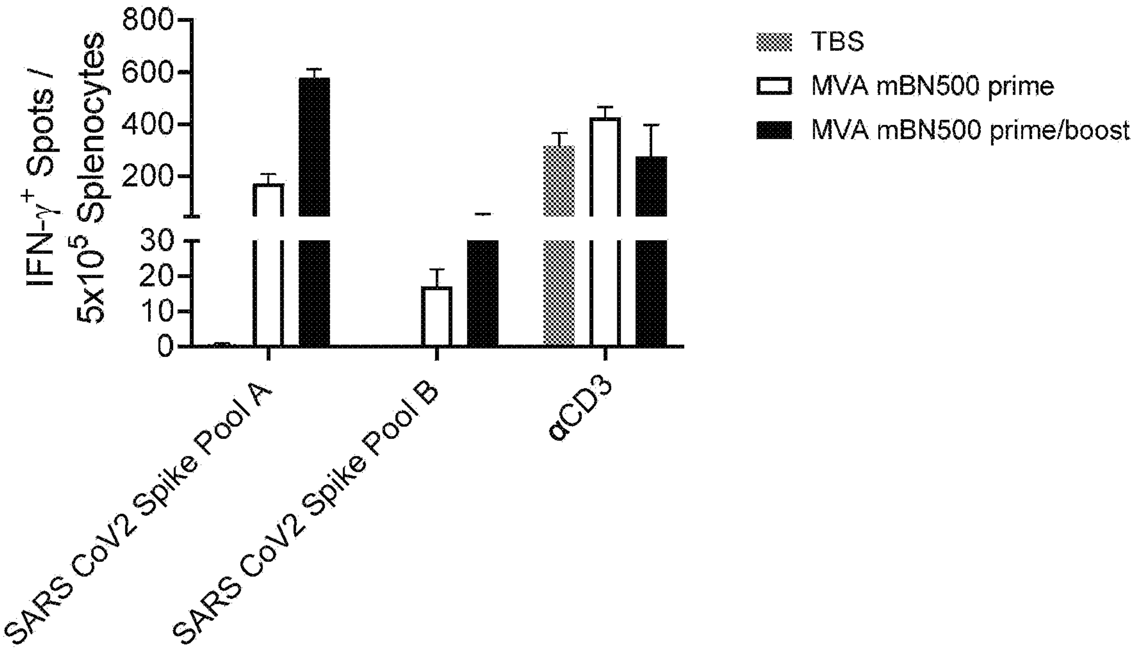

FIG. 13 shows that boost immunization with MVA-mBN500 enhances antigen specific IFN-γ production against SARS-CoV-2 peptide pools containing the RBD domain. On day 0 and 21, Balb/c mice (n=5/group) were vaccinated intramuscularly with either TBS or $1\times10^8$ $TCID_{50}$ of MVA-mBN500. On day 21, Balb/c mice were boosted intramuscularly with either TBS or $1\times10^8$ $TCID_{50}$ of MVA-mBN500. Mice were sacrificed on day 34 after prime immunization. IFN-γ ELISPOT in which $5\times10^5$ splenocytes were incubated with SARS-CoV-2 derived peptide pools as indicated. Anti-CD3 antibody was used as positive control. Data are expressed as Mean±SEM.

Figure 14:
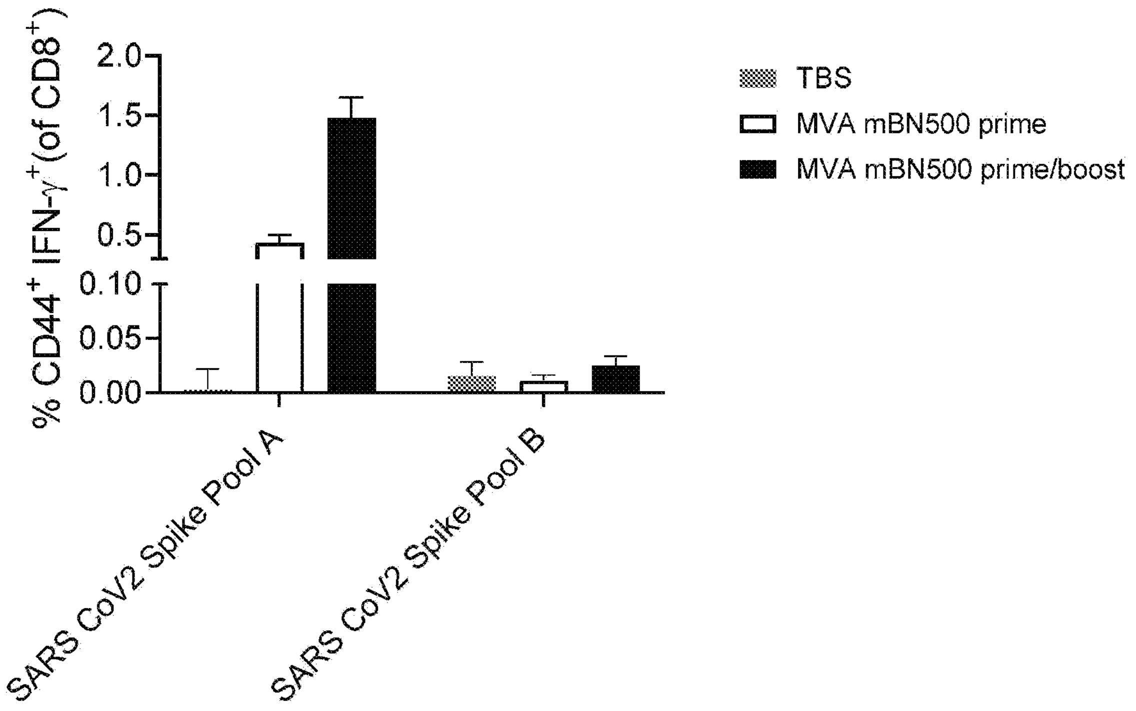
Figure 15:
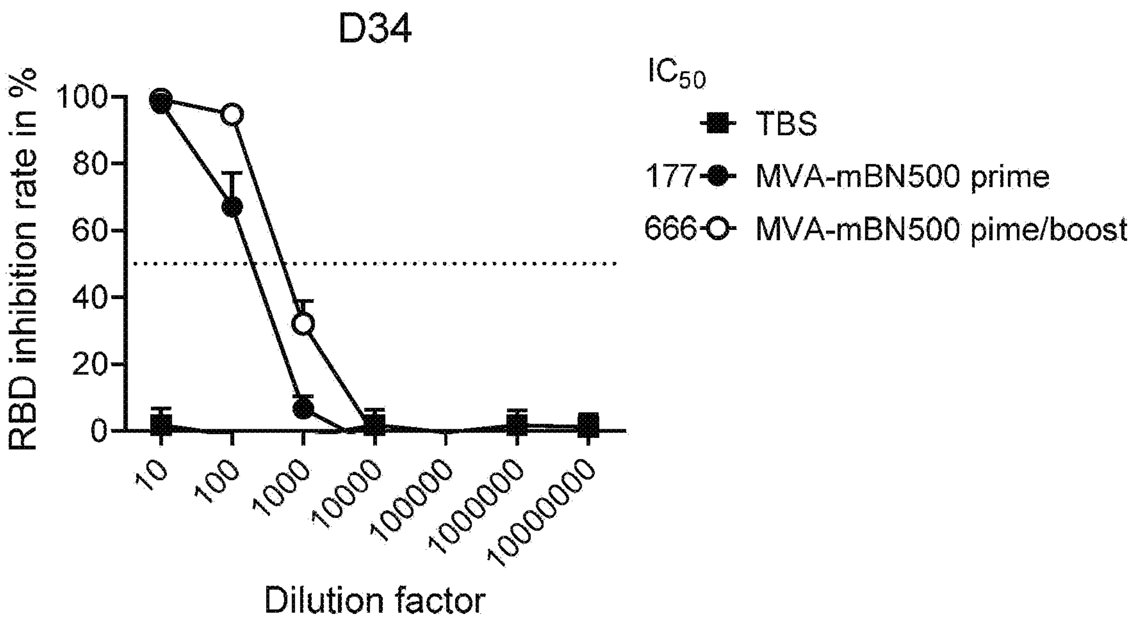

FIG. 14 shows that boost immunization with MVA-mBN500 enhances antigen specific $CD8^+$ T cells against SARS-CoV-2 peptide pools. Balb/c mice (n=5/group) were vaccinated as described for FIG. 13 and sacrificed on day 34. Intracellular cytokine staining in which $5\times10^5$ splenocytes from were incubated with SARS-CoV-2 derived peptide pools. Percentage of $CD8^+$ $CD44^+$ IFN-$\gamma^+$ after 6-hour incubation is shown. Background control is subtracted. Data are expressed as Mean±SEM FIG. 15 shows that boost immunization with MVA mBN500 enhances antibodies that bind to the SARS-CoV-2 RBD domain. Balb/c mice (n=3/group) were vaccinated as described for FIG. 13. Mice were bled on days 20 and 34 after prime immunization respectively. Sera from day 34 (final day) were serially diluted and assayed using the surrogate virus neutralization test. The half maximal inhibitory concentration ($IC_{50}$) was calculated.

BRIEF DESCRIPTION OF SEQUENCES

SEQ ID NO: 1 depicts the amino acid sequence of SARS-CoV-2 S full-length protein (YP_009724390.1; SARS-CoV-2 isolate Wuhan-Hu-1, NC_045512.2).

SEQ ID NO: 2 depicts a nucleic acid sequence encoding SEQ ID NO: 1.

Figure 1:
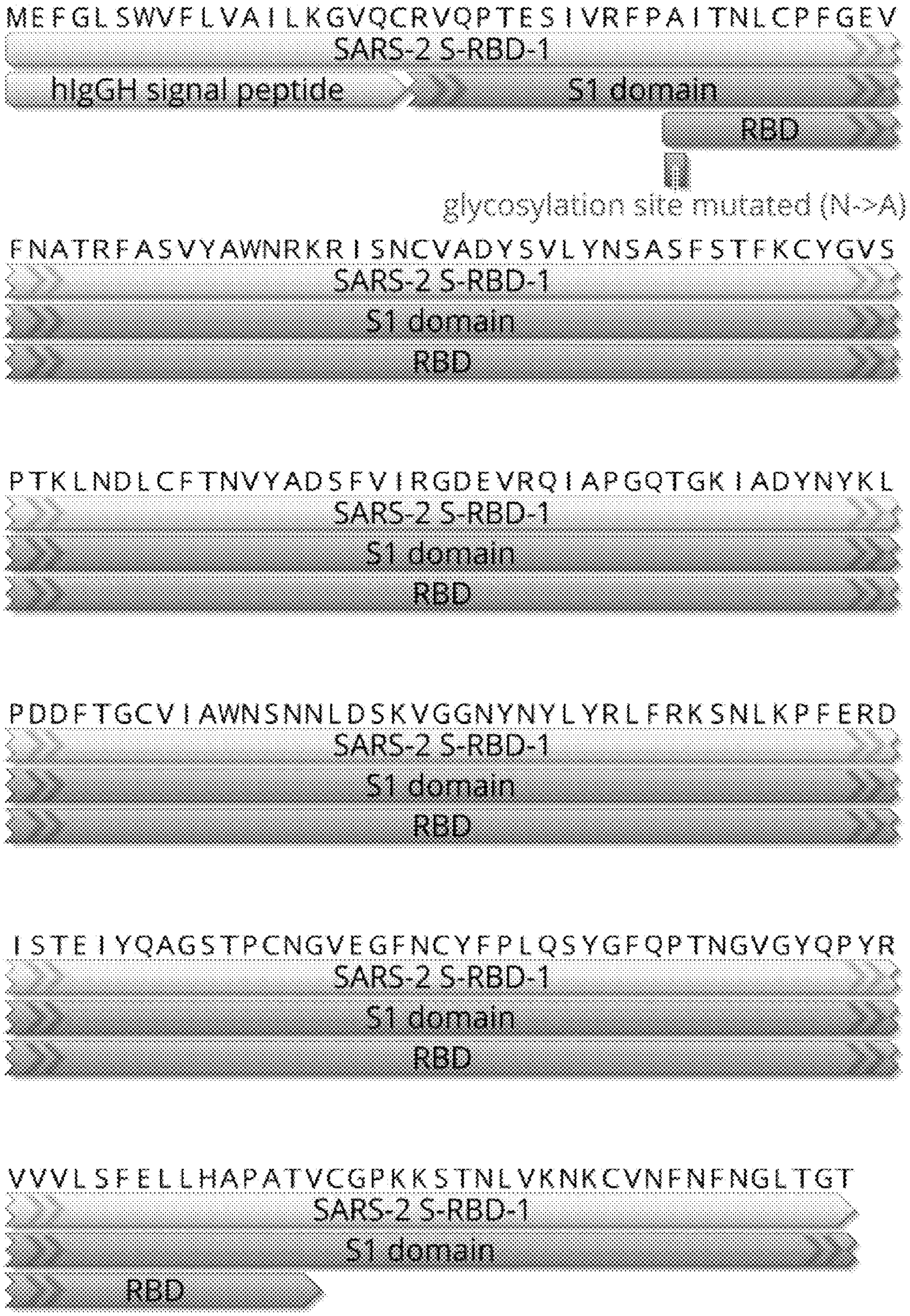
FIG. 1 shows the amino acid sequence ("SARS-2 S-RBD-1") of a part of the SARS-CoV-2 S1 domain (including the RBD amino acid sequence) and a signal peptide from human IgG heavy chain ("hIgGH"). Further shown is an amino acid modification (N331A) at an RBD glycosylation site.

SEQ ID NO: 3 depicts the amino acid sequence of SARS-CoV-2 S RBD including modification (N331A) (see FIG. 1, referred to as "RBD").

SEQ ID NO: 4 depicts a nucleic acid sequence encoding SEQ ID NO: 3.

SEQ ID NO: 5 depicts the amino acid sequence of a part of SARS-CoV-2 S protein S1 domain comprising the SARS-CoV-2 S RBD including modification (N331A) (see FIG. 1, referred to as "S1 domain").

SEQ ID NO: 6 depicts a nucleic acid sequence encoding SEQ ID NO: 5.

SEQ ID NO: 7 depicts the amino acid sequence of a human IgGH secretion signal peptide (see FIG. 1, referred to as "hIgGH signal peptide").

SEQ ID NO: 8 depicts a nucleic acid sequence encoding SEQ ID NO: 7.

SEQ ID NO: 9 depicts the amino acid sequence of a part of SARS-CoV-2 S protein S1 domain comprising the SARS-CoV-2 S RBD including modification (N331A) plus a human IgGH secretion signal peptide (see FIG. 1, referred to as "SARS-2 S-RBD-1").

SEQ ID NO: 10 depicts a nucleic acid sequence encoding SEQ ID NO: 9.

SEQ ID NO: 11 depicts the amino acid sequence of SARS-CoV-2 full-length protein 3a (YP_009724391.1).

SEQ ID NO: 12 depicts the amino acid sequence of SARS-CoV-2 full-length protein E (YP_009724392.1).

SEQ ID NO: 13 depicts the amino acid sequence of SARS-CoV-2 full-length protein M (YP_009724393.1).

SEQ ID NO: 14 depicts the amino acid sequence of a first protein 3a fragment (3a-1) used for construction of a SARS CoV-2 3aEM fusion protein (see FIG. 2, amino acids no. 56-83).

SEQ ID NO: 15 depicts the amino acid sequence of a second protein 3a fragment (3a-2) used for construction of a SARS CoV-2 3aEM fusion protein (see FIG. 2, amino acids no. 178-275).

SEQ ID NO: 16 depicts the amino acid sequence of a protein E fragment used for construction of a SARS CoV-2 3aEM fusion protein (see FIG. 2, amino acids no. 38-73).

SEQ ID NO: 17 depicts the amino acid sequence of a first protein M fragment (M-1) used for construction of a SARS CoV-2 3aEM fusion protein (see FIG. 2, amino acids no. 37-51).

SEQ ID NO: 18 depicts the amino acid sequence of a second protein M fragment (M-2) used for construction of a SARS CoV-2 fusion protein (see FIG. 2, amino acids no. 94-212).

SEQ ID NO: 19 depicts the amino acid sequence encompassing protein 3a-1, 3a-2, protein E, and protein M-1, M-2 fragments, fused together.

Figure 3:
FIG. 3 shows the amino acid sequence ("SARS-2 3aEM-1") of SARS-CoV-2 fusion protein resulting from a methionine (providing a start codon in the corresponding nucleotide sequence) at amino acid position 1, followed by fusion of fragments from SARS-CoV-2 protein 3a ("3a fragment 1, 2"), protein E ("E fragment") and protein M ("M fragment 1, 2") as described in FIG. 2. Further shown are amino acid modifications (A131W, Y132F and S179D, Y180F).
Figure 3:
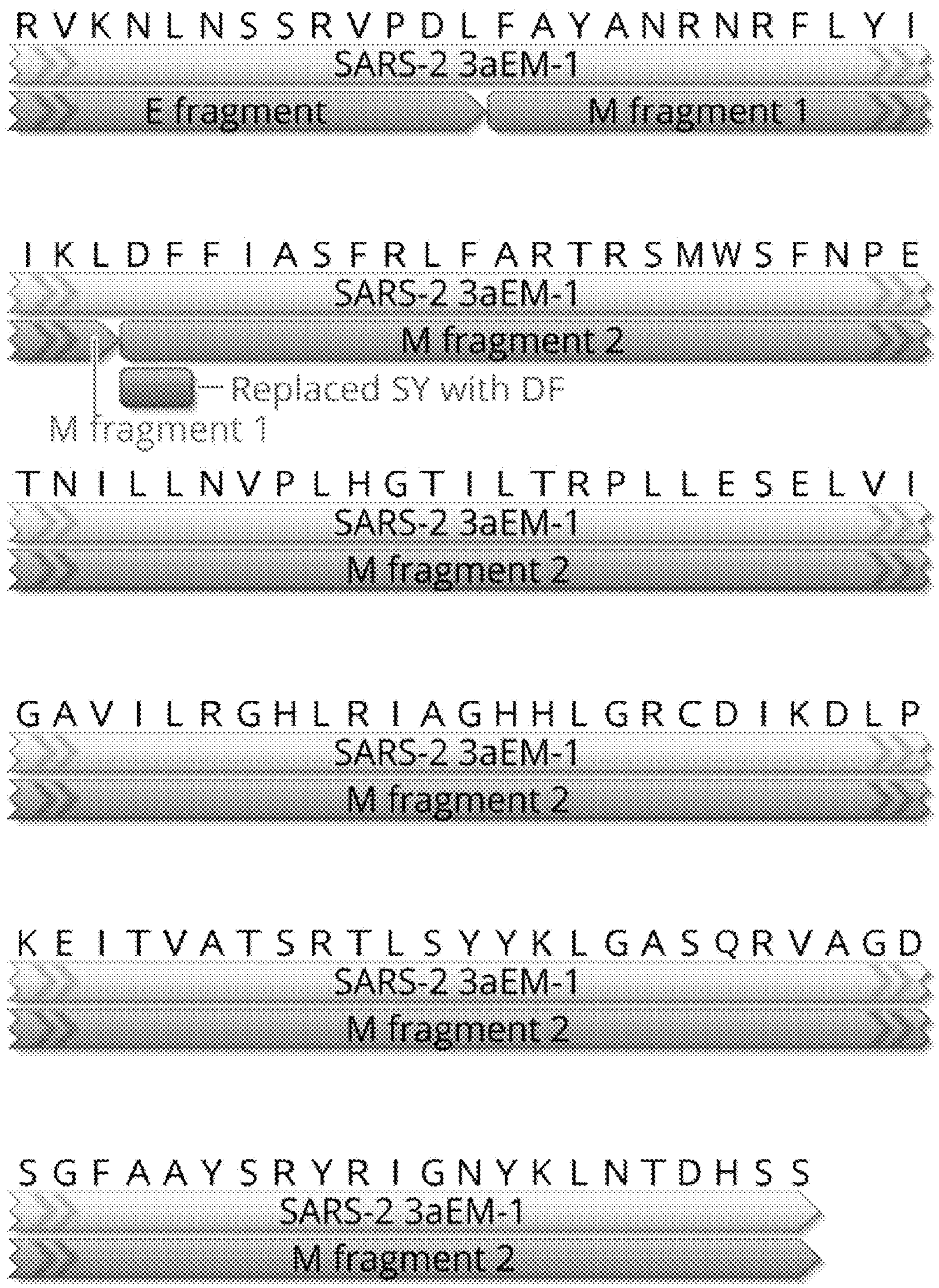

SEQ ID NO: 20 depicts the amino acid sequence of SARS-CoV-2 3aEM fusion protein including modifications (A131W, Y132F and S179D, Y180F) (see FIG. 3, referred to as "SARS-2 3aEM-1").

SEQ ID NO: 21 depicts a nucleic acid sequence encoding SEQ ID NO: 20.

Figure 4:
FIG. 4 shows the amino acid sequence ("SARS-2 S-FS-1") of stabilized SARS-CoV-2 S full-length protein (i.e., S1 domain including the N-terminal domain (NTD) and the RBD; S2, S2' domain including a transmembrane domain) and its native signal peptide. Further shown is a GSAS amino acid stretch at the previous polybasic RRAR furin cleavage site, a cleavage site (amino acids RS) in the S2 domain, and two consecutive prolines in the S2 domain as a result of amino acid exchange (K986P and V987P).
Figure 4:
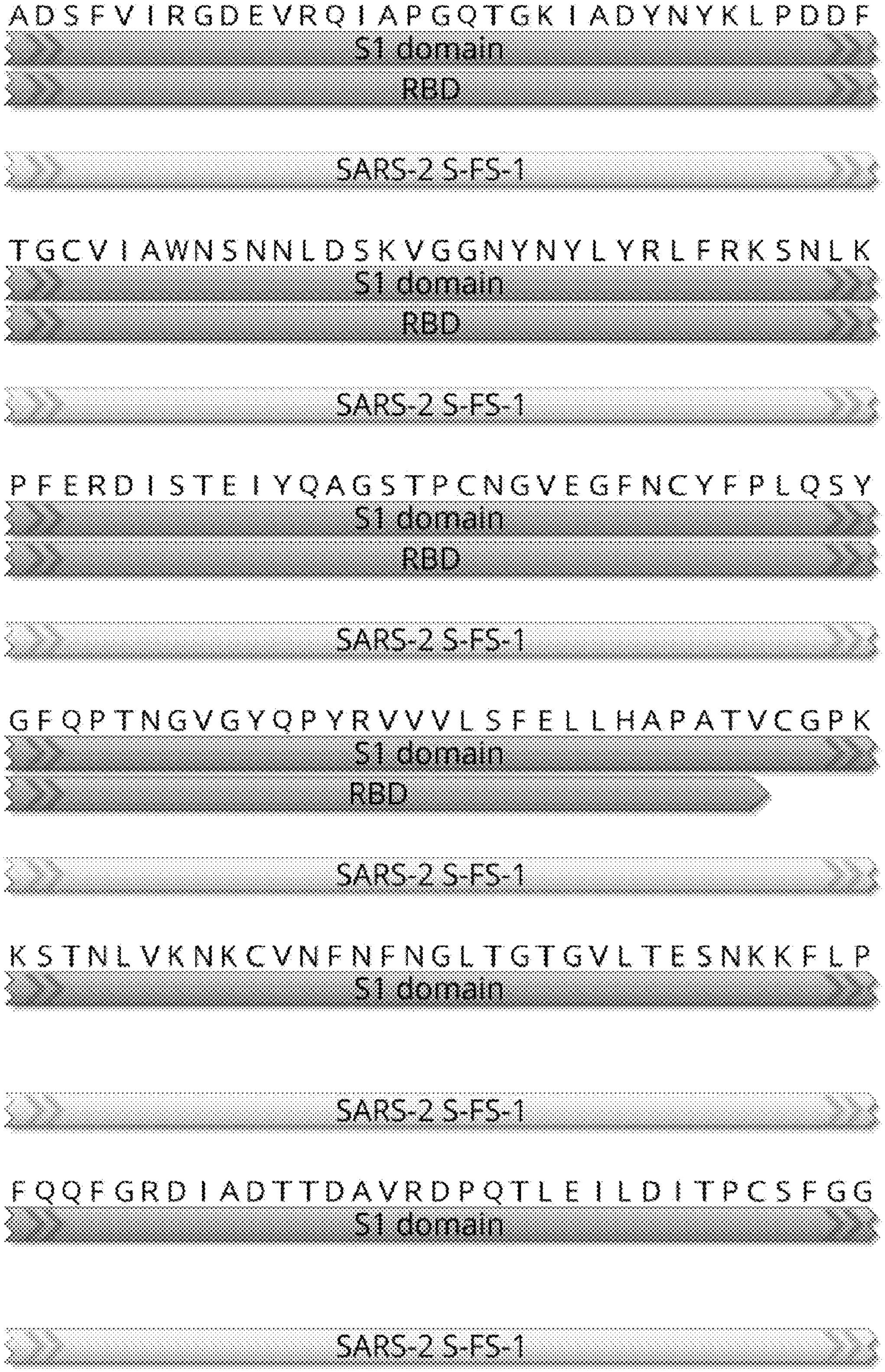
Figure 4:
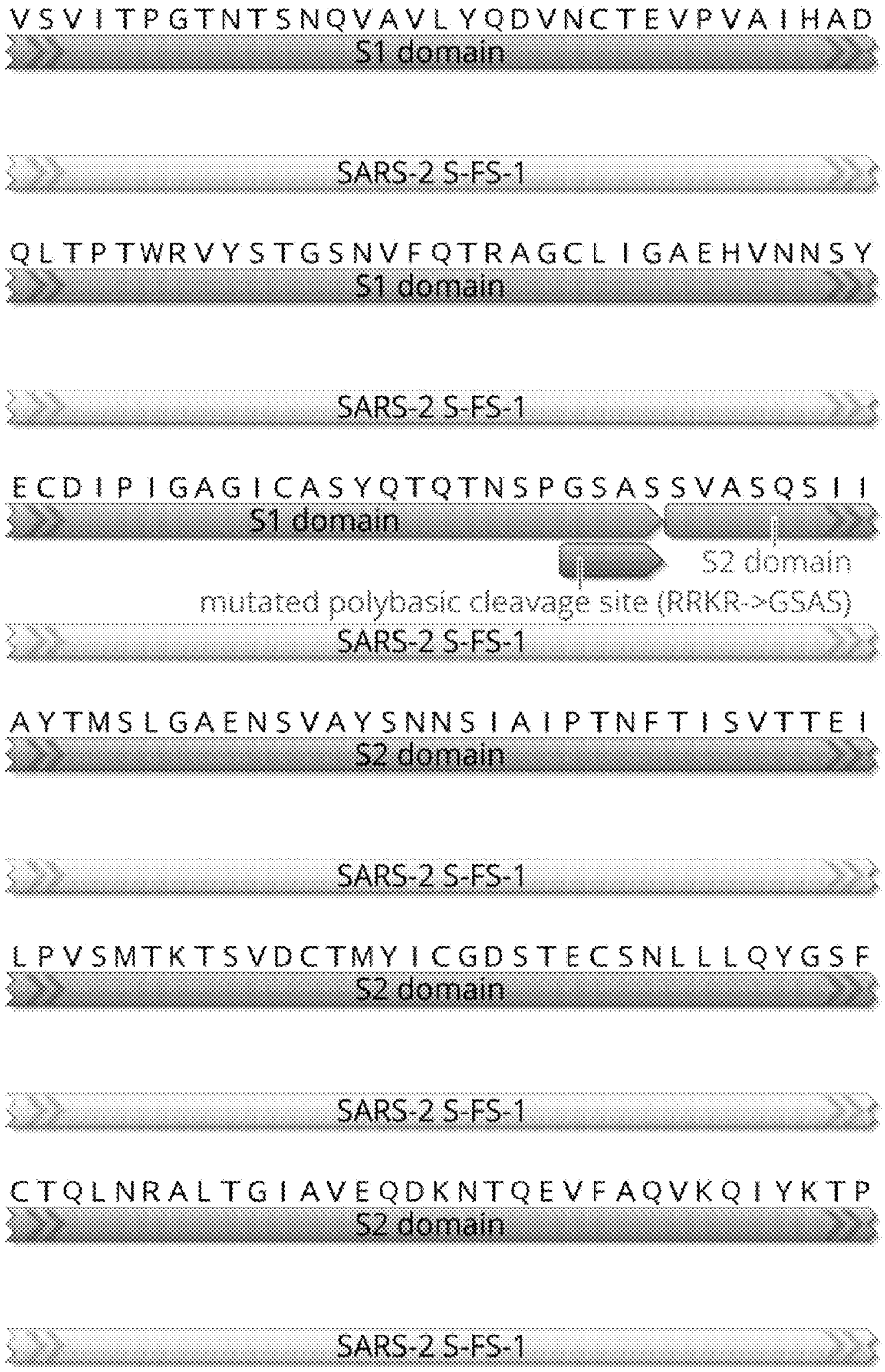
Figure 4:
Figure 4:
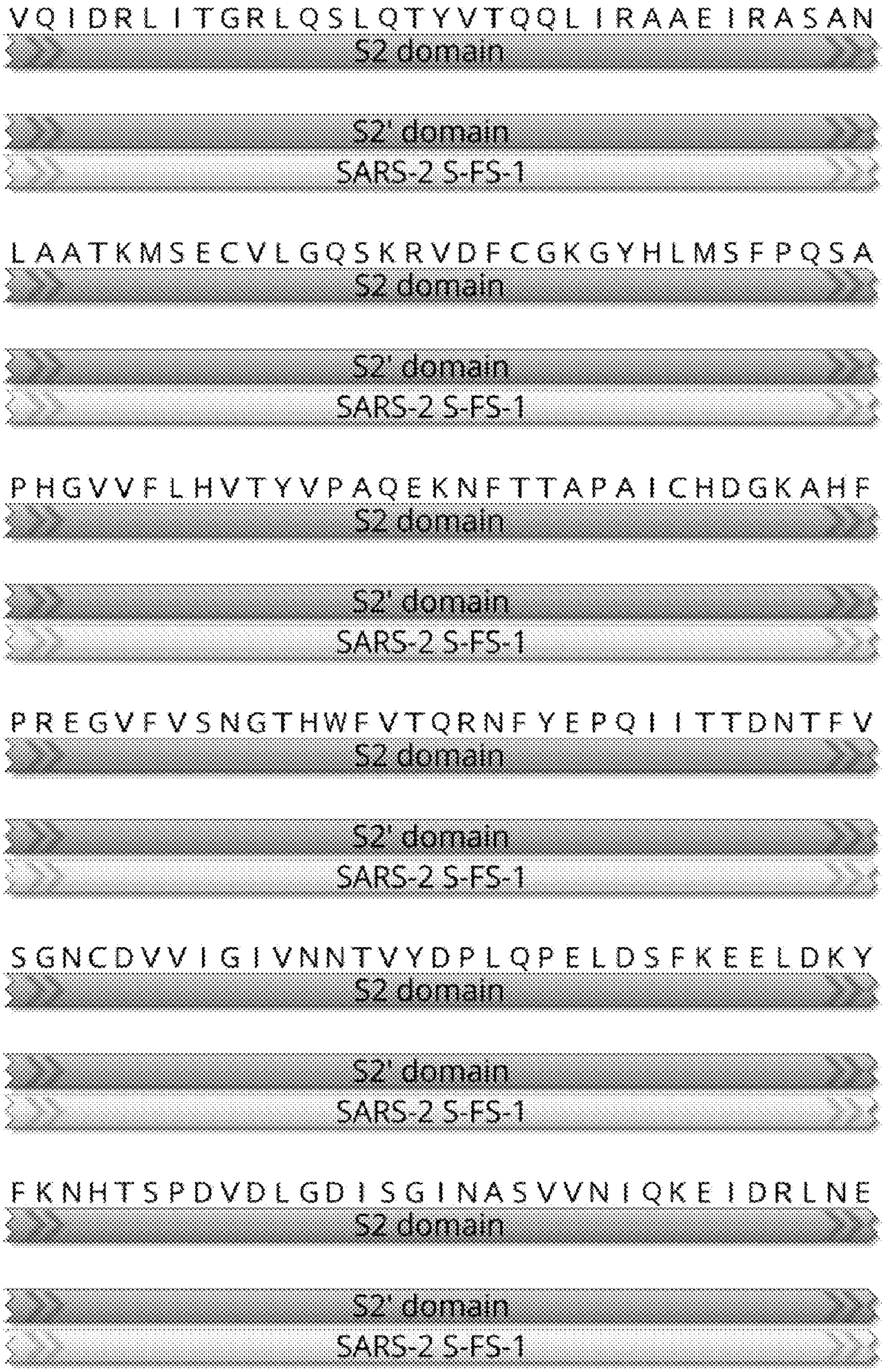
Figure 4:
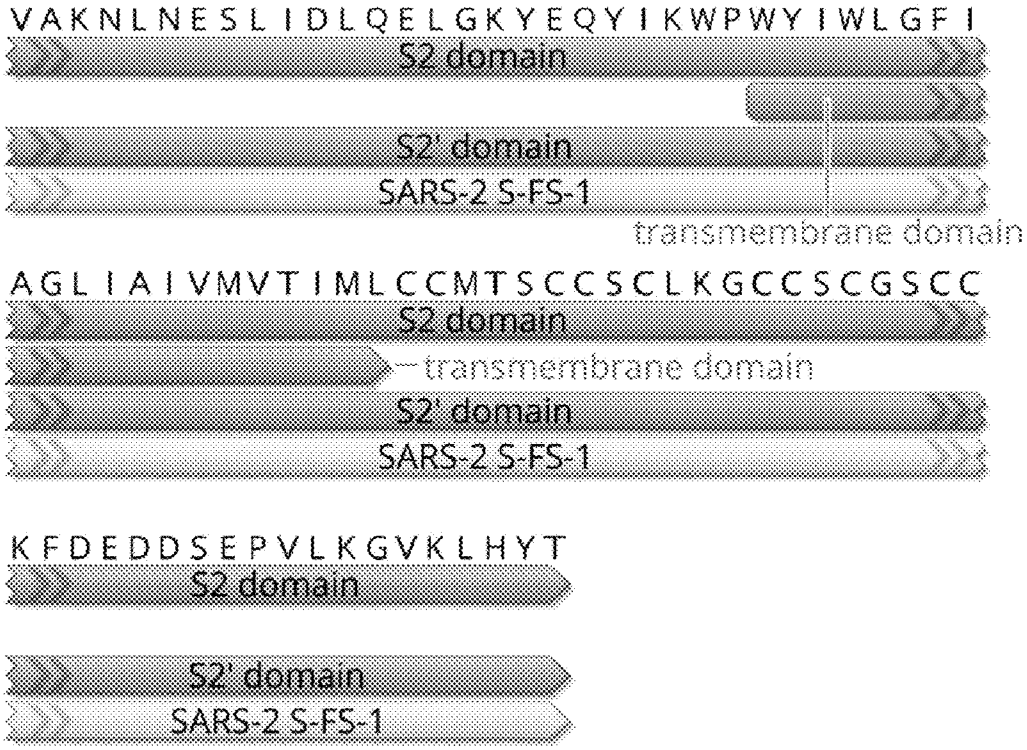

SEQ ID NO: 22 depicts the amino acid sequence of SARS-CoV-2 S full-length protein including modifications (K986P, V987P, and a GSAS amino acid stretch at the previous polybasic cleavage site) (see FIG. 4, "SARS-2 S-FS-1" minus "signal peptide").

SEQ ID NO: 23 depicts a nucleic acid sequence encoding SEQ ID NO: 22.

SEQ ID NO: 24 depicts the amino acid sequence of SARS-CoV-2 S full-length protein including modifications (K986P, V987P, GSAS amino acid stretch) plus the native signal peptide of SARS-CoV-2 S protein (see FIG. 4, referred to as "SARS-2 S-FS-1").

SEQ ID NO: 25 depicts a nucleic acid sequence encoding SEQ ID NO: 24.

SEQ ID NO: 26 depicts the nucleic acid sequence of Pr13.5long promoter.

SEQ ID NO: 27 depicts the nucleic acid sequence of Pr1328 promoter.

DESCRIPTION OF INVENTION

Herein, we describe SARS-CoV-2 antigens for eliciting an immune response in a vaccine recipient, e.g. a human, which are delivered through a recombinant MVA vaccine.

When designing the vaccine candidates, we devised two strategies to avoid immunopathological, disease-enhancing effects.

First, by designing a recombinant MVA expressing the SARS-CoV-2 S RBD that binds to the human ACE2 molecule, which serves as the viral receptor. It has been shown that the vast majority of monoclonal antibodies that were generated in mice against the SARS-CoV-1 RBD were neutralizing antibodies (He et al., 2006). Thus, the proportion of antibodies that merely bind to the S protein but do not neutralize SARS-CoV-2 (non-neutralizing S-binding antibodies) should be minimized when using the RBD only. In order to ensure efficient protein expression, short amino acid sequences were added N- and C-terminally to the RBD amino acid sequence (instead of using the full-length S protein) that are naturally located in the S1 domain adjacent to the RBD domain of the SARS-CoV-2 S protein. Furthermore, based on the publication of Chen et al. (2014) relating to SARS-CoV-1, one glycosylation site within the RBD of SARS-CoV-2 (asparagine 331) was also mutated to facilitate protein expression. Finally, in order to increase the production of neutralizing antibodies against the RBD, the protein was further modified N-terminally with a signal peptide to allow its efficient secretion.

This RBD approach was combined with a designer SARS-CoV-2-derived antigen that contains stretches of amino acid sequences from three SARS-CoV-2 viral proteins, i.e. protein 3a, envelope protein (E), and membrane glycoprotein (M), which have been shown and predicted to be rich in T cell epitopes. We avoided transmembrane domains and extracellular/extravirion domains of these molecules in the vaccine antigen to prevent induction of antibodies in a vaccine recipient that could bind to virus particles, on which these amino acid sequences would be exposed on the outer surface, and that might contribute to ADE. The RBD and 3aEM antigens are combined with promoters that drive very early but long-lasting expression by recombinant MVA and promote very efficient T cell and antibody responses.

Second, by expressing the full-length S protein of SARS CoV-2 using a recombinant MVA as vaccine, but in a form of S that is stabilized in its prefusion state. This is achieved by mutations in the spike protein, primarily by two single amino acids changed to prolines. Additionally, the polybasic furin protease cleavage site, i.e. amino acid residues RRAR, mutated to a GSAS stretch avoids furin-mediated proteolytic cleavage of the full-length S protein. These modifications reduce the formation of the post-fusion form of S and consequently reduce the induction of antibodies against this post fusion form of S that have low or no neutralizing activity. Thus, the ratio of non-neutralizing antibodies, which likely contribute most to ADE, to neutralizing antibodies will be lowered.

DEFINITIONS

It must be noted that, as used herein, the singular forms "a", "an", and "the", include plural references unless the context clearly indicates otherwise. Thus, for example, reference to "a nucleic acid sequence" includes one or more nucleic acid sequences.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

Throughout this specification and the appended claims, unless the context requires otherwise, the word "comprise", and variations such as "comprises" and "comprising", will be understood to imply the inclusion of a stated integer or step or group of integers or steps but not the exclusion of any other integer or step or group of integer or step. When used in the context of an aspect or embodiment in the description of the present invention the term "comprising" can be amended and thus replaced with the term "containing" or "including" or when used herein with the term "having." Similarly, any of the aforementioned terms (comprising, containing, including, having), whenever used in the context of an aspect or embodiment in the description of the present invention include, by virtue, the terms "consisting of" or "consisting essentially of," which each denotes specific legal meaning depending on jurisdiction.

When used herein "consisting of" excludes any element, step, or ingredient not specified in the claim element. When used herein, "consisting essentially of" does not exclude materials or steps that do not materially affect the basic and novel characteristics of the claim.

The term "virus" means viruses, virus particles and viral vectors. The term includes wild-type viruses, recombinant and non-recombinant viruses, live viruses and live-attenuated viruses.

The term "recombinant MVA" as described herein refers to an MVA comprising an exogenous nucleic acid sequence inserted in its genome, which is not naturally present in the parent virus. A recombinant MVA thus refers to MVA made by an artificial combination of two or more segments of nucleic acid sequence of synthetic or semisynthetic origin which does not occur in nature or is linked to another nucleic acid in an arrangement not found in nature. The artificial combination is most commonly accomplished by artificial manipulation of isolated segments of nucleic acids, using well-established genetic engineering techniques. Generally, a "recombinant MVA" as described herein refers to MVA that is produced by standard genetic engineering methods, e.g., a recombinant MVA is thus a genetically engineered or a genetically modified MVA. The term "recombinant MVA" thus includes MVA (e.g., MVA-BN) which has integrated at least one recombinant nucleic acid, preferably in the form of a transcriptional unit, in its genome. A transcriptional unit may include a promoter, enhancer, terminator and/or silencer. Recombinant MVA of the present invention may express heterologous antigenic determinants, polypeptides or proteins (antigens) upon induction of the regulatory elements e.g., the promoter.

The term "SARS-CoV-2 S full-length protein" refers to the complete S protein encompassing a transmembrane anchor and a cytoplasmic domain.

The term "original" relates to the SARS-CoV-2 reference strain, i.e. isolate Wuhan-Hu-1 (NC_045512.2), or proteins of this strain. Thus, "original SARS-CoV-2 protein sequence" relates to sequence YP_009724390.1 as depicted in SEQ ID NO: 1. Similarly, "the SARS-CoV-2 S full-length protein" relates to a protein according to SEQ ID NO:1.

The term "native" refers to an unmodified precursor protein or peptide. Thus, "native signal peptide" relates to a sequence as in YP_009724390.1.

The term "non-native proline residues" refers to proline residues not contained in a precursor protein, i.e. which are the result of an amino acid exchange.

The wording "corresponds to" when used in the context of a sequence means that the sequence is equivalent or identical to another sequence.

The wording "derives from" when used in the context of a sequence means that the sequence is modified or mutated as compared to a precursor sequence.

The term "prefusion state" or "prefusion conformation" refers to a structural state or conformation of the SARS-CoV-2 spike protein that is attained prior to a conformational change required to bring viral and cellular membranes into proximity for their fusion ("postfusion state").

The term "virion" refers to a virus particle comprising nucleic acid and, mostly, an envelope.

The wording "pharmaceutically acceptable" means that the carrier or excipient, at the dosages and concentrations employed, will substantially not cause unwanted or harmful effect in the subject to which they are administered. A "pharmaceutically acceptable carrier or excipient" is any inert substance that is combined with an active molecule such as a virus for preparing an agreeable or convenient dosage form.

The term "subject" (or "patient") refers to a vaccine recipient who typically is a mammal, such as a non-primate or a primate (e.g. monkey or human), and preferably is a human.

The term "homologous prime-boost vaccination" refers to a vaccination regimen in which the first (priming) administration and any subsequent boosting administration use the same recombinant MVA as described herein.

The term "heterologous prime-boost vaccination" refers to a vaccination regimen in which only the first (priming) administration or only a subsequent boosting administration uses a recombinant MVA as described herein.

ABBREVIATIONS

ACE2 angiotensin-converting enzyme 2
ADE antibody-dependent enhancement
COVID-19 coronavirus disease 19
hIgGH human IgG heavy chain
IGR intergenic region
MVA Modified Vaccinia Virus Ankara (MVA)
RBD receptor binding domain
SARS-CoV-2 severe acute respiratory syndrome-related coronavirus 2
S protein spike protein

EMBODIMENTS

The following antigens derived from SARS-CoV-2 and deliverable through a recombinant MVA are disclosed herein: a part of a SARS-CoV-2 S protein S1 domain, a SARS-CoV-2 S RBD, a SARS-CoV-2 3aEM antigen in the form of a fusion protein, and a SARS-CoV-2 S full-length protein modified to maintain a prefusion state.

Embodiments Relating to MVA Encoding a Part of a SARS-CoV-2 S Protein S1 Domain In one aspect, the invention provides a recombinant MVA comprising a nucleic acid sequence encoding an amino acid sequence of a part of a SARS-CoV-2 S protein S1 domain, which part comprises a SARS-CoV-2 S RBD.

In another aspect, the invention provides a DNA sequence, e.g. a plasmid, comprising a nucleic acid sequence encoding an amino acid sequence of a part of a SARS-CoV-2 S protein S1 domain, which part comprises a SARS-CoV-2 S RBD.

In one embodiment, the part of a SARS-CoV-2 S protein S1 domain, which part comprises a SARS-CoV-2 S RBD, corresponds to or derives from a part of the S1 domain of the original SARS-CoV-2 S protein sequence.

In one embodiment, the amino acid sequence of a part of a SARS-CoV-2 S protein S1 domain, which part comprises a SARS-CoV-2 S RBD, corresponds to or derives from amino acids no. 220-650, 270-600, 300-570, 319-549, or 310-530 of the original SARS-CoV-2 S protein sequence.

In one embodiment, the amino acid sequence of a part of a SARS-CoV-2 S protein S1 domain, which part comprises a SARS-CoV-2 S RBD, corresponds to or derives from amino acids no. 319-549 of the original SARS-CoV-2 S protein sequence.

In one embodiment, the amino acid sequence of a part of a SARS-CoV-2 S protein S1 domain, which part comprises a SARS-CoV-2 S RBD, comprises a further amino acid sequence adjacent to the SARS-CoV-2 S RBD amino acid sequence.

In one embodiment, the further amino acid sequence adjacent to the SARS-CoV-2 S RBD amino acid sequence is capable of ensuring efficient expression (or facilitating or enhancing expression) of SARS CoV-2 S RBD.

In one embodiment, the further amino acid sequence corresponds to or derives from an amino acid sequence adjacent to the SARS CoV-2 S RBD amino acid sequence within the original SARS-CoV-2 S protein sequence.

In one embodiment, the further amino acid sequence comprises or consists of 50, 30, 25, 20, 15, 12, 10, 7, 5, 3 or less amino acids, preferably 25 or 12 amino acids.

In one embodiment, the amino acid sequence of a part of a SARS-CoV-2 S protein S1 domain, which part comprises a SARS-CoV-2 S RBD, comprises a further first amino acid sequence adjacent N-terminally to the SARS-CoV-2 S RBD amino acid sequence, and a further second amino acid sequence adjacent C-terminally to the SARS-CoV-2 S RBD amino acid sequence.

In one embodiment, the further first and second amino acid sequences are capable of ensuring efficient expression (or facilitating or enhancing expression) of SARS CoV-2 S RBD.

In one embodiment, the further first amino acid sequence corresponds to or derives from an amino acid sequence adjacent N-terminally to the SARS CoV-2 S RBD amino acid sequence within the original SARS-CoV-2 S protein sequence.

In one embodiment, the further second amino acid sequence corresponds to or derives from an amino acid sequence adjacent C-terminally to the SARS CoV-2 S RBD amino acid sequence within the original SARS-CoV-2 S protein sequence.

In one embodiment, the further first amino acid sequence comprises or consists of 50, 30, 25, 20, 15, 12, 10, 7, 5, 3, or less amino acids, preferably 12 amino acids.

In one embodiment, the further second amino acid sequence comprises or consists of 50, 30, 25, 20, 15, 12, 10, 7, 5, 3, or less amino acids, preferably 25 amino acids.

In one embodiment, the amino acid sequence of a part of a SARS-CoV-2 S protein S1 domain, which part comprises a SARS-CoV-2 S RBD, is modified or mutated.

In one embodiment, the amino acid sequence of a part of a SARS-CoV-2 S protein S1 domain, which part comprises a SARS-CoV-2 S RBD, comprises a modification or mutation, preferably a substitution or an amino acid exchange.

In one embodiment, the amino acid sequence of a part of a SARS-CoV-2 S protein S1 domain, which part comprises a SARS-CoV-2 S RBD, comprises a substitution at amino acid no. 331 (or asparagine no. 331) of the original SARS-CoV-2 S protein sequence.

In one embodiment, the amino acid sequence of a part of a SARS-CoV-2 S protein S1 domain, which part comprises a SARS-CoV-2 S RBD, comprises an (N331A) exchange. Position 331 relates to the amino acid position in the original SARS-CoV-2 S protein sequence.

In one embodiment, the amino acid sequence of a part of a SARS-CoV-2 S protein S1 domain, which part comprises a SARS-CoV-2 S RBD, is as depicted in SEQ ID NO: 5.

In one embodiment, the amino acid sequence of a part of a SARS-CoV-2 S protein S1 domain, which part comprises a SARS-CoV-2 S RBD, is encoded by a nucleic acid sequence as depicted in SEQ ID NO: 6.

In one embodiment, the nucleic acid sequence encoding an amino acid sequence of a part of a SARS-CoV-2 S protein S1 domain, which part comprises a SARS-CoV-2 S RBD, is as depicted in SEQ ID NO: 6.

In one embodiment, the amino acid sequence of a part of a SARS-CoV-2 S protein S1 domain, which part comprises a SARS-CoV-2 S RBD, is capable of being secreted.

In one embodiment, the amino acid sequence of a part of a SARS-CoV-2 S protein S1 domain, which part comprises a SARS-CoV-2 S RBD, is N-terminally linked to a secretion signal peptide, preferably a secretion signal peptide derived from a human IgG heavy chain.

In one embodiment, the secretion signal peptide is as depicted in SEQ ID NO: 7.

In one embodiment, the secretion signal peptide is encoded by a nucleic acid sequence as depicted in SEQ ID NO: 8.

In one embodiment, the amino acid sequence of a part of a SARS-CoV-2 S protein S1 domain, which part comprises a SARS-CoV-2 S RBD, is as depicted in SEQ ID NO: 9.

In one embodiment, the amino acid sequence of a part of a SARS-CoV-2 S protein S1 domain, which part comprises a SARS-CoV-2 S RBD, is encoded by a nucleic acid sequence as depicted by SEQ ID NO: 10.

In one embodiment, the nucleic acid sequence encoding an amino acid sequence of a part of a SARS-CoV-2 S protein S1 domain, which part comprises a SARS-CoV-2 S RBD, is as depicted in SEQ ID NO: 10.

In one embodiment, the nucleotide sequence encoding an amino acid sequence of a part of a SARS-CoV-2 S protein S1 domain, which part comprises a SARS-CoV-2 S RBD, is operably linked to a Pr13.5long promoter for gene expression.

In one embodiment, the nucleotide sequence encoding an amino acid sequence of a part of a SARS-CoV-2 S protein S1 domain, which part comprises a SARS-CoV-2 S RBD, is inserted into MVA at intergenic region (IGR) site 64/65.

Embodiments Relating to MVA Encoding SARS-CoV-2 S RBD

In one aspect, the invention provides a recombinant MVA comprising a nucleic acid sequence encoding an amino acid sequence of a part of a SARS-CoV-2 S protein S1 domain, which part consists of a SARS-CoV-2 S RBD.

In another aspect, the invention provides a DNA sequence, e.g. a plasmid, comprising a nucleic acid sequence encoding an amino acid sequence of a part of a SARS-CoV-2 S protein S1 domain, which part consists of a SARS-CoV-2 S RBD.

In one embodiment, the nucleic acid sequence encodes an amino acid sequence of a SARS-CoV-2 S RBD.

In one embodiment, the amino acid sequence of a SARS-CoV-2 RBD corresponds to or derives from SARS-CoV-2 RBD of the original SARS-CoV-2 S protein sequence.

In one embodiment, the amino acid sequence of a SARS-CoV-2 S RBD is modified or mutated.

In one embodiment, the amino acid sequence of a SARS-CoV-2 S RBD comprises a modification or mutation, preferably a substitution or an amino acid exchange.

In one embodiment, the amino acid sequence of a SARS-CoV-2 S RBD comprises a substitution at amino acid no. 331 (or asparagine no. 331) of the original SARS-CoV-2 S protein sequence.

In one embodiment, the amino acid sequence of a SARS-CoV-2 S RBD comprises an (N331A) exchange. Position 331 relates to the amino acid position in the original SARS-CoV-2 S protein sequence.

In one embodiment, the amino acid sequence of a SARS-CoV-2 S RBD is as depicted in SEQ ID NO: 3.

In one embodiment, the amino acid sequence of a SARS-CoV-2 S RBD is encoded by a nucleic acid sequence as depicted in SEQ ID NO: 4.

In one embodiment, the nucleic acid sequence encoding an amino acid sequence of a SARS-CoV-2 S RBD is as depicted in SEQ ID NO: 4.

In one embodiment, the amino acid sequence of a SARS-CoV-2 S RBD is capable of being secreted.

In one embodiment, the amino acid sequence of a SARS-CoV-2 S RBD is N-terminally linked to a secretion signal peptide, preferably a secretion signal peptide derived from a human IgG heavy chain.

In one embodiment, the secretion signal peptide is as depicted in SEQ ID NO: 7.

In one embodiment, the secretion signal peptide is encoded by a nucleic acid sequence as depicted in SEQ ID NO: 8.

In one embodiment, the nucleic acid sequence encoding an amino acid sequence of a SARS-CoV-2 S RBD is operably linked to a Pr13.5long promoter for gene expression.

In one embodiment, the nucleic acid sequence encoding an amino acid sequence of a SARS-CoV-2 S RBD is inserted into MVA at intergenic region (IGR) site 64/65.

Embodiments Relating to MVA Encoding SARS-CoV-2 3aEM Fusion Protein

In one aspect, the invention provides a recombinant MVA comprising a nucleic acid sequence encoding an amino acid sequence of a SARS-CoV-2 fusion protein comprising two or more antigenic parts from one or more SARS-CoV-2 proteins, which parts are not naturally exposed on the surface of SARS-CoV-2 or a virion derived therefrom.

In another aspect, the invention provides a DNA sequence, e.g. a plasmid, comprising a nucleic acid sequence encoding an amino acid sequence of a fusion protein comprising two or more antigenic parts from one or more SARS-CoV-2 proteins, which parts are not naturally exposed on the surface of SARS-CoV-2 or a virion derived therefrom.

In one embodiment, the amino acid sequence of a SARS-CoV-2 fusion protein comprises one, two or more antigenic parts from one SARS-CoV-2 protein, which parts are not naturally exposed on the surface of SARS-CoV-2 or a virion derived therefrom.

In one embodiment, the amino acid sequence of a SARS-CoV-2 fusion protein comprises antigenic parts from two, three, or more SARS-CoV-2 proteins, which parts are not naturally exposed on the surface of SARS-CoV-2 or a virion derived therefrom.

In one embodiment, the amino acid sequence of a SARS-CoV-2 fusion protein comprises five different antigenic parts from SARS-CoV-2 proteins, preferably three SARS-CoV-2 proteins, which parts are not naturally exposed on the surface of SARS-CoV-2 or a virion derived therefrom.

In one embodiment, the two, three, or more SARS-CoV-2 proteins are structural proteins unrelated to SARS-CoV-2 S protein.

In one embodiment, the two, three, or more SARS-CoV-2 proteins are selected from the group consisting of a protein 3a, a protein E and a protein M.

In one embodiment, the amino acid sequence of a SARS-CoV-2 fusion protein comprises antigenic parts from SARS-CoV-2 protein 3a, protein E and protein M.

In one embodiment, the amino acid sequence of a SARS-CoV-2 fusion protein comprises two antigenic parts from a SARS-CoV-2 protein 3a.

In one embodiment, the amino acid sequence of a SARS-CoV-2 fusion protein comprises one antigenic part from a SARS-CoV-2 protein E.

In one embodiment, the amino acid sequence of a SARS-CoV-2 fusion protein comprises two antigenic parts from a SARS-CoV-2 protein M.

In one embodiment, the amino acid sequence of a SARS-CoV-2 fusion protein comprises two antigenic parts from a SARS-CoV-2 protein 3a, one antigenic part from a SARS-CoV-2 protein E, and two antigenic parts from a SARS-CoV-2 protein M.

In one embodiment, the antigenic part, or a first antigenic part, of a SARS-CoV-2 protein 3a (3a-1 fragment) is as depicted in SEQ ID NO: 14.

In one embodiment, the antigenic part, or a second antigenic part, of a SARS-CoV-2 protein 3a (3a-2 fragment) is as depicted in SEQ ID NO: 15.

In one embodiment, the antigenic part of a SARS-CoV-2 E protein is as depicted in SEQ ID NO: 16.

In one embodiment, the antigenic part, or a first antigenic part, of a SARS-CoV-2 protein M (M-1 fragment) is as depicted in SEQ ID NO: 17.

In one embodiment, the antigenic part, or a second antigenic part, of a SARS-CoV-2 protein M (M-2 fragment) is as depicted in SEQ ID NO: 18.

In one embodiment, the amino acid sequence of a SARS-CoV-2 fusion protein comprises an antigenic part selected from the group consisting of SEQ ID NO: 14, 15, 16, 17, and 18.

In one embodiment, the amino acid sequence of a SARS-CoV-2 fusion protein comprises the antigenic parts as depicted in SEQ ID NO: 14, 15, 16, 17, and 18.

In one embodiment, the amino acid sequence of a SARS-CoV-2 fusion protein comprises or consist of an amino acid sequence as depicted in SEQ ID NO: 19.

In one embodiment, the amino acid sequence of a SARS-CoV-2 fusion protein is modified or mutated.

In one embodiment, the amino acid sequence of a SARS-CoV-2 fusion protein comprises a modification or mutation, preferably a substitution or amino acid exchange.

In one embodiment, the amino acid sequence of a SARS-CoV-2 fusion protein comprises a modification at or near a junction between the antigenic parts from two SARS-CoV-2 proteins.

In one embodiment, the amino acid sequence of a SARS-CoV-2 fusion protein comprises a modification capable of preventing a neoepitope formation at or near a junction between the antigenic parts from two SARS-CoV-2 proteins.

In one embodiment, the amino acid sequence of a SARS-CoV-2 fusion protein consists of 297 amino acids and comprises substitutions at amino acids no. 131, 132, 179, and 180 of the fusion protein, preferably a SARS-CoV-2 fusion protein as depicted in SEQ ID NO: 19.

In one embodiment, the amino acid sequence of a SARS-CoV-2 fusion protein comprises an amino acid sequence consisting of 297 amino acids and comprising substitutions at amino acids no. 131, 132, 179, and 180 of the fusion protein, preferably a SARS-CoV-2 fusion protein as depicted in SEQ ID NO: 19.

In one embodiment, the amino acid sequence of a SARS-CoV-2 fusion protein consists of 297 amino acids and comprises (A131W), (Y132F), (S179D), and (Y180F) exchanges, preferably in a SARS-CoV-2 fusion protein as depicted in SEQ ID NO: 19.

In one embodiment, the amino acid sequence of a SARS-CoV-2 fusion protein comprises an amino acid sequence consisting of 297 amino acids and comprising (A131W), (Y132F), (S179D), and (Y180F) exchanges, preferably in a SARS-CoV-2 fusion protein as depicted in SEQ ID NO:19.

In one embodiment, the amino acid sequence of a SARS-CoV-2 fusion protein is as depicted in SEQ ID NO: 20.

In one embodiment, the amino acid sequence of a SARS-CoV-2 fusion protein is encoded by a nucleic acid sequence as depicted in SEQ ID NO: 21.

In one embodiment, the nucleic acid sequence encoding an amino acid sequence of a SARS-CoV-2 fusion protein is as depicted in SEQ ID NO: 21.

In one embodiment, the expressed SARS-CoV-2 fusion protein is localized in the cytoplasm of an infected cell.

In one embodiment, the nucleotide sequence encoding an amino acid sequence of a SARS-CoV-2 fusion protein is operably linked to a Pr13.5long promoter for gene expression, preferably to a promoter as depicted in SEQ ID NO: 26.

In one embodiment, the nucleotide sequence encoding an amino acid sequence of a SARS-CoV-2 fusion protein is inserted into MVA at intergenic region (IGR) site 64/65.

In one embodiment, the nucleotide sequence encoding an amino acid sequence of a SARS-CoV-2 fusion protein and the nucleotide sequence encoding an amino acid sequence of a part of a SARS-CoV-2 S protein S1 domain (as specified above) are contained together in the same recombinant MVA, preferably are contained together in one expression cassette.

In one embodiment, the expression cassette containing the nucleotide sequence encoding an amino acid sequence of a SARS-CoV-2 fusion protein and the nucleotide sequence encoding an amino acid sequence of a part of a SARS-CoV-2 S protein S1 domain (as specified above) is inserted into MVA at intergenic region (IGR) site 64/65.

Embodiments Relating to MVA Encoding SARS-CoV-2 S Full-Length Protein

In one aspect, the invention provides a recombinant MVA comprising a nucleic acid sequence encoding an amino acid sequence of a SARS-CoV-2 S full-length protein.

In one embodiment, the SARS-CoV-2 S full-length protein corresponds to or derives from the original SARS-CoV-2 S protein sequence.

In one embodiment, the amino acid sequence of a SARS-CoV-2 S full-length protein is modified or mutated.

In one embodiment, the amino acid sequence of a SARS-CoV-2 S full-length protein comprises a modification or mutation, preferably a substitution or amino acid exchange.

In one embodiment, the amino acid sequence of a SARS-CoV-2 S full-length protein comprises a modification which is capable of stabilizing the S protein in a prefusion conformation.

In one embodiment, the amino acid sequence of a SARS-CoV-2 S full-length protein comprises two consecutive non-native proline residues.

In one embodiment, the amino acid sequence of a SARS-CoV-2 S full-length protein comprises a non-native proline residue each at amino acid no. 986 and no. 987 of the original SARS-CoV-2 S protein sequence.

In one embodiment, the amino acid sequence of a SARS-CoV-2 S full-length protein comprises a (K986P) and (V987P) exchange. Positions 986 and 987 relate to the amino acid positions in the original SARS-CoV-2 S protein sequence.

In one embodiment, the amino acid sequence of a SARS-CoV-2 S full-length protein comprises a further modification or mutation, preferably a further substitution or amino acid exchange.

In one embodiment, the amino acid sequence of a SARS-CoV-2 S full-length protein comprises a further modification which is capable of, or contributes to, stabilizing the S protein in a prefusion conformation.

In one embodiment, the amino acid sequence of a SARS-CoV-2 S full-length protein comprises a further modification capable of preventing proteolytic cleavage of the full-length protein, preferably capable of preventing proteolytic cleavage of the full-length protein by a furin-like protease or at a furin cleavage site.

In one embodiment, the amino acid sequence of a SARS-CoV-2 S full-length protein comprises a substitution of consecutive amino acids RRAR resulting in amino acid stretch GSAS at a furin cleavage site, preferably at amino acids no. 682-685 of the original SARS-CoV-2 S protein sequence.

In one embodiment, the amino acid sequence of a SARS-CoV-2 S full-length protein comprises two consecutive non-native proline residues and a substitution of consecutive amino acids RRAR resulting in amino acid stretch GSAS at a furin cleavage site, preferably at amino acids no. 682-685 of the original SARS-CoV-2 S protein sequence, more preferably (R682G), (R683S), (R685S) amino acid exchanges.

In one embodiment, the amino acid sequence of a SARS-CoV-2 S full-length protein comprises a non-native proline residue each at amino acids no. 986 and 987 of the original SARS-CoV-2 S protein, and a substitution of consecutive amino acids RRAR resulting in amino acid stretch GSAS at a furin cleavage site, preferably a substitution of consecutive amino acids RRAR at amino acids no. 682-685 of the original SARS-CoV-2 S protein sequence, more preferably (R682G), (R683S), (R685S) amino acid exchanges.

In one embodiment, the amino acid sequence of a SARS-CoV-2 S full-length protein is as depicted in SEQ ID NO: 1.

In one embodiment, the amino acid sequence of a SARS-CoV-2 S full-length protein is encoded by a nucleic acid sequence as depicted in SEQ ID NO: 2.

In one embodiment, the nucleic acid sequence encoding an amino acid sequence of a SARS-CoV-2 S full-length protein is as depicted in SEQ ID NO: 2.

In one embodiment, the amino acid sequence of a SARS-CoV-2 S full-length protein is as depicted in SEQ ID NO: 22.

In one embodiment, the amino acid sequence of a SARS-CoV-2 S full-length protein is encoded by a nucleic acid sequence as depicted in SEQ ID NO: 23.

In one embodiment, the nucleic acid sequence encoding an amino acid sequence of a SARS-CoV-2 S full-length protein is as depicted in SEQ ID NO: 23.

In one embodiment, the amino acid sequence of a SARS-CoV-2 S full-length protein is capable of being secreted.

In one embodiment, the amino acid sequence of a SARS-CoV-2 S full-length protein as depicted in SEQ ID NO: 22 is linked to a secretion signal peptide, preferably a secretion signal peptide which is, corresponds to or derives from, the signal peptide of the original SARS-CoV-2 S protein sequence.

In one embodiment, the amino acid sequence of a SARS-CoV-2 S full-length protein is as depicted in SEQ ID NO: 24.

In one embodiment, the amino acid sequence of a SARS-CoV-2 S full-length protein is encoded by a nucleic acid as depicted in SEQ ID NO: 25.

In one embodiment, the nucleic acid sequence encoding an amino acid sequence of a SARS-CoV-2 S full-length protein is as depicted in SEQ ID NO: 25.

In one embodiment, the nucleotide sequence encoding an amino acid sequence of a SARS-CoV-2 S full-length protein is operably linked to a Pr13.5long promoter for gene expression.

In one embodiment, the nucleotide sequence encoding an amino acid sequence of a SARS-CoV-2 S full-length protein is inserted into MVA at intergenic region (IGR) site 64/65.

In one embodiment, the invention provides a recombinant MVA comprising a nucleic acid sequence encoding an amino acid sequence of a SARS-CoV-2 S full-length protein as described herein, wherein the recombinant MVA is capable of inducing an antigen specific T cell response, preferably a CD8 T cell response, against SARS-CoV-2 S full-length protein, or a part thereof or an antigenic determinant thereof, preferably against an RBD, or a part thereof or an antigenic determinant thereof.

In one embodiment, the invention provides a recombinant MVA comprising a nucleic acid sequence encoding an amino acid sequence of a SARS-CoV-2 S full-length protein as described herein, wherein the recombinant MVA is capable of inducing antigen binding antibodies against SARS-CoV-2 S full-length protein, or a part thereof or an antigenic determinant thereof, preferably against an RBD, or a part thereof or an antigenic determinant thereof.

In one embodiment, the invention provides a recombinant MVA comprising a nucleic acid sequence encoding an amino acid sequence of a SARS-CoV-2 S full-length protein as described herein, wherein the recombinant MVA is capable of inducing antigen specific B cells against the SARS-CoV-2 S full-length protein, or a part thereof or an antigenic determinant thereof, preferably against an RBD, or a part thereof or an antigenic determinant thereof.

Embodiments Relating to a Part of a SARS-CoV-2 S Protein S1 Domain

In one aspect, the invention provides an amino acid sequence of a part of a SARS-CoV-2 S protein S1 domain, which part comprises a SARS-CoV-2 S RBD, preferably a modified or mutated SARS-CoV-2 S RBD.

In another aspect, the invention provides a nucleic acid sequence encoding an amino acid sequence of a part of a SARS-CoV-2 S protein S1 domain, which part comprises a SARS-CoV-2 S RBD, preferably a modified or mutated SARS-CoV-2 S RBD.

In one embodiment, the part of a SARS-CoV-2 S protein S1 domain, which part comprises a SARS-CoV-2 S RBD, corresponds to or derives from a part of the S1 domain of the original SARS-CoV-2 S protein sequence.

In one embodiment, the amino acid sequence of a part of a SARS-CoV-2 S protein S1 domain, which part comprises a SARS-CoV-2 S RBD, corresponds to or derives from amino acids no. 220-650, 270-600, 300-570, 319-549, or 310-530 of the original SARS-CoV-2 S protein sequence.

In one embodiment, the amino acid sequence of a part of a SARS-CoV-2 S protein S1 domain, which part comprises a SARS-CoV-2 S RBD, corresponds to or derives from amino acids no. 319-549 of the original SARS-CoV-2 S protein sequence.

In one embodiment, the amino acid sequence of a part of a SARS-CoV-2 S protein S1 domain, which part comprises a SARS-CoV-2 S RBD, comprises a further amino acid sequence adjacent to the SARS-CoV-2 S RBD amino acid sequence.

In one embodiment, the further amino acid sequence adjacent to the SARS-CoV-2 S RBD amino acid sequence is capable of ensuring efficient expression (or facilitating or enhancing expression) expression of SARS CoV-2 S RBD.

In one embodiment, the further amino acid sequence corresponds to or derives from an amino acid sequence adjacent to the SARS CoV-2 S RBD amino acid sequence within the original SARS-CoV-2 S protein sequence.

In one embodiment, the further amino acid sequence comprises or consists of 50, 30, 25, 20, 15, 12, 10, 7, 5, 3 or less amino acids, preferably 25 or 12 amino acids.

In one embodiment, the amino acid sequence of a part of a SARS-CoV-2 S protein S1 domain, which part comprises a SARS-CoV-2 S RBD, comprises a further first amino acid sequence adjacent N-terminally to the SARS-CoV-2 S RBD amino acid sequence, and a further second amino acid sequence adjacent C-terminally to the SARS-CoV-2 S RBD amino acid sequence.

In one embodiment, the further first and second amino acid sequences are capable of ensuring efficient expression (or facilitating or enhancing expression) of SARS CoV-2 S RBD.

In one embodiment, the further first amino acid sequence corresponds to or derives from an amino acid sequence adjacent N-terminally to the SARS CoV-2 S RBD amino acid sequence within the original SARS-CoV-2 S protein sequence.

In one embodiment, the further second amino acid sequence corresponds to or derives from an amino acid sequence adjacent C-terminally to the SARS CoV-2 S RBD amino acid sequence within the original SARS-CoV-2 S protein sequence.

In one embodiment, the further first amino acid sequence comprises or consists of 50, 30, 25, 20, 15, 12, 10, 7, 5, 3, or less amino acids, preferably 12 amino acids.

In one embodiment, the further second amino acid sequence comprises or consists of 50, 30, 25, 20, 15, 12, 10, 7, 5, 3, or less amino acids, preferably 25 amino acids.

In one embodiment, the amino acid sequence of a part of a SARS-CoV-2 S protein S1 domain, which part comprises a SARS-CoV-2 S RBD, is modified or mutated.

In one embodiment, the amino acid sequence of a part of a SARS-CoV-2 S protein S1 domain, which part comprises a SARS-CoV-2 S RBD, comprises a modification or mutation, preferably a substitution or an amino acid exchange.

In one embodiment, the amino acid sequence of a part of a SARS-CoV-2 S protein S1 domain, which part comprises a SARS-CoV-2 S RBD, comprises a substitution at amino acid no. 331 (or asparagine no. 331) of the original SARS-CoV-2 S protein sequence.

In one embodiment, the amino acid sequence of a part of a SARS-CoV-2 S protein S1 domain, which part comprises a SARS-CoV-2 S RBD, comprises an (N331A) exchange. Position 331 relates to the amino acid position in the original SARS-CoV-2 S protein sequence.

In one embodiment, the amino acid sequence of a part of a SARS-CoV-2 S protein S1 domain, which part comprises a SARS-CoV-2 S RBD, is as depicted in SEQ ID NO: 5.

In one embodiment, the amino acid sequence of a part of a SARS-CoV-2 S protein S1 domain, which part comprises a SARS-CoV-2 S RBD, is encoded by a nucleic acid sequence as depicted in SEQ ID NO: 6.

In one embodiment, the nucleic acid sequence encoding an amino acid sequence of a part of a SARS-CoV-2 S protein S1 domain, which part comprises a SARS-CoV-2 S RBD, is as depicted in SEQ ID NO: 6.

In one embodiment, the amino acid sequence of a part of a SARS-CoV-2 S protein S1 domain, which part comprises a SARS-CoV-2 S RBD, is capable of being secreted.

In one embodiment, the amino acid sequence of a part of a SARS-CoV-2 S protein S1 domain, which part comprises a SARS-CoV-2 S RBD, is N-terminally linked to a secretion signal peptide, preferably a secretion signal peptide derived from a human IgG heavy chain.

In one embodiment, the secretion signal peptide is as depicted in SEQ ID NO: 7.

In one embodiment, the secretion signal peptide is encoded by a nucleic acid sequence as depicted in SEQ ID NO: 8.

In one embodiment, the amino acid sequence of a part of a SARS-CoV-2 S protein S1 domain, which part comprises a SARS-CoV-2 S RBD, is as depicted in SEQ ID NO: 9.

In one embodiment, the amino acid sequence of a part of a SARS-CoV-2 S protein S1 domain, which part comprises a SARS-CoV-2 S RBD, is encoded by a nucleic acid sequence as depicted by SEQ ID NO: 10.

In one embodiment, the nucleic acid sequence encoding an amino acid sequence of a part of a SARS-CoV-2 S protein S1 domain, which part comprises a SARS-CoV-2 S RBD, is as depicted in SEQ ID NO: 10.

In one embodiment, the nucleotide sequence encoding an amino acid sequence of a part of a SARS-CoV-2 S protein S1 domain, which part comprises a SARS-CoV-2 S RBD, is operably linked to a Pr13.5long promoter for gene expression.

Embodiments Relating to SARS-CoV-2 S RBD

In one aspect, the invention provides an amino acid sequence of a part of a SARS-CoV-2 S protein S1 domain, which part consists of a SARS-CoV-2 S RBD, preferably a modified or mutated SARS-CoV-2 S RBD.

In another aspect, the invention provides a nucleic acid sequence encoding an amino acid sequence of a part of a SARS-CoV-2 S protein S1 domain, which part consists of a SARS-CoV-2 S RBD, preferably a modified or mutated SARS-CoV-2 S RBD.

In a further aspect, the invention provides an amino acid sequence comprising an amino acid sequence of a SARS-CoV-2 S RBD, preferably a modified or mutated SARS-CoV-2 S RBD.

In yet another aspect, the invention provides a nucleic acid comprising a nucleic acid sequence encoding an amino acid sequence of a SARS-CoV-2 S RBD, preferably a modified or mutated SARS-CoV-2 S RBD.

In one embodiment, the amino acid sequence of a SARS-CoV-2 RBD derives from SARS-CoV-2 RBD of the original SARS-CoV-2 S protein sequence.

In one embodiment, the amino acid sequence of a SARS-CoV-2 S RBD is modified or mutated.

In one embodiment, the amino acid sequence of a SARS-CoV-2 S RBD comprises a modification or mutation, preferably a substitution or an amino acid exchange.

In one embodiment, the amino acid sequence of a SARS-CoV-2 S RBD comprises a substitution at amino acid no. 331 (or asparagine no. 331) of the original SARS-CoV-2 S protein sequence.

In one embodiment, the amino acid sequence of a SARS-CoV-2 S RBD comprises an (N331A) exchange. Position 331 relates to the amino acid position in the original SARS-CoV-2 S protein sequence.

In one embodiment, the amino acid sequence of a SARS-CoV-2 S RBD is as depicted in SEQ ID NO: 3.

In one embodiment, the amino acid sequence of a SARS-CoV-2 S RBD is encoded by a nucleic acid sequence as depicted in SEQ ID NO: 4.

In one embodiment, the nucleic acid sequence encoding an amino acid sequence of a SARS-CoV-2 S RBD is as depicted in SEQ ID NO: 4.

In one embodiment, the amino acid sequence of a SARS-CoV-2 S RBD is capable of being secreted.

In one embodiment, the amino acid sequence of a SARS-CoV-2 S RBD is N-terminally linked to a secretion signal peptide, preferably a secretion signal peptide derived from a human IgG heavy chain.

In one embodiment, the secretion signal peptide is as depicted in SEQ ID NO: 7.

In one embodiment, the secretion signal peptide is encoded by a nucleic acid sequence as depicted in SEQ ID NO: 8.

In one embodiment, the nucleic acid sequence encoding an amino acid sequence of a SARS-CoV-2 S RBD is operably linked to a Pr13.5long promoter for gene expression.

Embodiments Relating to SARS-CoV-2 3aEM Fusion Protein

In one aspect, the invention provides an amino acid sequence of a SARS-CoV-2 fusion protein comprising two or more antigenic parts from one or more SARS-CoV-2 proteins, which parts are not naturally exposed on the surface of SARS-CoV-2 or a virion derived therefrom.

In another aspect, the invention provides a nucleic acid sequence encoding an amino acid sequence of a SARS-CoV-2 fusion protein comprising two or more antigenic parts from one or more SARS-CoV-2 proteins, which parts are not naturally exposed on the surface of SARS-CoV-2 or a virion derived therefrom.

In a further aspect, the invention provides a SARS-CoV-2 fusion protein comprising an amino acid sequence comprising two or more antigenic parts from one or more SARS-CoV-2 proteins, which parts are not naturally exposed on the surface of SARS-CoV-2 or a virion derived therefrom.

In one embodiment, the amino acid sequence of a SARS-CoV-2 fusion protein comprises one, two or more antigenic parts from one SARS-CoV-2 protein, which parts are not naturally exposed on the surface of SARS-CoV-2 or a virion derived therefrom.

In one embodiment, the amino acid sequence of a SARS-CoV-2 fusion protein comprises antigenic parts from two, three, or more SARS-CoV-2 proteins, which parts are not naturally exposed on the surface of SARS-CoV-2 or a virion derived therefrom.

In one embodiment, the amino acid sequence of a SARS-CoV-2 fusion protein comprises five different antigenic parts from SARS-CoV-2 proteins, preferably three SARS-CoV-2 protein, which parts are not naturally exposed on the surface of SARS-CoV-2 or a virion derived therefrom.

In one embodiment, the two, three, or more SARS-CoV-2 proteins are structural proteins unrelated to SARS-CoV-2 S protein.

In one embodiment, the two, three, or more SARS-CoV-2 proteins are selected from the group consisting of a protein 3a, a protein E and a protein M.

In one embodiment, the amino acid sequence of a SARS-CoV-2 fusion protein comprises antigenic parts from SARS-CoV-2 protein 3a, protein E and protein M.

In one embodiment, the amino acid sequence of a SARS-CoV-2 fusion protein comprises two antigenic parts from a SARS-CoV-2 protein 3a.

In one embodiment, the amino acid sequence of a SARS-CoV-2 fusion protein comprises one antigenic part from a SARS-CoV-2 protein E.

In one embodiment, the amino acid sequence of a SARS-CoV-2 fusion protein comprises two antigenic parts from a SARS-CoV-2 protein M.

In one embodiment, the amino acid sequence of a SARS-CoV-2 fusion protein comprises two antigenic parts from a SARS-CoV-2 protein 3a, one antigenic part from a SARS-CoV-2 protein E, and two antigenic parts from a SARS-CoV-2 protein E.

In one embodiment, the antigenic part, or a first antigenic part, of a SARS-CoV-2 protein 3a (3a-1 fragment) is as depicted in SEQ ID NO: 14.

In one embodiment, the antigenic part, or a second antigenic part, of a SARS-CoV-2 protein 3a (3a-2 fragment) is as depicted in SEQ ID NO: 15.

In one embodiment, the antigenic part of a SARS-CoV-2 E protein is as depicted in SEQ ID NO: 16.

In one embodiment, the antigenic part, or a first antigenic part, of a SARS-CoV-2 protein M (M-1 fragment) is as depicted in SEQ ID NO: 17.

In one embodiment, the antigenic part, or a second antigenic part, of a SARS-CoV-2 protein M (M-2 fragment) is as depicted in SEQ ID NO: 18.

In one embodiment, the amino acid sequence of a SARS-CoV-2 fusion protein comprises an antigenic part selected from the group consisting of SEQ ID NO: 14, 15, 16, 17, and 18.

In one embodiment, the amino acid sequence of a SARS-CoV-2 fusion protein comprises the antigenic parts as depicted in SEQ ID NO: 14, 15, 16, 17, and 18.

In one embodiment, the amino acid sequence of a SARS-CoV-2 fusion protein comprises or consists of an amino acid sequence as depicted in SEQ ID NO: 19.

In one embodiment, the amino acid sequence of a SARS-CoV-2 fusion protein is modified or mutated.

In one embodiment, the amino acid sequence of a SARS-CoV-2 fusion protein comprises a modification or mutation, preferably a substitution or amino acid exchange.

In one embodiment, the amino acid sequence of a SARS-CoV-2 fusion protein comprises a modification at or near a junction between the antigenic parts from two SARS-CoV-2 proteins.

In one embodiment, the amino acid sequence of a SARS-CoV-2 fusion protein comprises a modification capable of preventing a neoepitope formation at or near a junction between the antigenic parts from two SARS-CoV-2 proteins.

In one embodiment, the amino acid sequence of a SARS-CoV-2 fusion protein consists of 297 amino acids and comprises substitutions at amino acids no. 131, 132, 179, and 180 of the fusion protein, preferably a SARS-CoV-2 fusion protein as depicted in SEQ ID NO: 19.

In one embodiment, the amino acid sequence of a SARS-CoV-2 fusion protein comprises an amino acid sequence consisting of 297 amino acids and comprising substitutions at amino acids no. 131, 132, 179, and 180 of the fusion protein, preferably a SARS-CoV-2 fusion protein as depicted in SEQ ID NO: 19.

In one embodiment, the amino acid sequence of a SARS-CoV-2 fusion protein consists of 297 amino acids and comprises (A131W), (Y132F), (S179D), and (Y180F) exchanges, preferably in a SARS-CoV-2 fusion protein as depicted in SEQ ID NO: 19.

In one embodiment, the amino acid sequence of a SARS-CoV-2 fusion protein comprises an amino acid sequence consisting of 297 amino acids and comprising (A131W), (Y132F), (S179D), and (Y180F) exchanges, preferably in a SARS-CoV-2 fusion protein as depicted in SEQ ID NO: 19.

In one embodiment, the amino acid sequence of a SARS-CoV-2 fusion protein is as depicted in SEQ ID NO: 20.

In one embodiment, the amino acid sequence of a SARS-CoV-2 fusion protein is encoded by a nucleic acid sequence as depicted in SEQ ID NO: 21.

In one embodiment, the nucleic acid sequence encoding an amino acid sequence of a SARS-CoV-2 fusion protein is as depicted in SEQ ID NO: 21.

In one embodiment, the nucleotide sequence encoding an amino acid sequence of a SARS-CoV-2 fusion protein is operably linked to a Pr13.5long promoter for gene expression.

Embodiments Relating to SARS-CoV-2 S Full-Length Protein

In one aspect, the invention provides an amino acid sequence of a SARS-CoV-2 S full-length protein comprising two consecutive non-native proline residues.

In another aspect, the invention provides a nucleic acid sequence encoding an amino acid sequence of a SARS-CoV-2 S full-length protein comprising two consecutive non-native proline residues.

In one embodiment, the SARS-CoV-2 S full-length protein derives from the original SARS-CoV-2 S protein sequence.

In one embodiment, the amino acid sequence of a SARS-CoV-2 S full-length protein comprises a non-native proline residue each at amino acid no. 986 and no. 987 of the original SARS-CoV-2 S protein sequence.

In one embodiment, the amino acid sequence of a SARS-CoV-2 S full-length protein comprises a (K986P) and (V987P) exchange. Positions 986 and 987 relate to amino acid positions in the original SARS-CoV-2 S protein sequence.

In one embodiment, the amino acid sequence of a SARS-CoV-2 S full-length protein comprises a further modification or mutation, preferably a further substitution or amino acid exchange.

In one embodiment, the amino acid sequence of a SARS-CoV-2 S full-length protein comprises a further modification which is capable of, or contributes to, stabilizing the S protein in a prefusion conformation.

In one embodiment, the amino acid sequence of a SARS-CoV-2 S full-length protein comprises a further modification capable of preventing proteolytic cleavage of the full-length protein, preferably capable of preventing proteolytic cleavage of the full-length protein by a furin-like protease or at a furin cleavage site.

In one embodiment, the amino acid sequence of a SARS-CoV-2 S full-length protein comprises a substitution of consecutive amino acids RRAR resulting in amino acid stretch GSAS at a furin cleavage site, preferably at amino acids no. 682-685 of the original SARS-CoV-2 S protein sequence.

In one embodiment, the amino acid sequence of a SARS-CoV-2 S full-length protein comprises two consecutive non-native proline residues and a substitution of consecutive amino acids RRAR resulting in amino acid stretch GSAS at a furin cleavage site, preferably at amino acids no. 682-685 of the original SARS-CoV-2 S protein sequence.

In one embodiment, the amino acid sequence of a SARS-CoV-2 S full-length protein comprises a non-native proline residue each at amino acids no. 986 and 987 of the original SARS-CoV-2 S protein, and a substitution of consecutive amino acids RRAR resulting in amino acid stretch GSAS at a furin cleavage site, preferably at amino acids no. 682-685 of the original SARS-CoV-2 S protein sequence, more preferably (R682G), (R683S), (R685S) amino acid exchanges.

In one embodiment, the amino acid sequence of a SARS-CoV-2 S full-length protein is as depicted in SEQ ID NO: 22.

In one embodiment, the amino acid sequence of a SARS-CoV-2 S full-length protein is encoded by a nucleic acid sequence as depicted in SEQ ID NO: 23.

In one embodiment, the nucleic acid sequence encoding an amino acid sequence of a SARS-CoV-2 S full-length protein is as depicted in SEQ ID NO: 23.

In one embodiment, the amino acid sequence of a SARS-CoV-2 S full-length protein is capable of being secreted.

In one embodiment, the amino acid sequence of a SARS-CoV-2 S full-length protein as depicted in SEQ ID NO: 22 is linked to a secretion signal peptide, preferably a secretion signal peptide which is, corresponds to or derives from, the signal peptide of the original SARS-CoV-2 S protein sequence.

In one embodiment, the amino acid sequence of a SARS-CoV-2 S full-length protein is as depicted in SEQ ID NO: 24.

In one embodiment, the amino acid sequence of a SARS-CoV-2 S full-length protein is encoded by a nucleic acid as depicted in SEQ ID NO: 25.

In one embodiment, the nucleic acid sequence encoding an amino acid sequence of a SARS-CoV-2 S full-length protein is as depicted in SEQ ID NO: 25.

In one embodiment, the nucleotide sequence encoding an amino acid sequence of a SARS-CoV-2 S full-length protein is operably linked to a Pr13.5long promoter for gene expression.

Embodiments Relating to MVA

In one embodiment, the recombinant MVA is generated from an MVA selected from the group consisting of MVA- 572, MVA-575, MVA-I721, NIH clone 1 and MVA-BN, preferably from MVA-BN or a MVA-BN derivative.

MVA-572 has been deposited as ECACC V94012707 on 27 Jan. 1994; MVA-575 has been deposited as ECACC V00120707 on 7 Dec. 2000; MVA-I721 is referenced in Suter et al. Vaccine 2009, 27: 7442-7450; NIH clone 1 has been deposited as ATCC® PTA-5095 on 27 Mar. 2003; and MVA-BN has been deposited at the European Collection of Cell Cultures (ECACC) under number V00083008 on 30 Aug. 2000.

In one embodiment, the recombinant MVA is a recombinant MVA-BN or a recombinant MVA-BN derivative.

Further Embodiments

It is considered that an amino acid sequence defined by any of SEQ ID NO: 1, 3, 5, 7, 9, 11-20, 22, and 24 is identical to the amino acid sequence as depicted in said SEQ ID NO. It is furthermore considered that an amino acid sequence defined by any of SEQ ID NO: 1, 3, 5, 7, 9, 11-20, 22, and 24 shares with the amino acid sequence as depicted in said SEQ ID NO a sequence homology of at least 80%, 85%, 90% 95%, 98%, or 99%.

It is considered that a nucleic acid sequence defined by any of SEQ ID NO: 2, 4, 6, 8, 10, 21, 23, and 25 is identical to the nucleic acid sequence as depicted in said SEQ ID NO. It is furthermore considered that a nucleic acid sequence defined by any of SEQ ID NO: 2, 4, 6, 8, 10, 21, 23, and 25 shares with the nucleic acid sequence as depicted in said SEQ ID NO a sequence homology of at least 80%, 85%, 90%, 98%, or 99%.

In one embodiment, the amino acid sequence of SARS-CoV-2 3aEM fusion protein is a portion of an amino acid sequence comprising the amino acid sequence of SARS-CoV-2 3aEM fusion protein. In cases in which the amino acid sequence of SARS-CoV-2 3aEM fusion protein is preceded N-terminally by another amino acid sequence, the amino acid sequence of SARS-CoV-2 3aEM fusion protein is considered to be as depicted in SEQ ID NO: 19 without the first methionine residue, or as depicted in SEQ ID NO: 20 without the first methionine residue.

In one embodiment, the antigenic part from a SARS-CoV-2 protein is selected from the group of amino acid sequences consisting of SEQ ID NO: 14, 15, 16, 17, and 18.

In one embodiment, the amino acid sequence of an antigenic part from SARS-CoV-2 protein 3a, protein E or protein M is a sub-section of the amino acid sequence as depicted in SEQ ID NO: 14, 15, 16, 17, or 18, respectively.

In one embodiment, the amino acid sequence of an antigenic part from SARS-CoV-2 protein 3a, protein E or protein M comprises an amino acid sequence as depicted in SEQ ID NO: 14, 15, 16, 17, or 18, respectively, or a sub-section thereof.

In one embodiment, the DNA sequence as described herein, preferably for the preparation of a recombinant virus, more preferably for the preparation of a recombinant MVA, is selected from the group consisting of a plasmid, a linear DNA, a PCR product and a synthetic DNA.

In one embodiment, the pharmaceutical composition, or the vaccine, comprising the recombinant MVA further comprises an adjuvant. A recombinant MVA of the invention and/or pharmaceutical composition comprising a recombinant MVA of the invention can be used in a method of treating a subject that has been or may have been exposed to SARS-CoV-2, or be at risk for developing COVID-19, comprising the step of administering the recombinant MVA and/or pharmaceutical composition to said subject. In such embodiments, the step of administering the recombinant MVA and/or pharmaceutical composition results in an immune response in the subject such as, for example, the production of antibodies (e.g., neutralizing antibodies). In this manner, the invention also provides methods of stimulating an immune response in a subject comprising the step of administering a recombinant MVA of the invention or pharmaceutical composition comprising a recombinant MVA of the invention to a subject, whereby an immune response is produced in the subject. An immune response is said to be produced in a subject, for example, if antibodies specific for the recombinant MVA are present in the subject following administration of the recombinant MVA. For example, an immune response is said to be produced in a subject following administration of the recombinant MVA if antibodies are produced in the subject that recognize a SARS-CoV-2 antigen encoded by the recombinant MVA. Measurement of antibodies in a subject can be any of a variety of methods well-known in the art.

In one embodiment, the step of administering the recombinant MVA and/or pharmaceutical composition results in the production of antigen-binding antibodies, the induction of an antigen specific T cell response, preferably a CD8 T cell response, and/or the induction of an antigen specific B cell response. Preferably, the antigen-binding antibodies, the T cell response and/or the B cell response are directed against the SARS-CoV-2 S full-length protein, or a part or an antigenic determinant thereof, more preferably against the RBD, or a part or an antigenic determinant thereof.

In one embodiment, the recombinant MVA for use in the prevention or treatment of a coronavirus disease, preferably COVID-19, is used for the induction of antigen-binding antibodies, an antigen-specific T cell response and/or an antigen-specific B cell response.

In one embodiment, the recombinant MVA for use in the prevention or treatment of a coronavirus disease, preferably COVID-19, which is used for the induction of antigen-binding antibodies, an antigen-specific T cell response and/or an antigen-specific B cell response is a recombinant MVA comprising a nucleic acid sequence encoding an amino acid sequence of a SARS-CoV-2 S full-length protein as described herein. Preferably, the recombinant MVA for use is MVA-mBN500.

In one embodiment, the recombinant MVA for use in the prevention or treatment of a coronavirus disease, preferably COVID-19, is used in combination with a recombinant non-MVA virus. Preferably, the recombinant non-MVA virus encodes SARS-CoV-2 derived antigens. Thus, the invention provides methods of treating a subject or producing an immune response in a subject comprising administering to the subject a recombinant MVA of the invention and said recombinant non-MVA virus. In these embodiments, the recombinant MVA and recombinant non-MVA virus may be administered at the same time or at different times. In embodiments in which the recombinant MVA and recombinant non-MVA virus are administered at different times, they can be administered within 12 weeks of each other, or within 11, 10, 9, 8, 7, 6, 5, 4, 3, 2, or 1 week of each other. The recombinant MVA and recombinant non-MVA virus can be administered via the same route or by different routes of administration. In some embodiments, a subject treated with administration of the recombinant MVA and the recombinant non-MVA virus will produce an immune response to an antigen encoded by each of the recombinant MVA and the recombinant non-MVA virus.

In one embodiment, the recombinant MVA for use in the prevention or treatment of a coronavirus disease, preferably COVID-19, is used in combination with a recombinant adenovirus. Preferably, the recombinant adenovirus encodes one or more SARS-CoV-2 derived antigens. Thus, the invention provides methods of treating a subject or producing an immune response in a subject comprising administering to the subject a recombinant MVA of the invention and said recombinant adenovirus. In these embodiments, the recombinant MVA and recombinant adenovirus may be administered at the same time or at different times. In embodiments in which the recombinant MVA and recombinant adenovirus are administered at different times, they can be administered within 12 weeks of each other, or within 11, 10, 9, 8, 7, 6, 5, 4, 3, 2, or 1 week of each other. The recombinant MVA and recombinant adenovirus can be administered via the same route or by different routes of administration. In some embodiments, a subject treated with administration of the recombinant MVA and the recombinant adenovirus will produce an immune response to an antigen encoded by each of the recombinant MVA and the recombinant non-MVA virus.

In one embodiment, the recombinant MVA for use in the prevention or treatment of a coronavirus disease, preferably COVID-19, is used in a homologous prime-boost vaccination regimen.

In one embodiment, the recombinant MVA for use in the prevention or treatment of a coronavirus disease, preferably COVID-19, which is used in a homologous prime-boost vaccination regimen, is a recombinant MVA comprising a nucleic acid sequence encoding an amino acid sequence of a SARS-CoV-2 S full-length protein as described herein. Preferably, the recombinant MVA for use is MVA-mBN500.

In one embodiment, the recombinant MVA for use in the prevention or treatment of a coronavirus disease, preferably COVID-19, is used in a heterologous prime-boost vaccination regimen. Preferably, a recombinant adenovirus encoding one or more SARS-CoV-2 derived antigens is used in a first (priming) administration, and a recombinant MVA as described herein is used in a subsequent boosting administration.

Certain embodiments also include the following items:

1. A recombinant Modified Vaccinia Virus Ankara (MVA), comprising:
   a nucleic acid sequence encoding an amino acid sequence of a severe acute respiratory syndrome coronavirus 2 (SARS-CoV-2) spike (S) protein or a part thereof, wherein
   (A) the amino acid sequence is an amino acid sequence of a SARS-CoV-2 S full-length protein comprising two consecutive non-native proline residues;
   (B) the part of the amino acid sequence is an amino acid sequence of a part of a SARS-CoV-2 S protein S1 domain, which part comprises a SARS-CoV-2 S receptor binding domain (RBD).
2. The recombinant MVA of item 1, comprising:
   (a) a nucleic acid sequence encoding an amino acid sequence of a part of a SARS-CoV-2 S protein S1 domain, which part comprises a SARS-CoV-2 S RBD; and
   (b) a nucleic acid sequence encoding an amino acid sequence of a fusion protein comprising antigenic parts from two or more SARS-CoV-2 proteins, which parts are not naturally exposed on the surface of SARS-CoV-2 or a virion derived therefrom.
3. The recombinant MVA of item 2, wherein the amino acid sequence under (a) comprises amino acid residues no. 220-650, 270-600, 300-570, 319-549, or 310-530 of the SARS-CoV-2 S full-length protein, preferably comprises amino acid residues no. 319-549.
4. The recombinant MVA of item 2 or 3, wherein the amino acid sequence under (a) comprises a substitution at amino acid residues no. 331 of the SARS-CoV-2 S full-length protein, preferably comprises an (N331A) exchange.
5. The recombinant MVA of item 2, wherein the two or more SARS-CoV-2 proteins under (b) are selected from the group consisting of a protein 3a, a protein E and a protein M.
6. The recombinant MVA of item 2 or 5, wherein the amino acid sequence under (b) comprises two antigenic parts from a SARS-CoV-2 protein 3a, one antigenic part from a SARS-CoV-2 protein E, and two antigenic parts from a SARS-CoV-2 protein M.
7. The recombinant MVA of any one of items 2, 5 and 6, wherein the amino acid sequence under (b) comprises an amino acid sequence consisting of 297 amino acids and comprising substitutions at amino acids no. 131, 132, 179, and 180, preferably comprising (A131W), (Y132F), (S179D), and (Y180F) exchanges.
8. The recombinant MVA of item 1, wherein the amino acid sequence under (A) comprises a further modification capable of preventing proteolytic cleavage of the SARS-CoV-2 full-length protein by furin-like proteases.
9. The recombinant MVA of item 1 or 8, wherein the amino acid sequence under (A) comprises a proline substitution each at amino acid residues no. 986 and no. 987 of the SARS-CoV-2 S full-length protein, preferably comprises an (X986P) and (Y987P) exchange.
10. The recombinant MVA of any one of items 1, 8 and 9, wherein the amino acid sequence under (A) comprises a substitution of consecutive amino acids RRAR resulting in a GSAS amino acid stretch at a furin cleavage site, preferably comprises a GSAS amino acid stretch at amino acid residues no. 682-685 of the SARS-CoV-2 S full-length protein.
11. A DNA sequence, preferably a plasmid, for the preparation of a recombinant MVA of any one of items 1 to 10, comprising:
    (aa) a nucleic acid sequence encoding an amino acid sequence of a part of a SARS-CoV-2 S protein S1 domain, which part comprises a SARS-CoV-2 S RBD; and
    (bb) a nucleic acid sequence encoding an amino acid sequence of a fusion protein comprising antigenic parts from two or more SARS-CoV-2 proteins, which parts are not naturally exposed on the surface of SARS-CoV-2 or a virion derived therefrom; or
    (cc) a nucleic acid sequence encoding an amino acid sequence of a SARS-CoV-2 S full-length protein, wherein the amino acid sequence comprises two consecutive non-native proline residues.
12. A method for the preparation of a recombinant MVA of any one of items 1 to 10, comprising the steps of:
    (1) providing a DNA sequence, preferably a plasmid, of item 11 (aa) and (bb) or item 11 (cc);
    (2) contacting said DNA sequence with an MVA for homologous recombination; and
    (3) obtaining the recombinant MVA.
13. A pharmaceutical composition, or a vaccine, comprising a recombinant MVA of any one of items 1 to 10, further comprising a pharmaceutically acceptable carrier or excipient.

14. Use of a recombinant MVA of any one of items 1 to 10 for the preparation of a pharmaceutical composition, or a vaccine.
15. A recombinant MVA of any one of items 1 to 10 for use as a pharmaceutical, or a vaccine.
16. A recombinant MVA of any one of items 1 to 10 for use in the prevention or treatment of a viral infection, preferably a coronavirus infection, preferably coronavirus disease 19 (COVID-19).

Further Description

Modified Vaccinia Virus Ankara (MVA)

In the past, MVA was generated by 516 serial passages on chicken embryo fibroblasts of the Ankara strain of vaccinia virus (CVA) (for review see Mayr et al. 1975). This virus was renamed from CVA to MVA at passage 570 to account for its substantially altered properties. MVA was subjected to further passages up to a passage number of over 570. As a consequence of these long-term passages, the genome of the resulting MVA virus had about 31 kilobases of its genomic sequence deleted and, therefore, was described as highly host cell restricted for replication to avian cells (Meyer et al. 1991). It was shown in a variety of animal models that the resulting MVA was significantly avirulent compared to the fully replication competent starting material (Mayr and Danner 1978).

An MVA useful in the practice of the present invention includes MVA-572 (deposited as ECACC V94012707 on 27 Jan. 1994); MVA-575 (deposited as ECACC V00120707 on 7 Dec. 2000), MVA-I721 (referenced in Suter et al. 2009), NIH clone 1 (deposited as ATCC® PTA-5095 on 27 Mar. 2003) and MVA-BN (deposited at the European Collection of Cell Cultures (ECACC) under number V00083008 on 30 Aug. 2000).

More preferably the MVA used in accordance with the present invention includes MVA-BN and MVA-BN derivatives. MVA-BN has been described in WO 02/042480. "MVA-BN derivatives" refer to any virus exhibiting essentially the same replication characteristics as MVA-BN, as described herein, but exhibiting differences in one or more parts of their genomes.

MVA-BN, as well as MVA-BN derivatives, is replication incompetent, meaning a failure to reproductively replicate in vivo and in vitro. More specifically in vitro, MVA-BN or MVA-BN derivatives have been described as being capable of reproductive replication in chicken embryo fibroblasts (CEF), but not capable of reproductive replication in the human keratinocyte cell line HaCat (Boukamp et al 1988), the human bone osteosarcoma cell line 143B (ECACC Deposit No. 91112502), the human embryo kidney cell line 293 (ECACC Deposit No. 85120602), and the human cervix adenocarcinoma cell line HeLa (ATCC Deposit No. CCL-2). Additionally, MVA-BN or MVA-BN derivatives have a virus amplification ratio at least two-fold less, more preferably three-fold less than MVA-575 in Hela cells and HaCaT cell lines. Tests and assay for these properties of MVA-BN and MVA-BN derivatives are described in WO 02/42480 and WO 03/048184.

The term "not capable of reproductive replication" in human cell lines in vitro as described above is, for example, described in WO 02/42480, which also teaches how to obtain MVA having the desired properties as mentioned above. The term applies to a virus that has a virus amplification ratio in vitro at 4 days after infection of less than 1 using the assays described in WO 02/42480 or U.S. Pat. No. 6,761,893.

Exemplary Generation of a Recombinant MVA Virus

For the generation of a recombinant MVA as disclosed herein, different methods may be applicable. The DNA sequence to be inserted into the virus can be placed into an *E. coli* plasmid construct into which DNA homologous to a section of DNA of the poxvirus has been inserted. Separately, the DNA sequence to be inserted can be ligated to a promoter. The promoter-gene linkage can be positioned in the plasmid construct so that the promoter-gene linkage is flanked on both ends by DNA homologous to a DNA sequence flanking a region of poxvirus DNA containing a non-essential locus. The resulting plasmid construct can be amplified by propagation within *E. coli* bacteria and isolated. The isolated plasmid containing the DNA gene sequence to be inserted can be transfected into a cell culture, e.g., of chicken embryo fibroblasts (CEFs), at the same time the culture is infected with MVA. Recombination between homologous MVA viral DNA in the plasmid and the viral genome, respectively, can generate an MVA modified by the presence of foreign DNA sequences, i.e. nucleotides sequences encoding SARS-CoV-2 antigens.

According to a preferred embodiment, a cell of a suitable cell culture as, e.g., CEF cells, can be infected with a MVA virus. The infected cell can be, subsequently, transfected with a first plasmid vector comprising a foreign or heterologous gene or genes, such as one or more of the nucleic acids provided herein, preferably under the transcriptional control of a poxvirus expression control element. As explained above, the plasmid vector also comprises sequences capable of directing the insertion of the exogenous sequence into a selected part of the MVA viral genome. Optionally, the plasmid vector also contains a cassette comprising a marker and/or selection gene operably linked to a poxvirus promoter. The use of selection or marker cassettes simplifies the identification and isolation of the generated recombinant MVA. However, a recombinant poxvirus can also be identified by PCR technology. Subsequently, a further cell can be infected with the recombinant MVA obtained as described above and transfected with a second vector comprising a second foreign or heterologous gene or genes. In case, this gene shall be introduced into a different insertion site of the poxvirus genome, the second vector also differs in the poxvirus-homologous sequences directing the integration of the second foreign gene or genes into the genome of the poxvirus. After homologous recombination has occurred, the recombinant virus comprising two or more foreign or heterologous genes can be isolated. For introducing additional foreign genes into the recombinant virus, the steps of infection and transfection can be repeated by using the recombinant virus isolated in previous steps for infection and by using a further vector comprising a further foreign gene or genes for transfection. There are ample of other techniques known to generate recombinant MVA.

The practice of the invention will employ, if not otherwise specified, conventional techniques of immunology, molecular biology, microbiology, cell biology, and recombinant technology, which are all within the skill of the art. See e.g. Sambrook, Fritsch and Maniatis, Molecular Cloning: A Laboratory Manual, 2nd edition, 1989; Current Protocols in Molecular Biology, Ausubel F M, et al., eds, 1987; the series Methods in Enzymology (Academic Press, Inc.); PCR2: A Practical Approach, MacPherson M J, Hams B D, Taylor G R, eds, 1995; Antibodies: A Laboratory Manual, Harlow and Lane, eds, 1988.

EXAMPLES

The following examples serve to further illustrate the disclosure. They should not be understood as limiting the invention the scope of which is determined by the appended claims.

Example 1: Designing SARS-CoV-2 Antigens

The reference strain for all sequences is SARS-CoV-2 isolate Wuhan-Hu-1 (NC_045512.2).

1.1 SARS-CoV-2 S1 Fragment Containing RBD

The original SARS-CoV-2 S protein sequence (YP_009724390.1; see SEQ ID NO: 1) containing the RBD (amino acids 331-524) served as a basis.

The amino acid sequence to be expressed contains the RBD amino acid sequence and additional amino acids of the S1 domain (located N- and C-terminally from the RBD), thereby spanning amino acids 319-549 of the original SARS-CoV-2 S1 domain (see FIG. 1). This sequence is modified at amino acid 331 in that the asparagine residue is replaced by an alanine residue (N331A) in order to avoid glycosylation. A secretion tag (signal peptide) from human IgG heavy chain "hIgGH") was added N-terminally to allow efficient secretion of the RDB and the S1 domain fragment, respectively. For the final amino acid sequence, see SEQ ID NO: 9 ("SARS-2 S-RBD-1").

1.2 SARS-CoV-2 3aEM Fusion Protein

Antigenic fragments were derived from SARS-CoV-2 proteins for the generation of a fusion protein serving as antigen to induce strong and/or broad T cell response. The fusion protein is intended for (but not restricted to) cytoplasmic localization. Surface predicted amino acids of structural SARS-CoV-2 proteins were removed, and areas of clustered validated or predicted T cell antigenic peptides were chosen. The SARS-CoV-2 proteins used for deriving the antigenic fragments were structural proteins unrelated to the SARS-CoV-2 S protein: Protein 3a (YP_009724391.1), protein E (YP_009724392.1) and protein M (YP_009724393.1).

The two 3a protein fragments (3a-1, 3a-2) used in the fusion protein correspond to amino acids 56-83 and amino acids 178-275 of the full-length 3a protein, respectively. The protein E fragment used in the fusion protein corresponds to amino acids 38-73 of the full-length E protein. The two protein M fragments (M-1, M-2) used in the fusion protein correspond to amino acids 37-51 and amino acids 94-212, respectively.

The amino acid sequences of the fragments used for a fusion protein construction are shown in FIG. 2 and SEQ ID NO: 14 to 18. The resulting fusion protein is shown in SEQ ID NO: 19

To avoid newly created epitopes at junctions between fragments, the fusion protein was modified: a mutation each of two amino acids at junction 3a-2 fragment/E fragment (A131W, Y132F) and junction M-1 fragment/M-2 fragment (S179D, Y180F) was introduced (see FIG. 3). For the final SARS CoV-2 3aEM fusion protein sequence, see SEQ ID NO: 20 ("SARS-2 3aEM-1").

1.3 SARS-CoV-2 S Full-Length Protein

The original SARS-CoV-2 S full-length protein sequence (YP_009724390.1; see SEQ ID NO: 1) was modified by substitutions at amino acids 986 and 987, i.e. amino acid exchanges by prolines (K986P, V987P), to stabilize the expressed protein in a prefusion state. The sequence was further modified by substitution of consecutive amino acids RRAR at the furin cleavage site (amino acids 682-685), resulting in a GSAS amino acid stretch (see FIG. 4). For the final amino acid sequence, see SEQ ID NO: 24 ("SARS-2 FS-1").

Example 2: Constructs Encoding SARS-CoV-2 Antigens 2.1 MVA-mBN499

The MVA-mBN499 construct contains (1) a nucleotide sequence encoding SARS-2-CoV-2 S RBD in the form of a secreted version of a SARS-CoV-2 S1 fragment (see Example 1.1), and (2) a nucleotide sequence encoding the SARS-CoV-2 3aEM fusion protein (see Example 1.2).

Figure 5:
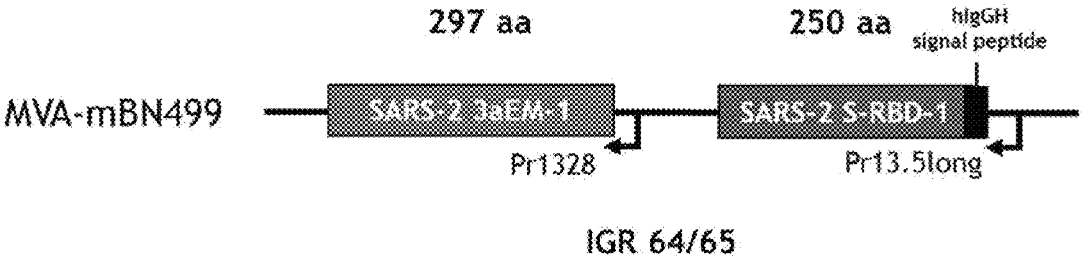
FIG. 5 shows expression cassettes for expressing the part of SARS-CoV-2 S1 domain ("SARS-2 S RBD-1") and SARS-CoV-2 3aEM fusion protein ("SARS-2 3aEM-1"), which is inserted into the MVA genome to result in recombinant MVA-mBN499.

Expression of SARS-CoV-2 S RBD is driven by the Pr13.5long promoter (Wennier et al., 2013; WO 2014/063832; see SEQ ID NO: 26), expression of SARS-CoV-2 3aEM fusion protein by the Pr1328 promoter (see SEQ ID NO: 27). For the expression cassettes and their position in MVA-BN, see FIG. 5.

On this basis, a plasmid for homologous recombination with MVA-BN was prepared. The insertion site of the two expression cassettes in MVA-BN is IGR 64/65.

2.2 MVA-mBN500

The MVA-mBN500 construct contains a nucleotide sequence encoding a modified SARS-CoV-2 S full-length protein (see Example 1.3), i.e. a prefusion stabilized SARS-CoV-2 S full-length protein with two consecutive non-native prolines and a mutated polybasic cleavage site.

Figure 6:
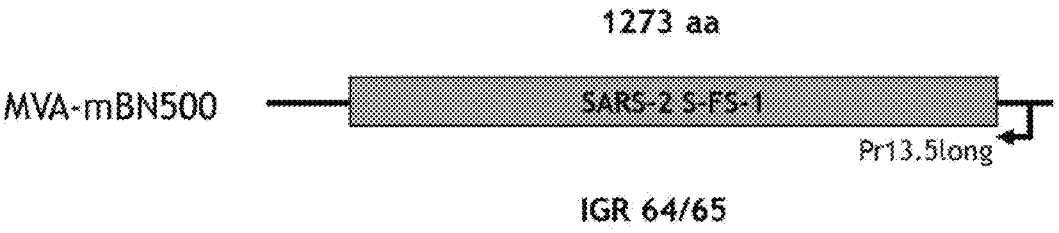
FIG. 6 shows an expression cassette for expressing stabilized SARS-CoV-2 S full-length protein ("SARS-2 S-FS-1), which is inserted into the MVA genome to result in recombinant MVA-mBN500.

Expression of the stabilized SARS-CoV-2 S full-length protein is also driven by the Pr13.5long promoter (see above). For the expression cassette and its position in MVA-BN, see FIG. 6.

A plasmid for homologous recombination with MVA-BN was prepared. The insertion site of the expression cassettes in MVA-BN is IGR 64/65.

Example 3: Recombinant MVA Encoding SARS-CoV-2 Antigens

The generation of recombinant MVA was accomplished by homologous recombination using the constructs described in Example 2.1 and 2.2. The procedure was basically as described (Staib et al., 2004).

Efficient SARS-CoV-2 antigen expression by MVA-mBN499 and MVA-mBN500 was verified using RT-PCR, flow cytometry and immune blot techniques (see below).

Example 4: Expression of SARS-CoV-2 Antigens 4.1 MVA-mBN499

MVA-mBN499-driven expression of the RBD of the SARS-CoV-2 spike protein was demonstrated by immunoblot analysis of lysates of infected HeLa cells.

HeLa cells in DMEM/10% FCS were seeded in 6-well plates at the day of infection at $1\times10^6$ cells/well. Cells were mock infected or infected at 37° C. with MVA-BN or MVA-mBN499 at 10 $TCID_{50}$ per cell approximately 8 hours after seeding. At 16 hours post infection, cells were harvested by scraping into lysis buffer, and lysates were diluted with PBS and 2× Laemmli sample buffer. Supernatants of cells were collected, and an aliquot was concentrated approximately 12-fold using Amicon Ultra-0.5 filter column devices and plain supernatant from cells as well as concentrated supernatants were mixed with the appropriate amounts of Laemmli buffer. Proteins in cell lysates and supernatants were separated according to size on 10% Mini-Protean TGX gels and analyzed by immunoblotting using anti-vaccinia virus rabbit polyclonal serum (Quartett, Berlin, Germany) (FIG. 7A) and an anti-RBD monoclonal rabbit antibody (Sino Biological, cat no. 40592-T62) (FIG. 7B), followed by the appropriate secondary antibody. Immunoblot images were acquired using the ChemiDoc Touch System and Image Lab Software.

Figure 7:
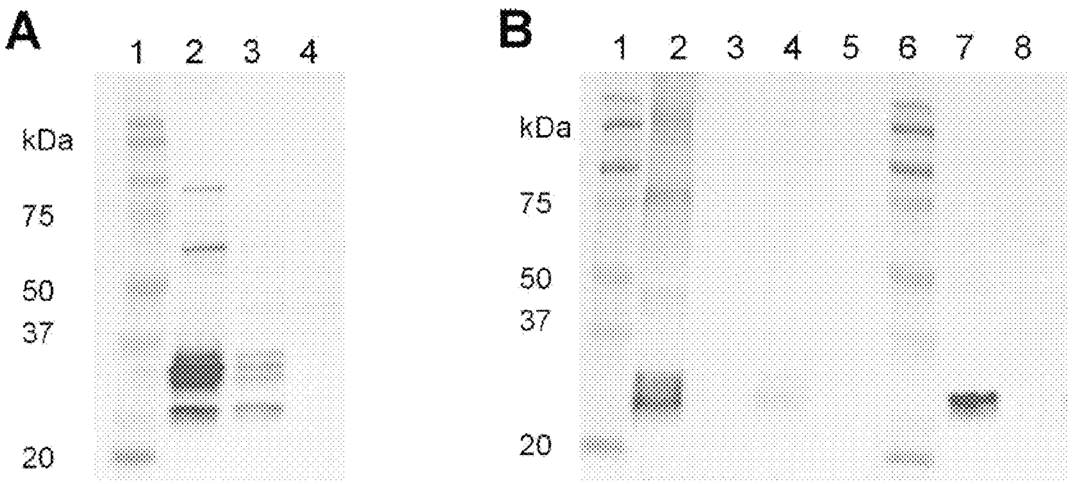
FIG. 7 shows the expression of SARS-CoV-2 S1 fragment containing RBD ("SARS-2 S-RBD-1") by MVA-mBN499. HeLa cells were mock infected or infected with MVA-BN or MVA-mBN499. Proteins in cell lysates and supernatants were separated according to size on 10% Mini-Protean TGX gels and analyzed by immunoblotting using anti-vaccinia virus rabbit polyclonal serum (A) and an anti-RBD monoclonal rabbit antibody (B), followed by the appropriate secondary antibody. (A) 1=molecular weight marker (in kDa), 2=lysate MVA-mBN499 infected cells, 3=lysate MVA-BN infected cells, 4=mock infected cells. (B) 1=molecular weight marker (in kDa), 2=concentrated supernatant (sup) MVA-mBN499, 3=concentrated sup MVA-BN, 4=plain sup MVA-mBN499, 5=plain sup MVA-BN, 6=molecular weight marker (in kDa), 7=lysate MVA-mBN499 infected cells, 8=lysate MVA-BN infected cells.

Both lysates of cells infected with MVA-mBN499 and the parental, non-recombinant MVA-BN showed a similar pattern of vaccinia virus-specific proteins when the blot was developed with an anti-vaccinia virus antiserum while no proteins were detected in the mock infected controls (FIG. 7A). Upon detection of a parallel immunoblot with a SARS-CoV-2 S-RBD-specific antibody, a protein migrating at the expected position for a protein of a molecular weight of 28 kDa was detected, while no such protein was detectable in control cells infected with parental MVA-BN (FIG. 7B). Thus, the SARS-CoV-2 RBD was expressed by MVA-mBN499.

The RBD protein expressed by MVA-mBN499 was also detectable in supernatants of MVA-mBN499 infected cells (FIG. 7B). Upon concentration of the cell supernatants of MVA-mBN499 infected cells, a stronger RBD-specific signal was obtained and proteins migrating at about 46 and 90 kDa possibly representing oligomeric forms of RBD were detectable (FIG. 7B). No such signals were obtained in concentrated supernatant of MVA-BN infected cells (FIG. 7B). In conclusion, RBD was expressed in mBN499 infected cells and secreted into the cellular supernatants.

4.2 MVA-mBN500

Expression of the SARS-CoV-2 S full-length protein was proven by flow cytometry analysis of MVA-mBN500 infected HeLa cells and the respective controls using a full-length spike protein-specific antibody.

HeLa cells were seeded in 6-well plates at $5\times10^5$ cells/well in 1 ml of DMEM/10% FCS on the day before infection. Cells were mock infected or infected at 37° C. with MVA-BN or MVA-mBN500 at 4 $TCID_{50}$ per cell in triplicates on day zero. 18 hours post infection, cells were scraped, washed, and fixed with 4% formaldehyde before surface-staining with an anti-vaccinia virus rabbit polyclonal serum (Quartett, Berlin, Germany) (FIG. 8A, and left panel of FIG. 8B) and a mouse monoclonal antibody directed against full-length SARS-CoV-2 spike protein (GeneTex GTX632604/Biozol, Eching, Germany) (FIG. 8A, and right panel of FIG. 8B), followed by the appropriate secondary antibodies.

Figure 8:
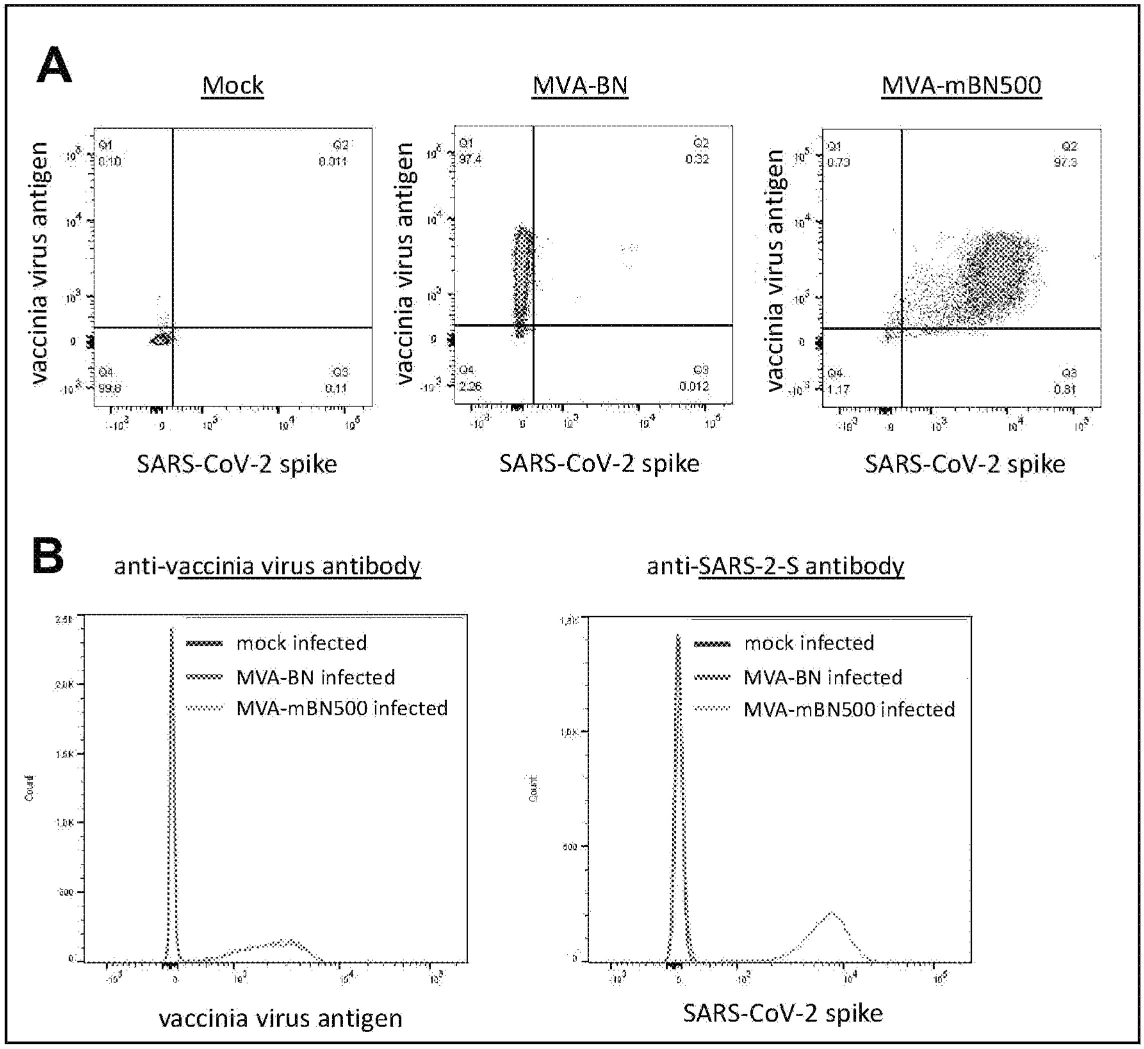
FIG. 8 shows the expression of prefusion stabilized SARS-CoV-2 S full-length protein ("SARS-2 FS-1") by MVA-mBN500. HeLa cells were surface-stained with an anti-vaccinia virus rabbit polyclonal serum (A, and left panel of B) and a mouse monoclonal antibody directed against full-length SARS-CoV-2 spike protein (A, and right panel of B) followed by the appropriate secondary antibodies. Stained cells were analyzed by flow cytometry and representative results for a single cell sample out of three are each shown as dot plots (A) and histogram plots (B).

Cells infected with MVA-mBN500 showed a large cell population (>97%) that was double-positive for vaccinia antigen and SARS-CoV-2 spike indicating expression the SARS-CoV-2 spike protein in the vast majority of infected cells (FIG. 8A, right panel). Infection with MVA-mBN500 was similarly efficient as with the control MVA-BN virus (FIG. 8B, left panel). MVA-mBN500 infected cells were homogeneously expressing the SARS-CoV-2 spike protein as indicated by the single clear peak of spike protein-specific surface staining, and expression levels of the spike protein were high (FIG. 8B, right panel).

Example 5: Immunogenicity of SARS-CoV-2 Antigens In Vivo 5.1 Induction of Antigen-Specific T Cell Responses It was determined whether homologous prime-boost vaccination by intramuscular administration of MVA-mBN499 or MVA-mBN500 would enhance T cell responses against SARS-Co-V-2 expressed proteins and antigens.

Balb/c mice were immunized intramuscularly on days 0 ("prime") and 21 ("boost") with either $1\times10^8$ $TCID_{50}$ of MVA-mBN499 or MVA-mBN500. Mice were sacrificed at day 34 after prime immunization. At the day of sacrifice, both IFN-γ ELISPOT and Intracellular Cytokine Staining (ICCS) by flow cytometry was performed.

The following peptide pools from GenScript were tested:

1. "SARS-CoV-2 Spike Pool A": Peptide pool containing the RBD region;
2. "SARS-CoV-2 Spike Pool B": Peptide pool containing the rest of the spike peptides, but not the RBD.
3. "SARS-CoV-2 3aEM Peptide Pool 37-49": Peptide pool generated from the string of antigens encoded in MVA mBN499 (only assayed in Elispot).

Figure 9:
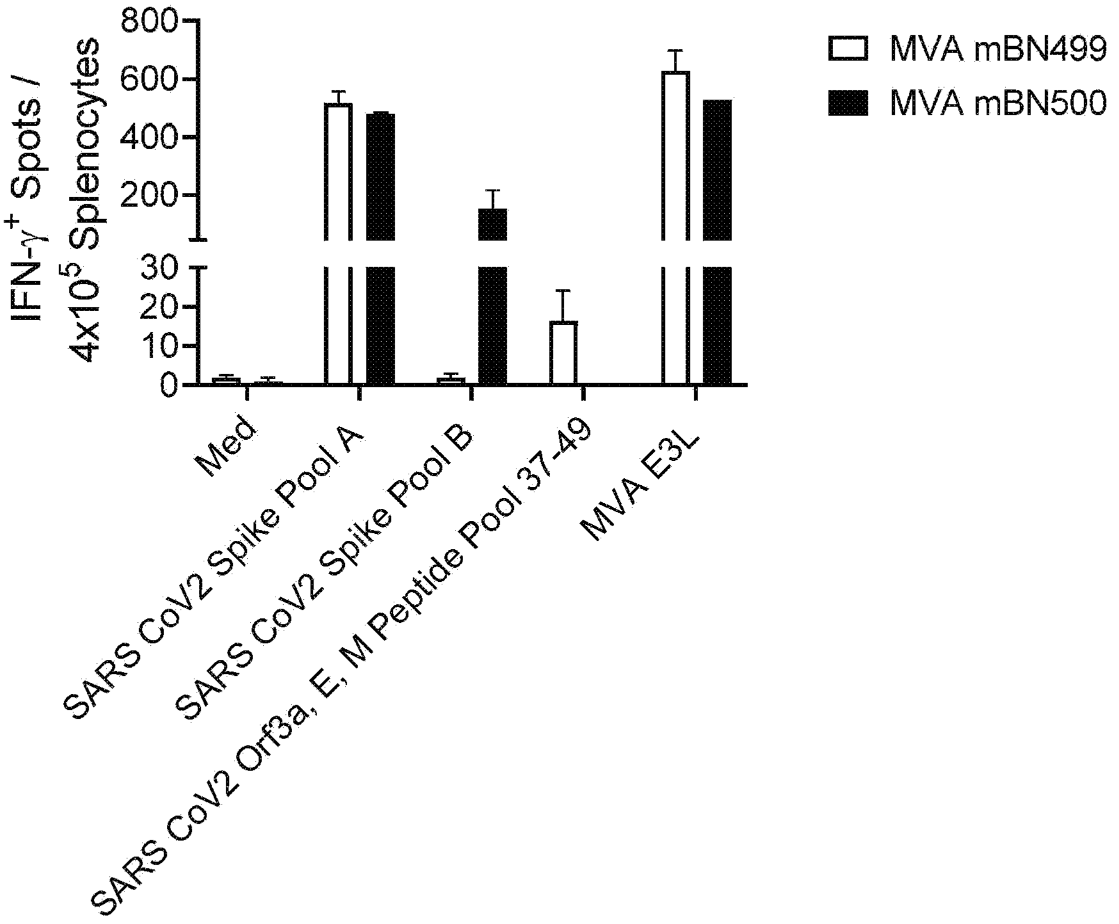
FIG. 9 shows the induction of antigen specific T cells against SARS-CoV-2 encoded regions by MVA-mBN499 and MVA-mBN500. On days 0 and 21, Balb/c mice (n=3/group) were vaccinated intramuscularly with either $1\times10^8$ $TCID_{50}$ of MVA-mBN499 or MVA-mBN500. Mice were sacrificed on day 34 after prime immunization. IFN-γ ELISPOT in which $4\times10^5$ splenocytes were incubated with SARS-CoV-2 derived peptide pools as indicated. MVA E3L dominant $CD8^+$ T cell epitope was used as positive control. Data are expressed as Mean±SEM.

ELISPOT analysis of MVA-mBN499 or MVA-mBN500 immunized mice showed a similar induction of IFN-γ expressing T cells against the spike RBD domain expressed in the spike pool A (FIG. 9A). Only IFN-γ spots were detected in the spike pool B when MVA-mBN500 splenocytes were assayed, consistent with construct design (FIG. 9A). Similarly, a low but detectable number of spots were detected in MVA-mBN499 splenocytes incubated with a peptide pool spanned from the sequences of 3a, E and M protein fragments (FIG. 9A). Altogether, all the vaccine components expressed in both MVA-mBN499 and MVA-mBN500 elicited antigen-specific T cell responses.

Further analysis by flow cytometry showed that these responses were mainly CD8 T cell driven (FIG. 10A). $IFN_\gamma^+$ $TNF\alpha^+$ $CD8^+$ T cells were found, indicating that MVA-mBN499 and MVA-mBN500 generated multi-cytokine producing memory $CD8^+$ T cells against the RBD. Regarding $CD4^+$ T cells, very few but detectable antigen specific $IFN_\gamma^+$ responses were detected (FIG. 10B).

5.2 Induction of Antigen-Binding Antibodies

The presence of SARS-CoV-2 RBD binding antibodies in vaccinated littermates was also analyzed. To this end, the surrogate virus neutralization test developed by GensScript was used following the manufacturer's instructions (cPass™ SARS-CoV-2 Neutralization Antibody Detection Kit, GenScript; Tan et al., 2020).

As described above (see Example 5.1), Balb/c mice were immunized intramuscularly on days 0 ("prime") and 21 ("boost") with either $1\times10^8$ $TCID_{50}$ of MVA-mBN499 or MVA-mBN500. Mice were bled at days 20 and 34 after prime immunization to collect sera for antibody analysis.

As demonstrated in FIG. 11A, a prime immunization with MVA-mBN500 resulted in induction of antibodies that bind to RBD. This effect got diluted (FIG. 11A). In contrast, MVA-mBN499 did not induce any RBD binding antibodies. Upon boost, MVA-mBN500 induced strong RBD binding antibodies that retained their binding capacity upon serial dilutions (FIG. 11B). Again, MVA-mBN499 boost did not result in any RBD binding antibodies.

5.3 Induction of Antigen-Specific B Cell Responses

It was further analyzed whether MVA-mBN500 could induce antigen-specific B cell responses in the draining lymph nodes.

Figure 12:
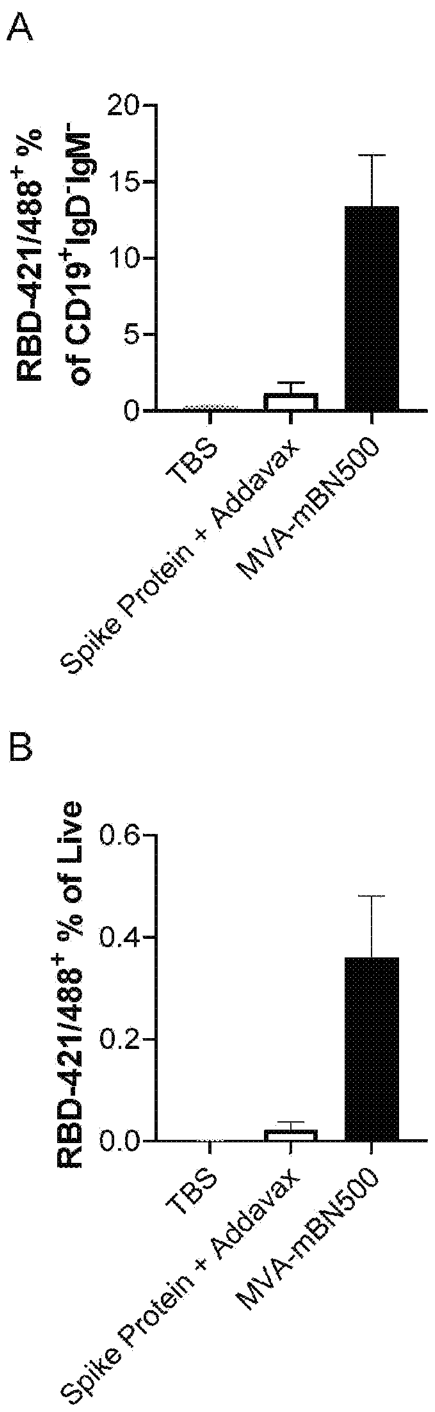
FIG. 12 shows that MVA-mBN500 induces RBD-specific B cells in the draining inguinal lymph nodes. Balb/c mice (n=4/group) were immunized intramuscularly with $5\times10^7$ $TCID_{50}$ MVA-mBN500 or 2.5 μg Spike Protein+AddaVax™ per leg. Inguinal lymph nodes were harvested 11 days after vaccination and lymphocytes were isolated. Lymphocytes were stained with AF488 and BV421 labelled RBD-tetramers to stain for RBD-specific B cells. (A) Frequency of RBD-421/488 specific B cells among CD19+IgM-IgD-cells. (B) Frequency of RBD-421/488 specific B cells among all live lymphocytes in the inguinal lymph nodes. Data are expressed as Mean±SEM.

Balb/c mice were immunized intramuscularly in both legs with $5\times10^7$ $TCID_{50}$ MVA-mBN500 or 2.5 μg spike protein adjuvanted with AddaVax™. Mice were sacrificed after 11 days and the draining inguinal lymph nodes were harvested for analysis of B cells. As a result, RBD-tetramer positive B cells were detected in the lymph nodes of mice immunized with MVA-mBN500 or spike protein compared to PBS control mice (FIG. 12). Notably, however, the amount of RBD-specific B cells was superior in MVA-mBN500 immunized mice (FIG. 12).

5.4 Prime and Prime-Boost Regimens

Prime and homologous prime-boost immunization with MVA-mBN500 was compared.

Balb/c mice received intramuscularly on days 0 ("prime") and 21 ("boost") $1\times10^8$ $TCID_{50}$ of MVA-mBN500. Mice were bled on days 20 and 34 after prime immunization to collect sera for antibody analysis. Mice were sacrificed on day 34 after prime immunization. At the day of sacrifice, both IFN-γ ELISPOT and Intracellular Cytokine Staining (ICCS) by flow cytometry was performed to determine whether prime or homologous prime-boost vaccination by intramuscular administration of MVA-mBN500 would enhance T cell responses against SARS-CoV-2 peptide pools. Prime immunization using MVA-mBN500 induced IFN-$\gamma^+$ spots for SARS-CoV-2 spike pool A containing the RBD sequence, as well as for the other SARS-CoV-2 spike components included in spike pool B (FIG. 13). Homologous prime-boost immunization with MVA-mBN500 increased the number of IFN-$\gamma^+$ spots compared to prime immunization only (FIG. 13). Consistently, we identified superior cytokine production by $CD8^+$ T cells when mice received MVA-mBN500 as a prime-boost regimen compared to prime immunization only (FIG. 14).

Finally, the levels of RBD-binding antibodies were analyzed by serial dilution of sera obtained on day 34 (first final day) using the surrogate virus neutralization test (see Example 5.2). 1:10 dilution steps (from 1:10 to 1:10 000 000) were performed. These dilution steps allowed for calculating the half maximal inhibitory concentration ($IC_{50}$). $IC_{50}$ measures the potency of vaccine induced antibodies in inhibiting antigen binding by 50%. As a result, highest concentrations of RBD-binding antibodies were detected in mice which received MVA-mBN500 as homologous prime-boost as compared to only MVA-mBN500 prime (FIG. 15).

Final remark: Several documents are cited throughout the text of this specification. Each of the documents cited herein (including all patents, patent applications, scientific publications, manufacturer's specifications, instructions, etc.) are hereby incorporated by reference in their entirety. To the extent, the material incorporated by reference contradicts or is inconsistent with this specification, the specification will supersede any such material. Nothing herein is to be construed as an admission that the invention is not entitled to antedate such disclosure by virtue of prior invention.

REFERENCES

Agrawal A S, Tao X, Algaissi A, et al. (2016) Immunization with inactivated Middle East Respiratory Syndrome coronavirus vaccine leads to lung immunopathology on challenge with live virus. Hum Vaccin Immunother 12(9): 2351-2356.

Boukamp P, Petrussevska R T, Breitkreutz D, et al. (1988) Normal Keratinization in a Spontaneously Immortalized Aneuploid Human Keratinocyte Cell Line. J Cell Biol 106(3): 761-771.

Chen W-H, Du L, Chag S M, et al. (2014) Yeast-expressed recombinant protein of the receptor-binding domain in SARS-CoV spike protein with deglycosylated forms as a SARS vaccine candidate. Hum Vaccin Immunother 10(3): 648-658.

Deming D, Sheahan T, Heise M, et al. (2006) Vaccine Efficacy in Senescent Mice Challenged with Recombinant SARS-CoV Bearing Epidemic and Zoonotic Spike Variants. PLoS Med 3(12): e525.

He Y, Li J, Heck S, et al. (2006) Antigenic and Immunogenic Characterization of Recombinant Baculovirus-Expressed Severe Acute Respiratory Syndrome Coronavirus Spike Protein: Implication for Vaccine Design. J Virol 80(12): 5757-5767.

Le T T, Andreadakis Z, Kumar A, et al. (2020) The COVID-19 vaccine development landscape. Nat Rev Drug Disc (19): 305-306.

Lechien J R, Chiesa-Estomba C M, De Siati, D R, et al. (2020) Olfactory and Gustatory Dysfunctions as a Clinical Presentation of Mild-To-Moderate Forms of the Coronavirus Disease (COVID-19): A Multicenter European Study. Eur Arch Otorhinolaryngol (6): 1-11.

Liu L, Wei Q, Lin Q, et al. (2019) Anti-spike IgG causes severe acute lung injury by skewing macrophage responses during acute SARS-CoV infection. JCI Insight 4(4): e123158.

Mayr A and Danner K (1978) Vaccination against pox diseases under immunosuppressive conditions. Dev Biol Stand 41: 225-234.

Mayr A, Hochstein-Mintzel V and Stickl H (1975). Abstammung, Eigenschaften and Verwendung des attenuierten Vaccinia-Stammes MVA. Infektion 3: 6-14.

Meyer H, Sutter G and Mayr A (1991). Mapping of deletions in the genome of the highly attenuated vaccinia virus MVA and their influence on virulence. J Gen Virol 72 (Pt 5): 1031-1038.

Suter M, Meisinger-Henschel C, Tzatzaris M, et al. (2009). Modified vaccinia Ankara strains with identical coding sequences actually represent complex mixtures of viruses that determine the biological properties of each strain. Vaccine 27: 7442-7450.

Staib C, Drexler I and Sutter G (2004) Construction and isolation of recombinant MVA. Methods Mol Biol 269: 77-100.

Tan, C W, Chia, W N, Qin, X et al. (2020) A SARS-CoV-2 surrogate virus neutralization test based on antibody-mediated blockage of ACE2—spike protein—protein interaction. Nat Biotechnol 38: 1073-1078.

Wennier S T, Brinkmann K, Steinhausser C, et al. (2013) A novel naturally occurring tandem promoter in modified vaccinia virus ankara drives very early gene expression and potent immune responses. PLoS One 8(8): e73511.

Wrapp D, Wang N, Corbett K S, et al. (2020) Cryo-EM Structure of the 2019-nCoV Spike in the Prefusion Conformation. Science 367: 1260-1263

Yasui F, Kai C, Kitabatake M, et al. (2008) Prior Immunization with Severe Acute Respiratory Syndrome (SARS)-Associated Coronavirus (SARS-CoV) Nucleocapsid Protein Causes Severe Pneumonia in Mice Infected with SARS-CoV. J Immunol 181: 6337-6348.

Zhou P, Yang X-L, Wang X-G, et al. (2020) Discovery of a novel coronavirus associated with the recent pneumonia outbreak in humans and its potential bat origin. Nature doi: 10.1038/s41586-020-2012-7.

| Sequences |
|---|
| SEQ ID NO: 1 Amino acid sequence of SARS-CoV-2 S full-length protein (YP_009724390.1)<br>MFVFLVLLPLVSSQCVNLTTRTQLPPAYTNSFTRGVYYPDKVFRSSVLHSTQDLFLPFFSNVTWFHAI<br>HVSGTNGTKRFDNPVLPFNDGVYFASTEKSNIIRGWIFGTTLDSKTQSLLIVNNATNVVIKVCEFQFC<br>NDPFLGVYYHKNNKSWMESEFRVYSSANNCTFEYVSQPFLMDLEGKQGNFKNLREFVFKNIDGYFKIY<br>SKHTPINLVRDLPQGFSALEPLVDLPIGINITRFQTLLALHRSYLTPGDSSSGWTAGAAAYYVGYLQP<br>RTFLLKYNENGTITDAVDCALDPLSETKCTLKSFTVEKGIYQTSNFRVQPTESIVRFPNITNLCPFGE<br>VFNATRFASVYAWNRKRISNCVADYSVLYNSASFSTFKCYGVSPTKLNDLCFTNVYADSFVIRGDEVR<br>QIAPGQTGKIADYNYKLPDDFTGCVIAWNSNNLDSKVGGNYNYLYRLFRKSNLKPFERDISTEIYQAG<br>STPCNGVEGFNCYFPLQSYGFQPTNGVGYQPYRVVVLSFELLHAPATVCGPKKSTNLVKNKCVNFNFN<br>GLTGTGVLTESNKKFLPFQQFGRDIADTTDAVRDPQTLEILDITPCSFGGVSVITPGTNTSNQVAVLY<br>QDVNCTEVPVAIHADQLTPTWRVYSTGSNVFQTRAGCLIGAEHVNNSYECDIPIGAGICASYQTQTNS<br>PRRARSVASQSIIAYTMSLGAENSVAYSNNSIAIPTNFTISVTTEILPVSMTKTSVDCTMYICGDSTE<br>CSNLLLQYGSFCTQLNRALTGIAVEQDKNTQEVFAQVKQIYKTPPIKDFGGFNFSQILPDPSKPSKRS<br>FIEDLLFNKVTLADAGFIKQYGDCLGDIAARDLICAQKFNGLTVLPPLLTDEMIAQYTSALLAGTITS<br>GWTFGAGAALQIPFAMQMAYRFNGIGVTQNVLYENQKLIANQFNSAIGKIQDSLSSTASALGKLQDVV<br>NQNAQALNTLVKQLSSNFGAISSVLNDILSRLDKVEAEVQIDRLITGRLQSLQTYVTQQLIRAAEIRA<br>SANLAATKMSECVLGQSKRVDFCGKGYHLMSFPQSAPHGVVFLHVTYVPAQEKNFTTAPAICHDGKAH<br>FPREGVFVSNGTHWFVTQRNFYEPQIITTDNTFVSGNCDVVIGIVNNTVYDPLQPELDSFKEELDKYF<br>KNHTSPDVDLGDISGINASVVNIQKEIDRLNEVAKNLNESLIDLQELGKYEQYIKWPWYIWLGFIAGL<br>IAIVMVTIMLCCMTSCCSCLKGCCSCGSCCKFDEDDSEPVLKGVKLHYT |
| SEQ ID NO: 2 Nucleotide sequence for SEQ ID NO: 1 (plus stop codon in bold)<br>ATGTTTGTTTTTCTTGTTTTATTGCCACTAGTCTCTAGTCAGTGTGTTAATCTTACAACCAGAACTCA<br>ATTACCCCCTGCATACACTAATTCTTTCACACGTGGTGTTTATTACCCTGACAAAGTTTTCAGATCCT<br>CAGTTTTACATTCAACTCAGGACTTGTTCTTACCTTTCTTTTCCAATGTTACTTGGTTCCATGCTATA<br>CATGTCTCTGGGACCAATGGTACTAAGAGGTTTGATAACCCTGTCCTACCATTTAATGATGGTGTTTA<br>TTTTGCTTCCACTGAGAAGTCTAACATAATAAGAGGCTGGATTTTTGGTACTACTTTAGATTCGAAGA<br>CCCAGTCCCTACTTATTGTTAATAACGCTACTAATGTTGTTATTAAAGTCTGTGAATTTCAATTTTGT<br>AATGATCCATTTTTGGGTGTTTATTACCACAAAAACAACAAAAGTTGGATGGAAAGTGAGTTCAGAGT<br>TTATTCTAGTGCGAATAATTGCACTTTTGAATATGTCTCTCAGCCTTTTCTTATGGACCTTGAAGGAA<br>AACAGGGTAATTTCAAAAATCTTAGGGAATTTGTGTTTAAGAATATTGATGGTTATTTTAAAATATAT<br>TCTAAGCACACGCCTATTAATTTAGTGCGTGATCTCCCTCAGGGTTTTTCGGCTTTAGAACCATTGGT<br>AGATTTGCCAATAGGTATTAACATCACTAGGTTTCAAACTTTACTTGCTTTACATAGAAGTTATTTGA<br>CTCCTGGTGATTCTTCTTCAGGTTGGACAGCTGGTGCTGCAGCTTATTATGTGGGTTATCTTCAACCT<br>AGGACTTTTCTATTAAAATATAATGAAAATGGAACCATTACAGATGCTGTAGACTGTGCACTTGACCC<br>TCTCTCAGAAACAAAGTGTACGTTGAAATCCTTCACTGTAGAAAAAGGAATCTATCAAACTTCTAACT<br>TTAGAGTCCAACCAACAGAATCTATTGTTAGATTTCCTAATATTACAAACTTGTGCCCTTTTGGTGAA<br>GTTTTTAACGCCACCAGATTTGCATCTGTTTATGCTTGGAACAGGAAGAGAATCAGCAACTGTGTTGC<br>TGATTATTCTGTCCTATATAATTCCGCATCATTTTCCACTTTTAAGTGTTATGGAGTGTCTCCTACTA<br>AATTAAATGATCTCTGCTTTACTAATGTCTATGCAGATTCATTTGTAATTAGAGGTGATGAAGTCAGA<br>CAAATCGCTCCAGGGCAAACTGGAAAGATTGCTGATTATAATTATAAATTACCAGATGATTTTACAGG<br>CTGCGTTATAGCTTGGAATTCTAACAATCTTGATTCTAAGGTTGGTGGTAATTATAATTACCTGTATA<br>GATTGTTTAGGAAGTCTAATCTCAAACCTTTTGAGAGAGATATTTCAACTGAAATCTATCAGGCCGGT<br>AGCACACCTTGTAATGGTGTTGAAGGTTTTAATTGTTACTTTCCTTTACAATCATATGGTTTCCAACC<br>CACTAATGGTGTTGGTTACCAACCATACAGAGTAGTAGTACTTTCTTTTGAACTTCTACATGCACCAG<br>CAACTGTTTGTGGACCTAAAAAGTCTACTAATTTGGTTAAAAACAAATGTGTCAATTTCAACTTCAAT<br>GGTTTAACAGGCACAGGTGTTCTTACTGAGTCTAACAAAAAGTTTCTGCCTTTCCAACAATTTGGCAG<br>AGACATTGCTGACACTACTGATGCTGTCCGTGATCCACAGACACTTGAGATTCTTGACATTACACCAT<br>GTTCTTTTGGTGGTGTCAGTGTTATAACACCAGGAACAAATACTTCTAACCAGGTTGCTGTTCTTTAT<br>CAGGATGTTAACTGCACAGAAGTCCCTGTTGCTATTCATGCAGATCAACTTACTCCTACTTGGCGTGT<br>TTATTCTACAGGTTCTAATGTTTTTCAAACACGTGCAGGCTGTTTAATAGGGGCTGAACATGTCAACA<br>ACTCATATGAGTGTGACATACCCATTGGTGCAGGTATATGCGCTAGTTATCAGACTCAGACTAATTCT<br>CCTCGGCGGGCACGTAGTGTAGCTAGTCAATCCATCATTGCCTACACTATGTCACTTGGTGCAGAAAA<br>TTCAGTTGCTTACTCTAATAACTCTATTGCCATACCCACAAATTTTACTATTAGTGTTACCACAGAAA<br>TTCTACCAGTGTCTATGACCAAGACATCAGTAGATTGTACAATGTACATTTGTGGTGATTCAACTGAA<br>TGCAGCAATCTTTTGTTGCAATATGGCAGTTTTTGTACACAATTAAACCGTGCTTTAACTGGAATAGC<br>TGTTGAACAAGACAAAAACACCCAAGAAGTTTTTGCACAAGTCAAACAAATTTACAAAACACCACCAA<br>TTAAAGATTTTGGTGGTTTTAATTTTTCACAAATATTACCAGATCCATCAAAACCAAGCAAGAGGTCA<br>TTTATTGAAGATCTACTTTTCAACAAAGTGACACTTGCAGATGCTGGCTTCATCAAACAATATGGTGA<br>TTGCCTTGGTGATATTGCTGCTAGAGACCTCATTTGTGCACAAAAGTTTAACGGCCTTACTGTTTTGC<br>CACCTTTGCTCACAGATGAAATGATTGCTCAATACACTTCTGCACTGTTAGCGGGTACAATCACTTCT<br>GGTTGGACCTTTGGTGCAGGTGCTGCATTACAAATACCATTTGCTATGCAAATGGCTTATAGGTTTAA<br>TGGTATTGGAGTTACACAGAATGTTCTCTATGAGAACCAAAAATTGATTGCCAACCAATTTAATAGTG<br>CTATTGGCAAAATTCAAGACTCACTTTCTTCCACAGCAAGTGCACTTGGAAAACTTCAAGATGTGGTC<br>AACCAAAATGCACAAGCTTTAAACACGCTTGTTAAACAACTTAGCTCCAATTTTGGTGCAATTTCAAG<br>TGTTTTAAATGATATCCTTTCACGTCTTGACAAAGTTGAGGCTGAAGTGCAAATTGATAGGTTGATCA<br>CAGGCAGACTTCAAAGTTTGCAGACATATGTGACTCAACAATTAATTAGAGCTGCAGAAATCAGAGCT<br>TCTGCTAATCTTGCTGCTACTAAAATGTCAGAGTGTGTACTTGGACAATCAAAAAGAGTTGATTTTTG<br>TGGAAAGGGCTATCATCTTATGTCCTTCCCTCAGTCAGCACCTCATGGTGTAGTCTTCTTGCATGTGA<br>CTTATGTCCCTGCACAAGAAAAGAACTTCACAACTGCTCCTGCCATTTGTCATGATGGAAAAGCACAC<br>TTTCCTCGTGAAGGTGTCTTTGTTTCAAATGGCACACACTGGTTTGTAACACAAAGGAATTTTTATGA<br>ACCACAAATCATTACTACAGACAACACATTTGTGTCTGGTAACTGTGATGTTGTAATAGGAATTGTCA<br>ACAACACAGTTTATGATCCTTTGCAACCTGAATTAGACTCATTCAAGGAGGAGTTAGATAAATATTTT<br>AAGAATCATACATCACCAGATGTTGATTTAGGTGACATCTCTGGCATTAATGCTTCAGTTGTAAACAT<br>TCAAAAAGAAATTGACCGCCTCAATGAGGTTGCCAAGAATTTAAATGAATCTCTCATCGATCTCCAAG<br>AACTTGGAAAGTATGAGCAGTATATAAAATGGCCATGGTACATTTGGCTAGGTTTTATAGCTGGCTTG |

-continued

| Sequences |
|---|
| ATTGCCATAGTAATGGTGACAATTATGCTTTGCTGTATGACCAGTTGCTGTAGTTGTCTCAAGGGCTG<br>TTGTTCTTGTGGATCCTGCTGCAAATTTGATGAAGACGACTCTGAGCCAGTGCTCAAAGGAGTCAAAT<br>TACATTACACA**TAA** |
| SEQ ID NO: 3 Amino acid sequence of SARS-CoV-2 S RBD including<br>modification (N331A)<br>AITNLCPFGEVFNATRFASVYAWNRKRISNCVADYSVLYNSASFSTFKCYGVSPTKLNDLCFTNVYAD<br>SFVIRGDEVRQIAPGQTGKIADYNYKLPDDFTGCVIAWNSNNLDSKVGGNYNYLYRLFRKSNLKPFER<br>DISTEIYQAGSTPCNGVEGFNCYFPLQSYGFQPTNGVGYQPYRVVVLSFELLHAPATV |
| SEQ ID NO: 4 Nucleotide sequence for SEQ ID NO: 3<br>GCCATCACCAATCTGTGCCCTTTTGGCGAGGTGTTCAACGCCACCAGATTCGCCTCTGTGTACGCCTG<br>GAACCGGAAGCGGATCAGCAATTGCGTTGCCGACTACAGCGTGCTGTACAACTCTGCCAGCTTCTCCA<br>CCTTCAAGTGCTATGGCGTGTCTCCTACCAAGCTGAACGACCTGTGCTTCACCAACGTGTACGCTGAC<br>AGCTTCGTGATCAGAGGCGACGAAGTGAGACAGATTGCTCCTGGACAGACAGGCAAGATTGCCGATTA<br>CAACTACAAGCTCCCTGACGACTTCACAGGCTGTGTGATTGCCTGGAACAGCAACAACCTGGACAGCA<br>AAGTCGGAGGTAACTACAACTACCTGTACAGGCTGTTTCGGAAGTCCAACCTGAAGCCTTTCGAGAGA<br>GACATCAGCACCGAGATCTATCAGGCAGGCAGCACACCTTGCAATGGCGTGGAAGGCTTCAACTGCTA<br>CTTCCCACTGCAGTCCTACGGCTTCCAGCCTACAAATGGAGTGGGCTACCAGCCTTACAGAGTGGTGG<br>TGCTGAGCTTCGAGCTGCTGCATGCTCCTGCCACAGTG |
| SEQ ID NO: 5 Amino acid sequence of a part of SARS-CoV-2 S protein<br>S1 domain comprising SARS-CoV-2 S RBD including modification<br>(N331A)<br>RVQPTESIVRFPAITNLCPFGEVFNATRFASVYAWNRKRISNCVADYSVLYNSASFSTFKCYGVSPTK<br>LNDLCFTNVYADSFVIRGDEVRQIAPGQTGKIADYNYKLPDDFTGCVIAWNSNNLDSKVGGNYNYLYR<br>LFRKSNLKPFERDISTEIYQAGSTPCNGVEGFNCYFPLQSYGFQPTNGVGYQPYRVVVLSFELLHAPA<br>TVCGPKKSTNLVKNKCVNFNFNGLTGT |
| SEQ ID NO: 6 Nucleotide sequence for SEQ ID NO: 5<br>AGAGTGCAGCCCACAGAGTCTATCGTGCGGTTCCCTGCCATCACCAATCTGTGCCCTTTTGGCGAGGT<br>GTTCAACGCCACCAGATTCGCCTCTGTGTACGCCTGGAACCGGAAGCGGATCAGCAATTGCGTTGCCG<br>ACTACAGCGTGCTGTACAACTCTGCCAGCTTCTCCACCTTCAAGTGCTATGGCGTGTCTCCTACCAAG<br>CTGAACGACCTGTGCTTCACCAACGTGTACGCTGACAGCTTCGTGATCAGAGGCGACGAAGTGAGACA<br>GATTGCTCCTGGACAGACAGGCAAGATTGCCGATTACAACTACAAGCTCCCTGACGACTTCACAGGCT<br>GTGTGATTGCCTGGAACAGCAACAACCTGGACAGCAAAGTCGGAGGTAACTACAACTACCTGTACAGG<br>CTGTTTCGGAAGTCCAACCTGAAGCCTTTCGAGAGAGACATCAGCACCGAGATCTATCAGGCAGGCAG<br>CACACCTTGCAATGGCGTGGAAGGCTTCAACTGCTACTTCCCACTGCAGTCCTACGGCTTCCAGCCTA<br>CAAATGGAGTGGGCTACCAGCCTTACAGAGTGGTGGTGCTGAGCTTCGAGCTGCTGCATGCTCCTGCC<br>ACAGTGTGCGGACCTAAGAAAAGCACCAACCTGGTGAAGAACAAATGCGTGAACTTCAACTTCAATGG<br>CCTGACAGGCACC |
| SEQ ID NO: 7 Human IgGH secretion signal peptide (including start M)<br>MEFGLSWVFLVAILKGVQC |
| SEQ ID NO: 8 Nucleotide sequence for SEQ ID NO: 7<br>ATGGAATTCGGACTGAGCTGGGTGTTCCTGGTCGCCATTCTGAAAGGCGTGCAGTGC |
| SEQ ID NO: 9 Amino acid sequence of a part of SARS-CoV-2 S<br>protein S1 domain comprising SARS-CoV-2 S RBD including<br>modification (N331A) plus secretion signal peptide<br>(including start M); "SARS-2 S-RBD-1"<br>MEFGLSWVFLVAILKGVQCRVQPTESIVRFPAITNLCPFGEVFNATRFASVYAWNRKRISNCVADYSV<br>LYNSASFSTFKCYGVSPTKLNDLCFTNVYADSFVIRGDEVRQIAPGQTGKIADYNYKLPDDFTGCVIA<br>WNSNNLDSKVGGNYNYLYRLFRKSNLKPFERDISTEIYQAGSTPCNGVEGFNCYFPLQSYGFQPTNGV<br>GYQPYRVVVLSFELLHAPATVCGPKKSTNLVKNKCVNFNFNGLTGT |
| SEQ ID NO: 10 Nucleotide sequence for SEQ ID NO: 9<br>(plus stop codons in bold)<br>ATGGAATTCGGACTGAGCTGGGTGTTCCTGGTCGCCATTCTGAAAGGCGTGCAGTGCAGAGTGCAGCC<br>CACAGAGTCTATCGTGCGGTTCCCTGCCATCACCAATCTGTGCCCTTTTGGCGAGGTGTTCAACGCCA<br>CCAGATTCGCCTCTGTGTACGCCTGGAACCGGAAGCGGATCAGCAATTGCGTTGCCGACTACAGCGTG<br>CTGTACAACTCTGCCAGCTTCTCCACCTTCAAGTGCTATGGCGTGTCTCCTACCAAGCTGAACGACCT<br>GTGCTTCACCAACGTGTACGCTGACAGCTTCGTGATCAGAGGCGACGAAGTGAGACAGATTGCTCCTG<br>GACAGACAGGCAAGATTGCCGATTACAACTACAAGCTCCCTGACGACTTCACAGGCTGTGTGATTGCC<br>TGGAACAGCAACAACCTGGACAGCAAAGTCGGAGGTAACTACAACTACCTGTACAGGCTGTTTCGGAA<br>GTCCAACCTGAAGCCTTTCGAGAGAGACATCAGCACCGAGATCTATCAGGCAGGCAGCACACCTTGCA<br>ATGGCGTGGAAGGCTTCAACTGCTACTTCCCACTGCAGTCCTACGGCTTCCAGCCTACAAATGGAGTG<br>GGCTACCAGCCTTACAGAGTGGTGGTGCTGAGCTTCGAGCTGCTGCATGCTCCTGCCACAGTGTGCGG<br>ACCTAAGAAAAGCACCAACCTGGTGAAGAACAAATGCGTGAACTTCAACTTCAATGGCCTGACAGGCA<br>CC**TGATAA** |
| SEQ ID NO: 11 Amino acid sequence of SARS-CoV-2 protein 3a<br>(YP_009724391.1)<br>MDLFMRIFTIGTVTLKQGEIKDATPSDFVRATATIPIQASLPFGWLIVGVALLAVFQSASKIITLKKR<br>WQLALSKGVHFVCNLLLLFVTVYSHLLLVAAGLEAPFLYLYALVYFLQSINFVRIIMRLWLCWKCRSK<br>NPLLYDANYFLCWHTNCYDYCIPYNSVTSSIVITSGDGTTSPISEHDYQIGGYTEKWESGVKDCVVLH |

-continued

Sequences

SYFTSDYYQLYSTQLSTDTGVEHVTFFIYNKIVDEPEEHVQIHTIDGSSGVVNPVMEPIYDEPTTTTS
VPL

SEQ ID NO: 12 Amino acid sequence of SARS CoV-2 protein E
(YP_009724392.1)
MYSFVSEETGTLIVNSVLLFLAFVVFLLVTLAILTALRLCAYCCNIVNVSLVKPSFYVYSRVKNLNSS
RVPDLLV SEQ ID NO: 13 Amino acid sequence of SARS CoV-2 protein M
(YP_009724393.1)
MADSNGTITVEELKKLLEQWNLVIGFLFLTWICLLQFAYANRNRFLYIIKLIFLWLLWPVTLACFVLA
AVYRINWITGGIAIAMACLVGLMWLSYFIASFRLFARTRSMWSFNPETNILLNVPLHGTILTRPLLES
ELVIGAVILRGHLRIAGHHLGRCDIKDLPKEITVATSRTLSYYKLGASQRVAGDSGFAAYSRYRIGNY
KLNTDHSSSSDNIALLVQ SEQ ID NO: 14 Amino acid sequence of SARS-CoV-2 protein 3a-1
fragment
FQSASKIITLKKRWQLALSKGVHFVCNL SEQ ID NO: 15 Amino acid sequence of SARS-CoV-2 protein 3a-2
fragment
PISEHDYQIGGYTEKWESGVKDCVVLHSYFTSDYYQLYSTQLSTDTGVEHVTFFIYNKIVDEPEEHVQ
IHTIDGSSGVVNPVMEPIYDEPTTTTSVPL SEQ ID NO: 16 Amino acid sequence of SARS-CoV-2 protein E
fragment
RLCAYCCNIVNVSLVKPSFYVYSRVKNLNSSRVPDL SEQ ID NO: 17 Amino acid sequence of SARS-CoV-2 protein M-1
fragment
FAYANRNRFLYIIKL SEQ ID NO: 18 Amino acid sequence of SARS-CoV-2 protein M-2
fragment
SYFIASFRLFARTRSMWSFNPETNILLNVPLHGTILTRPLLESELVIGAVILRGHLRIAGHHLGRCDI
KDLPKEITVATSRTLSYYKLGASQRVAGDSGFAAYSRYRIGNYKLNTDHSS SEQ ID NO: 19 Amino acid sequence of SARS-CoV-2 protein 3a-1,
3a-2, protein E, and protein M-1, M-2 fragments fused together
(including start M)
MFQSASKIITLKKRWQLALSKGVHFVCNLPISEHDYQIGGYTEKWESGVKDCVVLHSYFTSDYYQLYS
TQLSTDTGVEHVTFFIYNKIVDEPEEHVQIHTIDGSSGVVNPVMEPIYDEPTTTTSVPLRLCAYCCNI
VNVSLVKPSFYVYSRVKNLNSSRVPDLFAYANRNRFLYIIKLSYFIASFRLFARTRSMWSFNPETNIL
LNVPLHGTILTRPLLESELVIGAVILRGHLRIAGHHLGRCDIKDLPKEITVATSRTLSYYKLGASQRV
AGDSGFAAYSRYRIGNYKLNTDHSS SEQ ID NO: 20 Amino acid sequence of SARS-CoV-2 3aEM fusion
protein including modifications (A131W, Y132F and S179D,
Y180F) (including start M); "SARS-2 3aEM-1"
MFQSASKIITLKKRWQLALSKGVHFVCNLPISEHDYQIGGYTEKWESGVKDCVVLHSYFTSDYYQLYS
TQLSTDTGVEHVTFFIYNKIVDEPEEHVQIHTIDGSSGVVNPVMEPIYDEPTTTTSVPLRLCWFCCNI
VNVSLVKPSFYVYSRVKNLNSSRVPDLFAYANRNRFLYIIKLDFFIASFRLFARTRSMWSFNPETNIL
LNVPLHGTILTRPLLESELVIGAVILRGHLRIAGHHLGRCDIKDLPKEITVATSRTLSYYKLGASQRV
AGDSGFAAYSRYRIGNYKLNTDHSS SEQ ID NO: 21 Nucleotide sequence for SEQ ID NO: 20
(plus stop codons in bold)
ATGTTTCAGTCTGCCAGCAAGATCATCACCCTGAAGAAGAGGTGGCAGCTGGCTCTGTCTAAAGGTGT
GCACTTCGTGTGCAACCTGCCTATCAGCGAGCACGACTATCAGATCGGAGGCTACACCGAGAAGTGGG
AGTCTGGCGTGAAGGACTGTGTGGTGCTGCACAGCTACTTCACCAGCGACTACTACCAGCTGTACTCT
ACCCAGCTGAGCACCGACACAGGCGTGGAACACGTGACCTTCTTCATCTACAACAAGATCGTGGACGA
ACCCGAAGAACACGTGCAGATCCACACAATCGATGGCAGCTCTGGCGTGGTCAACCCAGTGATGGAAC
CCATCTACGACGAGCCTACCACCACCACAAGCGTGCCTCTGAGACTGTGCTGGTTCTGCTGCAACATC
GTGAACGTGTCCCTGGTCAAGCCCAGCTTCTACGTGTACAGCAGAGTGAAGAACCTGAACAGCAGCAG
GGTTCCCGACCTGTTCGCCTACGCCAACAGAAACAGATTCCTGTACATCATCAAGCTGGATTTCTTCA
TCGCCAGCTTCAGACTGTTCGCACGGACCAGATCCATGTGGTCCTTCAATCCCGAGACAAACATCCTG
CTGAATGTGCCTCTGCACGGCACCATCCTGACAAGACCTCTGCTGGAAAGCGAGCTGGTTATCGGTGC
CGTGATCCTGAGAGGCCACCTGAGAATTGCAGGACACCACCTGGGCAGATGCGACATCAAGGACCTGC
CAAAAGAAATCACCGTGGCCACCAGCAGGACCCTGAGCTACTACAAGCTGGGAGCCTCTCAGAGAGTG
GCTGGCGATTCTGGATTTGCAGCCTACAGCAGATACCGGATCGGCAACTACAAACTGAATACCGACCA
CAGCAGCTAATGA

SEQ ID NO: 22 Amino acid sequence of SARS-CoV-2 S full-length
protein including modifications (K986P, V987P, GSAS amino
acid stretch)
SQCVNLTTRTQLPPAYTNSFTRGVYYPDKVFRSSVLHSTQDLFLPFFSNVTWFHAIHVSGTNGTKRFD
NPVLPFNDGVYFASTEKSNIIRGWIFGTTLDSKTQSLLIVNNATNVVIKVCEFQFCNDPFLGVYYHKN -continued

| Sequences |
|---|
| NKSWMESEFRVYSSANNCTFEYVSQPFLMDLEGKQGNFKNLREFVFKNIDGYFKIYSKHTPINLVRDL<br>PQGFSALEPLVDLPIGINITRFQTLLALHRSYLTPGDSSSGWTAGAAAYYVGYLQPRTFLLKYNENGT<br>ITDAVDCALDPLSETKCTLKSFTVEKGIYQTSNFRVQPTESIVRFPNITNLCPFGEVFNATRFASVYA<br>WNRKRISNCVADYSVLYNSASFSTFKCYGVSPTKLNDLCFTNVYADSFVIRGDEVRQIAPGQTGKIAD<br>YNYKLPDDFTGCVIAWNSNNLDSKVGGNYNYLYRLFRKSNLKPFERDISTEIYQAGSTPCNGVEGFNC<br>YFPLQSYGFQPTNGVGYQPYRVVVLSFELLHAPATVCGPKKSTNLVKNKCVNFNFNGLTGTGVLTESN<br>KKFLPFQQFGRDIADTTDAVRDPQTLEILDITPCSFGGVSVITPGTNTSNQVAVLYQDVNCTEVPVAI<br>HADQLTPTWRVYSTGSNVFQTRAGCLIGAEHVNNSYECDIPIGAGICASYQTQTNSPGSASSVASQSI<br>IAYTMSLGAENSVAYSNNSIAIPTNFTISVTTEILPVSMTKTSVDCTMYICGDSTECSNLLLQYGSFC<br>TQLNRALTGIAVEQDKNTQEVFAQVKQIYKTPPIKDFGGFNFSQILPDPSKPSKRSFIEDLLFNKVTL<br>ADAGFIKQYGDCLGDIAARDLICAQKFNGLTVLPPLLTDEMIAQYTSALLAGTITSGWTFGAGAALQI<br>PFAMQMAYRFNGIGVTQNVLYENQKLIANQFNSAIGKIQDSLSSTASALGKLQDVVNQNAQALNTLVK<br>QLSSNFGAISSVLNDILSRLDPPEAEVQIDRLITGRLQSLQTYVTQQLIRAAEIRASANLAATKMSEC<br>VLGQSKRVDFCGKGYHLMSFPQSAPHGVVFLHVTYVPAQEKNFTTAPAICHDGKAHFPREGVFVSNGT<br>HWFVTQRNFYEPQIITTDNTFVSGNCDVVIGIVNNTVYDPLQPELDSFKEELDKYFKNHTSPDVDLGD<br>ISGINASVVNIQKEIDRLNEVAKNLNESLIDLQELGKYEQYIKWPWYIWLGFIAGLIAIVMVTIMLCC<br>MTSCCSCLKGCCSCGSCCKFDEDDSEPVLKGVKLHYT |
| SEQ ID NO: 23 Nucleotide sequence for SEQ ID NO: 22<br>(plus stop codons in bold)<br>AGCCAGTGTGTGAACCTGACCACCAGAACACAGCTGCCTCCAGCCTACACCAACAGCTTTACCAGAGG<br>CGTGTACTATCCCGACAAGGTGTTCAGATCCAGCGTGCTGCACTCTACCCAGGACCTGTTCCTGCCTT<br>TCTTCAGCAACGTGACCTGGTTCCACGCCATCCACGTGAGCGGTACCAATGGCACCAAGAGATTCGAC<br>AATCCCGTGCTGCCCTTCAACGACGGAGTGTACTTTGCCAGCACCGAGAAGTCCAACATCATCAGAGG<br>CTGGATCTTCGGCACCACACTGGACAGCAAGACCCAGAGCCTGCTGATCGTGAACAACGCCACCAACG<br>TGGTCATCAAAGTGTGCGAGTTCCAGTTCTGCAACGATCCCTTCCTGGGAGTCTACTACCACAAGAAC<br>AACAAGAGCTGGATGGAAAGCGAGTTCAGAGTGTACAGCTCTGCCAACAACTGCACCTTCGAGTACGT<br>GTCCCAGCCTTTCCTGATGGACCTGGAAGGCAAGCAGGGCAATTTCAAGAATCTCCGAGAGTTCGTGT<br>TCAAGAACATCGACGGCTACTTCAAGATCTACAGCAAGCACACACCTATCAACCTCGTGAGGGATCTG<br>CCTCAGGGCTTCTCTGCTCTGGAACCTCTGGTGGATCTGCCCATCGGCATCAACATCACTCGGTTTCA<br>GACACTGCTGGCACTGCACAGAAGCTACCTGACACCTGGCGATAGCAGCAGCGGATGGACAGCTGGTG<br>CTGCAGCTTACTATGTGGGCTACCTGCAGCCTAGAACCTTCCTGCTGAAGTACAACGAGAACGGCACC<br>ATCACCGATGCCGTGGATTGTGCTCTGGATCCTCTGAGCGAGACAAAGTGCACCCTGAAGTCCTTCAC<br>CGTGGAGAAGGGCATCTACCAGACCAGCAACTTCAGGGTGCAGCCCACCGAATCCATCGTGCGGTTCC<br>CTAACATCACCAATCTGTGTCCCTTTGGCGAGGTGTTCAATGCCACCAGATTCGCCTCTGTGTACGCC<br>TGGAACCGGAAGCGGATCAGCAATTGCGTTGCCGACTACTCCGTGCTGTACAACTCAGCCAGCTTCAG<br>CACCTTCAAGTGCTACGGAGTGAGCCCTACCAAGCTGAACGACCTGTGCTTCACAAACGTGTATGCTG<br>ACAGCTTCGTGATCAGAGGAGATGAAGTGAGGCAGATTGCTCCTGGACAGACAGGCAAGATTGCAGAT<br>TACAACTACAAGCTGCCTGACGACTTCACAGGCTGTGTGATTGCCTGGAACAGCAACAACCTGGACTC<br>CAAAGTCGGAGGCAACTACAACTACCTGTACAGACTGTTCAGGAAGTCCAATCTGAAGCCCTTCGAAC<br>GGGACATCTCCACCGAGATCTATCAGGCTGGCAGCACACCTTGTAATGGAGTGGAAGGCTTCAACTGC<br>TACTTCCCACTGCAGTCCTACGGCTTTCAGCCCACAAATGGCGTGGGCTATCAGCCCTACAGAGTGGT<br>GGTGCTGAGCTTCGAACTGCTGCATGCTCCTGCCACAGTGTGCGGACCTAAGAAATCCACCAATCTCG<br>TGAAGAACAAATGCGTGAACTTCAACTTCAACGGTCTGACCGGTACAGGCGTGCTGACAGAGAGCAAC<br>AAGAAGTTCCTGCCATTCCAGCAGTTTGGCAGGGATATCGCAGATACCACAGACGCTGTTAGAGATCC<br>ACAGACACTGGAAATCCTGGACATCACACCTTGCAGCTTCGGAGGCGTGTCTGTGATCACACCTGGCA<br>CCAACACCAGCAATCAGGTGGCAGTTCTGTACCAGGACGTGAACTGTACCGAAGTTCCCGTGGCCATT<br>CATGCCGATCAGCTGACACCTACATGGAGGGTGTACTCCACCGGAAGCAATGTGTTTCAGACCAGAGC<br>TGGCTGTCTGATCGGAGCCGAGCACGTGAACAATAGCTACGAGTGCGACATCCCTATCGGAGCTGGCA<br>TCTGTGCCAGCTACCAGACACAGACAAACAGCCCTGGCTCTGCCTCTTCCGTGGCCAGCCAGTCCATC<br>ATTGCCTACACAATGTCTCTGGGAGCCGAGAACAGCGTGGCCTACTCCAACAACTCTATCGCTATCCC<br>TACCAACTTCACAATCAGCGTGACCACAGAGATCCTGCCTGTGTCCATGACCAAGACCAGCGTGGACT<br>GCACCATGTACATCTGTGGCGATTCCACCGAGTGCTCCAACCTGCTGCTGCAGTACGGCAGCTTCTGC<br>ACCCAGCTGAATAGAGCCCTGACAGGGATCGCTGTGGAACAGGACAAGAACACCCAAGAGGTGTTCGC<br>ACAAGTGAAGCAGATCTACAAGACACCTCCTATCAAGGACTTCGGAGGATTCAACTTTAGCCAGATTC<br>TGCCTGATCCTAGCAAGCCAAGCAAGCGGAGCTTCATCGAGGACCTGCTGTTCAACAAAGTGACACTT<br>GCCGACGCTGGCTTCATCAAGCAGTATGGCGATTGTCTGGGAGACATTGCTGCCAGGGATCTGATTTG<br>TGCCCAGAAGTTCAACGGACTGACAGTGCTGCCTCCTCTGCTGACCGATGAGATGATCGCTCAGTACA<br>CATCTGCCCTGCTGGCTGGCACAATCACAAGTGGCTGGACATTTGGAGCTGGAGCTGCTCTGCAGATT<br>CCCTTTGCTATGCAGATGGCCTACCGGTTCAACGGCATCGGAGTGACCCAGAATGTGCTGTACGAGAA<br>CCAGAAGCTGATCGCCAACCAGTTCAACTCTGCCATCGGCAAGATCCAGGACAGCCTGAGCAGCACAG<br>CAAGCGCACTGGGAAAGCTGCAGGACGTGGTCAACCAGAATGCCCAGGCACTGAACACCCTGGTCAAG<br>CAGCTGTCCTCCAACTTCGGAGCCATCAGCTCTGTGCTGAACGATATCCTGAGCAGACTGGACCCTCC<br>TGAAGCCGAGGTGCAGATCGACAGGCTGATCACAGGCAGACTGCAGAGCCTCCAGACATACGTGACCC<br>AGCAGCTGATCAGAGCTGCCGAGATTAGAGCCTCTGCCAATCTGGCAGCCACCAAGATGTCTGAGTGT<br>GTGCTGGGACAGAGCAAGAGAGTGGACTTCTGTGGCAAGGGCTACCACCTGATGAGCTTCCCTCAGTC<br>TGCACCTCATGGCGTGGTGTTTCTGCACGTGACATATGTGCCAGCTCAAGAGAAGAACTTCACCACCG<br>CTCCAGCCATCTGCCACGACGGTAAAGCCCACTTTCCTAGAGAAGGCGTGTTCGTGTCCAACGGCACC<br>CATTGGTTCGTGACACAGCGGAACTTCTACGAGCCTCAGATCATCACCACCGACAACACCTTCGTGTC<br>TGGCAACTGCGACGTCGTGATCGGCATTGTCAACAATACCGTGTACGACCCTCTGCAGCCAGAGCTCG<br>ACAGCTTCAAAGAGGAACTGGACAAGTACTTCAAGAACCACACAAGCCCTGACGTGGACCTGGGAGAT<br>ATCAGCGGAATCAATGCCAGCGTCGTGAACATCCAGAAAGAGATTGACAGACTGAACGAGGTGGCCAA<br>GAATCTGAACGAGAGCCTGATCGACCTGCAAGAACTTGGGAAGTACGAGCAGTACATCAAGTGGCCTT<br>GGTACATCTGGCTGGGCTTCATCGCAGGACTGATTGCCATCGTGATGGTCACAATCATGCTGTGTTGC<br>ATGACCAGCTGCTGTAGCTGTCTGAAGGGCTGTTGTAGCTGTGGCAGCTGCTGCAAGTTCGACGAGGA<br>CGATTCTGAGCCAGTGCTGAAAGGCGTGAAACTGCACTACACA**TAGTAA** |

-continued

| Sequences |
|---|
| SEQ ID NO: 24 Amino acid sequence of SARS-CoV-2 S full-length protein including modifications (K986P, V987P, GSAS amino acid stretch) plus the native signal peptide of SARS-CoV-2 S protein (including start M); “SARS-2 S-FS-1”<br>MFVFLVLLPLVSSQCVNLTTRTQLPPAYTNSFTRGVYYPDKVFRSSVLHSTQDLFLPFFSNVTWFHAI<br>HVSGTNGTKRFDNPVLPFNDGVYFASTEKSNIIRGWIFGTTLDSKTQSLLIVNNATNVVIKVCEFQFC<br>NDPFLGVYYHKNNKSWMESEFRVYSSANNCTFEYVSQPFLMDLEGKQGNFKNLREFVFKNIDGYFKIY<br>SKHTPINLVRDLPQGFSALEPLVDLPIGINITRFQTLLALHRSYLTPGDSSSGWTAGAAAYYVGYLQP<br>RTFLLKYNENGTITDAVDCALDPLSETKCTLKSFTVEKGIYQTSNFRVQPTESIVRFPNITNLCPFGE<br>VFNATRFASVYAWNRKRISNCVADYSVLYNSASFSTFKCYGVSPTKLNDLCFTNVYADSFVIRGDEVR<br>QIAPGQTGKIADYNYKLPDDFTGCVIAWNSNNLDSKVGGNYNYLYRLFRKSNLKPFERDISTEIYQAG<br>STPCNGVEGFNCYFPLQSYGFQPTNGVGYQPYRVVVLSFELLHAPATVCGPKKSTNLVKNKCVNFNFN<br>GLTGTGVLTESNKKFLPFQQFGRDIADTTDAVRDPQTLEILDITPCSFGGVSVITPGTNTSNQVAVLY<br>QDVNCTEVPVAIHADQLTPTWRVYSTGSNVFQTRAGCLIGAEHVNNSYECDIPIGAGICASYQTQTNS<br>PGSASSVASQSIIAYTMSLGAENSVAYSNNSIAIPTNFTISVTTEILPVSMTKTSVDCTMYICGDSTE<br>CSNLLLQYGSFCTQLNRALTGIAVEQDKNTQEVFAQVKQIYKTPPIKDFGGFNFSQILPDPSKPSKRS<br>FIEDLLFNKVTLADAGFIKQYGDCLGDIAARDLICAQKFNGLTVLPPLLTDEMIAQYTSALLAGTITS<br>GWTFGAGAALQIPFAMQMAYRFNGIGVTQNVLYENQKLIANQFNSAIGKIQDSLSSTASALGKLQDVV<br>NQNAQALNTLVKQLSSNFGAISSVLNDILSRLDPPEAEVQIDRLITGRLQSLQTYVTQQLIRAAEIRA<br>SANLAATKMSECVLGQSKRVDFCGKGYHLMSFPQSAPHGVVFLHVTYVPAQEKNFTTAPAICHDGKAH<br>FPREGVFVSNGTHWFVTQRNFYEPQIITTDNTFVSGNCDVVIGIVNNTVYDPLQPELDSFKEELDKYF<br>KNHTSPDVDLGDISGINASVVNIQKEIDRLNEVAKNLNESLIDLQELGKYEQYIKWPWYIWLGFIAGL<br>IAIVMVTIMLCCMTSCCSCLKGCCSCGSCCKFDEDDSEPVLKGVKLHYT |
| SEQ ID NO: 25 Nucleotide sequence for SEQ ID NO: 24 (plus stop codons in bold)<br>ATGTTCGTCTTCCTGGTCCTGCTCCCTCTGGTGTCCAGCCAGTGTGTGAACCTGACCACCAGAACACA<br>GCTGCCTCCAGCCTACACCAACAGCTTTACCAGAGGCGTGTACTATCCCGACAAGGTGTTCAGATCCA<br>GCGTGCTGCACTCTACCCAGGACCTGTTCCTGCCTTTCTTCAGCAACGTGACCTGGTTCCACGCCATC<br>CACGTGAGCGGTACCAATGGCACCAAGAGATTCGACAATCCCGTGCTGCCCTTCAACGACGGAGTGTA<br>CTTTGCCAGCACCGAGAAGTCCAACATCATCAGAGGCTGGATCTTCGGCACCACACTGGACAGCAAGA<br>CCCAGAGCCTGCTGATCGTGAACAACGCCACCAACGTGGTCATCAAAGTGTGCGAGTTCCAGTTCTGC<br>AACGATCCCTTCCTGGGAGTCTACTACCACAAGAACAACAAGAGCTGGATGGAAAGCGAGTTCAGAGT<br>GTACAGCTCTGCCAACAACTGCACCTTCGAGTACGTGTCCCAGCCTTTCCTGATGGACCTGGAAGGCA<br>AGCAGGGCAATTTCAAGAATCTCCGAGAGTTCGTGTTCAAGAACATCGACGGCTACTTCAAGATCTAC<br>AGCAAGCACACACCTATCAACCTCGTGAGGGATCTGCCTCAGGGCTTCTCTGCTCTGGAACCTCTGGT<br>GGATCTGCCCATCGGCATCAACATCACTCGGTTTCAGACACTGCTGGCACTGCACAGAAGCTACCTGA<br>CACCTGGCGATAGCAGCAGCGGATGGACAGCTGGTGCTGCAGCTTACTATGTGGGCTACCTGCAGCCT<br>AGAACCTTCCTGCTGAAGTACAACGAGAACGGCACCATCACCGATGCCGTGGATTGTGCTCTGGATCC<br>TCTGAGCGAGACAAAGTGCACCCTGAAGTCCTTCACCGTGGAGAAGGGCATCTACCAGACCAGCAACT<br>TCAGGGTGCAGCCCACCGAATCCATCGTGCGGTTCCCTAACATCACCAATCTGTGTCCCTTTGGCGAG<br>GTGTTCAATGCCACCAGATTCGCCTCTGTGTACGCCTGGAACCGGAAGCGGATCAGCAATTGCGTTGC<br>CGACTACTCCGTGCTGTACAACTCAGCCAGCTTCAGCACCTTCAAGTGCTACGGAGTGAGCCCTACCA<br>AGCTGAACGACCTGTGCTTCACAAACGTGTATGCTGACAGCTTCGTGATCAGAGGAGATGAAGTGAGG<br>CAGATTGCTCCTGGACAGACAGGCAAGATTGCAGATTACAACTACAAGCTGCCTGACGACTTCACAGG<br>CTGTGTGATTGCCTGGAACAGCAACAACCTGGACTCCAAAGTCGGAGGCAACTACAACTACCTGTACA<br>GACTGTTCAGGAAGTCCAATCTGAAGCCCTTCGAACGGGACATCTCCACCGAGATCTATCAGGCTGGC<br>AGCACACCTTGTAATGGAGTGGAAGGCTTCAACTGCTACTTCCCACTGCAGTCCTACGGCTTTCAGCC<br>CACAAATGGCGTGGGCTATCAGCCCTACAGAGTGGTGGTGCTGAGCTTCGAACTGCTGCATGCTCCTG<br>CCACAGTGTGCGGACCTAAGAAATCCACCAATCTCGTGAAGAACAAATGCGTGAACTTCAACTTCAAC<br>GGTCTGACCGGTACAGGCGTGCTGACAGAGAGCAACAAGAAGTTCCTGCCATTCCAGCAGTTTGGCAG<br>GGATATCGCAGATACCACAGACGCTGTTAGAGATCCACAGACACTGGAAATCCTGGACATCACACCTT<br>GCAGCTTCGGAGGCGTGTCTGTGATCACACCTGGCACCAACACCAGCAATCAGGTGGCAGTTCTGTAC<br>CAGGACGTGAACTGTACCGAAGTTCCCGTGGCCATTCATGCCGATCAGCTGACACCTACATGGAGGGT<br>GTACTCCACCGGAAGCAATGTGTTTCAGACCAGAGCTGGCTGTCTGATCGGAGCCGAGCACGTGAACA<br>ATAGCTACGAGTGCGACATCCCTATCGGAGCTGGCATCTGTGCCAGCTACCAGACACAGACAAACAGC<br>CCTGGCTCTGCCTCTTCCGTGGCCAGCCAGTCCATCATTGCCTACACAATGTCTCTGGGAGCCGAGAA<br>CAGCGTGGCCTACTCCAACAACTCTATCGCTATCCCTACCAACTTCACAATCAGCGTGACCACAGAGA<br>TCCTGCCTGTGTCCATGACCAAGACCAGCGTGGACTGCACCATGTACATCTGTGGCGATTCCACCGAG<br>TGCTCCAACCTGCTGCTGCAGTACGGCAGCTTCTGCACCCAGCTGAATAGAGCCCTGACAGGGATCGC<br>TGTGGAACAGGACAAGAACACCCAAGAGGTGTTCGCACAAGTGAAGCAGATCTACAAGACACCTCCTA<br>TCAAGGACTTCGGAGGATTCAACTTTAGCCAGATTCTGCCTGATCCTAGCAAGCCAAGCAAGCGGAGC<br>TTCATCGAGGACCTGCTGTTCAACAAAGTGACACTTGCCGACGCTGGCTTCATCAAGCAGTATGGCGA<br>TTGTCTGGGAGACATTGCTGCCAGGGATCTGATTTGTGCCCAGAAGTTCAACGGACTGACAGTGCTGC<br>CTCCTCTGCTGACCGATGAGATGATCGCTCAGTACACATCTGCCCTGCTGGCTGGCACAATCACAAGT<br>GGCTGGACATTTGGAGCTGGAGCTGCTCTGCAGATTCCCTTTGCTATGCAGATGGCCTACCGGTTCAA<br>CGGCATCGGAGTGACCCAGAATGTGCTGTACGAGAACCAGAAGCTGATCGCCAACCAGTTCAACTCTG<br>CCATCGGCAAGATCCAGGACAGCCTGAGCAGCACAGCAAGCGCACTGGGAAAGCTGCAGGACGTGGTC<br>AACCAGAATGCCCAGGCACTGAACACCCTGGTCAAGCAGCTGTCCTCCAACTTCGGAGCCATCAGCTC<br>TGTGCTGAACGATATCCTGAGCAGACTGGACCCTCCTGAAGCCGAGGTGCAGATCGACAGGCTGATCA<br>CAGGCAGACTGCAGAGCCTCCAGACATACGTGACCCAGCAGCTGATCAGAGCTGCCGAGATTAGAGCC<br>TCTGCCAATCTGGCAGCCACCAAGATGTCTGAGTGTGTGCTGGGACAGAGCAAGAGAGTGGACTTCTG<br>TGGCAAGGGCTACCACCTGATGAGCTTCCCTCAGTCTGCACCTCATGGCGTGGTGTTTCTGCACGTGA<br>CATATGTGCCAGCTCAAGAGAAGAACTTCACCACCGCTCCAGCCATCTGCCACGACGGTAAAGCCCAC<br>TTTCCTAGAGAAGGCGTGTTCGTGTCCAACGGCACCCATTGGTTCGTGACACAGCGGAACTTCTACGA<br>GCCTCAGATCATCACCACCGACAACACCTTCGTGTCTGGCAACTGCGACGTCGTGATCGGCATTGTCA<br>ACAATACCGTGTACGACCCTCTGCAGCCAGAGCTCGACAGCTTCAAAGAGGAACTGGACAAGTACTTC |

-continued

| Sequences |
| --- |
| AAGAACCACACAAGCCCTGACGTGGACCTGGGAGATATCAGCGGAATCAATGCCAGCGTCGTGAACAT<br>CCAGAAAGAGATTGACAGACTGAACGAGGTGGCCAAGAATCTGAACGAGAGCCTGATCGACCTGCAAG<br>AACTTGGGAAGTACGAGCAGTACATCAAGTGGCCTTGGTACATCTGGCTGGGCTTCATCGCAGGACTG<br>ATTGCCATCGTGATGGTCACAATCATGCTGTGTTGCATGACCAGCTGCTGTAGCTGTCTGAAGGGCTG<br>TTGTAGCTGTGGCAGCTGCTGCAAGTTCGACGAGGACGATTCTGAGCCAGTGCTGAAAGGCGTGAAAC<br>TGCACTACACA**TAGTAA** |
| SEQ ID NO: 26 Nucleic acid sequence of Pr13.5long promoter<br>TAAAAATAGAAACTATAATCATATAATAGTGTAGGTTGGTAGTATTGCTCTTGTGACTAGAGACTTTA<br>GTTAAGGTACTGTAAAAATAGAAACTATAATCATATAATAGTGTAGGTTGGTAGTA |
| SEQ ID NO: 27 Nucleic acid sequence of Pr1328 promoter<br>TATATTATTAAGTGTGGTGTTTGGTCGATGTAAAATTTTTGTCGATAAAAATTAAAAAATAACTTAAT<br>TTATTATTGATCTCGTGTGTACAACCGAAATC |

We claim:

1. A recombinant Modified Vaccinia Virus Ankara (MVA), comprising a nucleic acid sequence encoding an amino acid sequence of a severe acute respiratory syndrome coronavirus 2 (SARS-CoV-2) spike (S) full-length protein, wherein the amino acid sequence of the SARS-CoV-2 S full-length protein is as set forth in SEQ ID NO: 22 or 24.

2. A recombinant Modified Vaccinia Virus Ankara (MVA), comprising a nucleic acid sequence encoding an amino acid sequence of a severe acute respiratory syndrome coronavirus 2 (SARS-CoV-2) spike (S) full-length protein, wherein the nucleic acid sequence is as set forth in SEQ ID NO: 23 or 25.

3. A pharmaceutical composition, or a vaccine, comprising the recombinant MVA of claim 1, further comprising a pharmaceutically acceptable carrier or excipient.

4. A method for inducing an immune response to a coronavirus in a subject, comprising the step of administering to the subject the pharmaceutical composition or vaccine of claim 3.

5. The method of claim 4, wherein said coronavirus is SARS-CoV-2.

6. The method of claim 4, wherein said immune response prevents or treats a viral infection that is coronavirus disease 19 (COVID-19).

7. The method of claim 4, further comprising a boosting administration of the recombinant MVA in a homologous prime-boost vaccination regimen.

8. A pharmaceutical composition, or a vaccine, comprising the recombinant MVA of claim 2, further comprising a pharmaceutically acceptable carrier or excipient.

9. A method for inducing an immune response to a coronavirus in a subject, comprising the step of administering to the subject the pharmaceutical composition or vaccine of claim 8.

10. The method of claim 9, wherein said coronavirus is SARS-CoV-2.

11. The method of claim 9, wherein said immune response prevents or treats a viral infection that is coronavirus disease 19 (COVID-19).

12. The method of claim 9, further comprising a boosting administration of the recombinant MVA in a homologous prime-boost vaccination regimen.

13. The recombinant MVA of claim 1 wherein said amino acid sequence is as set forth in SEQ ID NO:22.

14. The recombinant MVA of claim 1 wherein said amino acid sequence is as set forth in SEQ ID NO:24.

15. The recombinant MVA of claim 2 wherein said nucleic acid sequence is as set forth in SEQ ID NO:23.

16. The recombinant MVA of claim 2 wherein said nucleic acid sequence is as set forth in SEQ ID NO:25.

* * * * *